United States Patent
Vendrell et al.

(10) Patent No.: US 11,252,156 B2
(45) Date of Patent: *Feb. 15, 2022

(54) SECURE DATA TRANSMISSION

(71) Applicant: IKONOPEDIA, INC., Dallas, TX (US)

(72) Inventors: Michael J. Vendrell, Dallas, TX (US); Michael Sokoryansky, Irving, TX (US)

(73) Assignee: Ikonopedia, Inc., Dallas, TX (US)

( * ) Notice: Subject to any disclaimer, the term of this patent is extended or adjusted under 35 U.S.C. 154(b) by 357 days.

This patent is subject to a terminal disclaimer.

(21) Appl. No.: 16/538,489

(22) Filed: Aug. 12, 2019

(65) Prior Publication Data

US 2019/0372978 A1 Dec. 5, 2019

Related U.S. Application Data

(63) Continuation of application No. 15/671,051, filed on Aug. 7, 2017, now Pat. No. 10,382,442, which is a continuation of application No. 15/361,605, filed on Nov. 28, 2016, now Pat. No. 9,729,554, which is a continuation of application No. 14/298,352, filed on Jun. 6, 2014, now Pat. No. 9,509,695, which is a continuation of application No. 14/085,388, filed on Nov. 20, 2013, now Pat. No. 8,868,768, which is a continuation of application No. 13/907,304, filed on May 31, 2013, now Pat. No. 10,102,348, which is a continuation of application No. 13/907,167, filed on May 31, 2013, now abandoned.

(60) Provisional application No. 61/728,580, filed on Nov. 20, 2012, provisional application No. 61/674,773, filed on Jul. 23, 2012, provisional application No. 61/666,492, filed on Jun. 29, 2012, provisional application No. 61/654,007, filed on May 31, 2012.

(51) Int. Cl.
*H04L 29/06* (2006.01)
*H04L 29/08* (2006.01)

(52) U.S. Cl.
CPC .......... *H04L 63/10* (2013.01); *H04L 63/0281* (2013.01); *H04L 67/32* (2013.01)

(58) Field of Classification Search
CPC ...... H04L 63/10; H04L 63/0281; H04L 67/32
USPC .................... 709/201, 229, 225, 217; 705/2; 715/748; 726/27
See application file for complete search history.

(56) References Cited

U.S. PATENT DOCUMENTS

| | | | | |
|---|---|---|---|---|
| 8,214,890 B2* | 7/2012 | Kirovski | ............... | H04L 9/3271 726/12 |
| 9,495,511 B2* | 11/2016 | Harrington | ............ | G16H 40/67 |
| 2004/0019564 A1* | 1/2004 | Goldthwaite | .......... | G06Q 20/12 705/44 |

(Continued)

*Primary Examiner* — Madhu Woolcock
(74) *Attorney, Agent, or Firm* — Ferguson Braswell Fraser Kubasta PC; Elizabeth Philip Dahm; Kelly J. Kubasta

(57) ABSTRACT

A system may include a first network in which user device(s) and a HIP server are communicably coupled. The first network may include a secure data administrator, such as a medical data system, that stores secure data. In some implementations, at least one of the user devices may include a web module and communicate with a web server through a second network. At least one of the user device may be restricted from communicating with the secure data administrator, so the user device may request data stored in the secure data administrator through the HIP server. The user device may base the requests for the data on information received from the web server.

19 Claims, 30 Drawing Sheets

(56) References Cited

U.S. PATENT DOCUMENTS

| | | | |
|---|---|---|---|
| 2006/0025670 A1* | 2/2006 | Kim | G16H 80/00 600/407 |
| 2006/0242159 A1* | 10/2006 | Bishop | G16H 40/67 |
| 2010/0306858 A1* | 12/2010 | McLaren | G16H 40/20 726/28 |
| 2012/0179908 A1* | 7/2012 | Duma | G16H 10/65 713/165 |

* cited by examiner

| | | | | | | | |
|---|---|---|---|---|---|---|---|
| GONZALEZ, LINDA 1974-01-06 (39y) #835872110 ‖ Bilateral Diagnostic | | | | | | | Scott Stoll (radio) ▼ |
| Date | Modality | | | Type | | | BIRADS: |
| No exam history available | | | | | | | |
| | | | | | | 740 ↲ History | |

760 →

| Patient | Birthdate | Size | Status | Date/Time | Mod | Exam | Radiologist |
|---|---|---|---|---|---|---|---|
| WOOD, PATRICIA J. 67y - F | 1945-06-19 | P1 | Ready | 2013-05-19 08:38:00 | MG: Diagnostic | Bilateral Diagnostic | Price R |
| GONZALEZ, LINDA 39y - F | 1974-01-06 | P2 | Hold | 2013-05-19 08:36:00 | MG: Diagnostic | Bilateral Diagnostic | Carlysle O |
| OWENS, MARGARET C. 49y - F | 1964-01-04 | P2 | Ready | 2013-05-19 08:34:00 | MG: Diagnostic | Bilateral Diagnostic | Price R |
| GIBSON, MARYANN T. 70y - F | 1943-02-27 | P1 | Ready | 2013-05-19 08:32:00 | MG: Diagnostic | Bilateral Diagnostic | Cluckey J |
| ROBERTSON, BETTY J. 40y - F | 1973-05-15 | P1 | Ready | 2013-05-19 08:30:00 | MG: Screening | Bilateral Screening | Callaway C |
| TUCKER, MARGERIE C. 46y - F | 1966-08-18 | P2 | Ready | 2013-05-19 08:28:00 | MG: Screening | Bilateral Screening | Smith B |
| MAY, SUSAN C. 50y - F | 1963-01-12 | P1 | Hold | 2013-05-19 08:26:00 | MG: Diagnostic | Bilateral Diagnostic | Carlysle O |
| SMITH, MARGERIE W. 73y - F | 1939-10-13 | P1 | Hold | 2013-05-19 08:24:00 | MG: Screening | Bilateral Screening | Carlysle O |
| GRAY, LINDA T. 68y - F | 1944-08-22 | | | 2013-05-19 08:22:00 | MG: Screening | Bilateral Screening | Carlysle O |

SECURE DATA TRANSMISSION

CROSS-REFERENCE TO RELATED APPLICATIONS

This application is in continuation of U.S. Nonprovisional patent application Ser. No. 15/671,051, entitled "SECURE MEDICAL DATA TRANSMISSION", filed on Aug. 7, 2017, issued on Aug. 13, 2019 as U.S. Pat. No. 10,382,442, which is a continuation of U.S. Nonprovisional patent application Ser. No. 15/361,605, entitled "SECURE MEDICAL DATA TRANSMISSION", filed on Nov. 28, 2016, issued on Aug. 8, 2017 as U.S. Pat. No. 9,729,554, which is a continuation of U.S. Nonprovisional patent application Ser. No. 14/298,352, entitled "SECURE MEDICAL DATA TRANSMISSION", filed on Jun. 6, 2014, issued on Nov. 29, 2015 as U.S. Pat. No. 9,509,695, which is a continuation of U.S. Nonprovisional patent application Ser. No. 14/085,388, entitled "SECURE MEDICAL DATA TRANSMISSION", filed on Nov. 20, 2013, issued on May 22, 2014 as U.S. Pat. No. 8,868,768, which claims priority to U.S. Provisional Patent Application No. 61/728,580, entitled "SECURE MEDICAL DATA TRANSMISSION", filed on Nov. 20, 2012, which are all hereby incorporated by reference for all purposes. This application is also a continuation of U.S. Nonprovisional patent application Ser. No. 13/907,167 which is entitled "IMAGE BASED MEDICAL DIAGNOSTIC SYSTEMS AND PROCESSES" and U.S. Nonprovisional patent application Ser. No. 13/907,304 which is entitled "IMAGE BASED MEDICAL REFERENCE SYSTEMS AND PROCESSES" both of which were filed on May 31, 2013, both of which claim priority to U.S. Provisional Patent Application Nos. 61/674,773 (entitled "System and Method for Image-Based Reporting and Analysis of Radiological Data" and filed on Jul. 23, 2012), 61/666,492 (entitled System and Method for Image-Based Reporting and Analysis of Radiological Data" and filed on Jun. 29, 2012) and 61/654,007 (entitled "System and Method for Image-Based Reporting and Analysis of Radiological Data" and filed on May 31, 2012), and all of which are hereby incorporated by reference for all purposes.

COPYRIGHT RIGHTS

A portion of the disclosure of this patent document contains material, which is subject to copyright protection. The copyright owner has no objection to the facsimile reproduction by any one of the patent document or the patent disclosure, as it appears in the Patent and Trademark Office patent file or records, but otherwise reserves all copyright rights whatsoever.

TECHNICAL FIELD

The present invention relates to the transmission of secure data.

BACKGROUND

With the introduction of electronic records (e.g., electronic medical records and/or other types of files) and digitized test results, a user, such as a physician can often form a diagnosis or other type of analysis while viewing appropriate records on a computer monitor. Data is often stored securely (e.g., for compliance with company, industry, and/or government standards and regulations). Access to the data is restricted to maintain the security of the data. For example, electronic medical records and digitized test results are often stored securely to comply with various regulations (e.g., industry and/or governmental). To maintain the security of the electronic medical records and test results, access to the data may be restricted and the systems that access the data may have restrictions (e.g., no Internet access, restricted Internet access, file copying to external drives may be restricted, and/or access to cloud computing may be restricted).

SUMMARY

In various implementations, accessing secure data may include requesting presentation of diagnostic interface(s) generated by an application device on a first user device. Presentation of secure data related to the diagnostic interface on a second user device may be requested via the diagnostic interface. Access to the secure data may be restricted and the secure data may be stored on a secure data administrator. The second user device and/or the secure data administrator may be restricted from accepting incoming communication initiated by the first user device. Instructions related to presentation of the secure data on the second user device may be received (e.g., by the first user device) from the application device. At least a portion of the instructions from the first user device may be transmitted to a HIP to allow presentation of at least a portion of the requested secure data on the second user device. The HIP may be communicably coupled to the first user device, the second user device and/or the secure data administrator. The HIP may be restricted from accepting incoming communication initiated by the application device.

Implementations may include one or more of the following features. The application device may include a web server. The application device may reside on a network external to the first user device, the second user device, the HIP, and/or the secure data administrator. The first user device may be distinct from the second user device. The first user device may not be communicably coupled to the second user device and/or the secure data administrator. The first user device may be communicably coupled to the HIP. The second user device, the HIP server, and/or the secure data administrator may be restricted from accepting incoming communications initiated by the first user device, the application device, and/or other computers with access to the Internet, in some implementations. The secure data may include sales data, personal data, engineering data, medical data, geological data, diagnostic images, legal information, and/or any other appropriate secure data. The instructions may include instructions (e.g., that when executed by a processor of the second user device and/or the secure data administrator) allow access and/or presentation of at least a portion of the requested secure data on the second user device. The instructions may be instructions to the second user device and/or the secure data administrator to request access and/or presentation of at least a portion of the requested secure data on the second user device. The instructions may include a format readable by the second user device and/or the secure data administrator. At least a portion of the instructions received by the HIP may be transmitted (e.g., by the HIP) to the second user device and/or the secure data administrator such that at least a portion of the requested secure data is presented on the second user device, in some implementations.

In various implementations, accessing secure data may include receiving a request (e.g., at the application device) for access on a first user device to diagnostic interface(s)

generated by an application device. A first request may be received (e.g., by the application device) from the first user device via one or more of the diagnostic interfaces. The first request may request presentation of secure data related to the diagnostic interface(s) on a second user device. The secure data may be stored on a secure data administrator. The second user device and/or the secure data administrator may be restricted from accepting incoming communication initiated by the first user device. The second user device and/or the secure data administrator may be restricted from accepting incoming communicating initiated by the application device. First instructions may be generated (e.g., by the application device) to present at least a portion of the requested secure data on the second user device at least partially based on the received first request. The generated instructions may be transmitted from the application device to the first user device. At least a portion of the generated first instructions may be received (e.g., at the HIP) from the first user device. The HIP may be communicably coupled to the first user device, the second user device, and/or the secure data administrator. The HIP may be restricted from accepting incoming communications initiated by the application device. Presentation of the requested secure data may be requested on the second user device (e.g., by the second user device and/or the secure data administrator) based on the received first instructions.

Implementations may include one or more of the following features. The HIP may be communicably coupled to the application device (e.g., via the internet) to allow outgoing communication (e.g., a key) from the HIP to the application device and/or to initiate communication with the application device and allow the application device to transmit information to the HIP based on the initiated communication by the HIP, in some implementations. The first instruction may include key(s). The HIP may be allowed to determine whether to allow access to the secure data based at least partially on the key. The HIP may determine whether the key in the received instructions is valid. The HIP may restrict access to the secure data if a determination is made that the key is not valid. In some implementations, the HIP may transmit at least a portion of the received instructions to allow presentation of the secure data on the second user device if a determination is made that the key is valid. The secure data may include diagnostic images. A connection may be established between the HIP server and the application device, and the HIP server may establish the connection. A second request may be transmitted from the HIP to the second user device and/or the secure data administrator to allow presentation of the requested secure data on the second user device. The second request may be based at least partially on the first instructions.

In various implementations, a system may include an application device and a second device. The application device may include a web server residing on a first network. The application device (e.g., the web server of the application device) may include a first memory that may store application device instructions and a first processor that may execute the first instruction(s). The application device instructions may be executed to generate diagnostic interface(s) to be presented on a first user device and receive at least one first request from a first user device (e.g., via the generated diagnostic interface(s)). The first request(s) may request presentation, on a second user device, of secure data related to one or more of the diagnostic interfaces. The secure data may be stored on a secure data administrator. The second user device and/or the secure data administrator may be restricted from accepting incoming communicating initiated by the first user device. The second user device and/or the secure data administrator may be restricted from accepting incoming communicating initiated by the application device. The application device instructions may be executed to generate first instructions to present at least a portion of the requested secure data on the second user device at least partially based on the received first request. The application device instructions may be executed to transmit the generated instructions to the first user device. The second device may reside on a second network. The second device may include a second memory comprising HIP instructions and a second processor adapted to execute one or more of the HIP instructions. The HIP instructions may be executed to receive at least a portion of the first instructions from the first user device and transmit at least a portion of the instructions to one of the devices on the second network to allow presentation of the secure data or portions thereof on the second user device. The second device may be restricted from accepting incoming communication initiated by the application device.

Implementations may include one or more of the following features. The first memory may store other data, such as instructions to generate diagnostic interfaces. The HIP instruction(s) may be executed to transmit at least a portion of the instructions to the second user device and/or the secure data administrator to allow presentation of the secure data administrator on the second user device. The second user device and the secure data administrator may reside on the second network. In some implementations, the system may include a first user device, a second user device, a HIP, and/or a secure data administrator. The HIP may reside on and or include the second device. The first user device may include a third memory, which may store first user device instruction(s), and a third processor, which may execute one or more of the first user device instructions. The first user device instructions may be executed to request access to the secure data on a second user device via one or more of the generated diagnostic interface and receive instructions from the application device to allow access to the secure data on the second user device. The first user device instructions may be executed to transmit the instructions or a portion thereof to the second device, wherein transmitting the instructions or a portion thereof to the second device allows secure data to be presented on the second user device. The second user device may include a presentation interface to present the secure data. The second user device may be communicably coupled to the secure data administrator. The second user device may be restricted from accepting incoming communication initiated by the first user device and/or the application device. In some implementations, the second device, the first user device, the second user device, and the secure data administrator may reside on the first network. The secure data may include diagnostic images. The second device may include a HIP server. The first user device may include a web module to perform operations with the application device.

In various implementations, access to secure data may be requested by a user. For example, a user on a first device, without access to the secure data, may request access to the secure data on a second device, which has access to the secure data. Rather than directly requesting the secure data on the second user device, the user may request access to the secure data via the first user device for presentation on the second user device.

In various implementations, a user may utilize a web-based application to, for example, assist in forming a diagnosis, assist in billing, and/or a variety of other appropriate tasks. The device and/or application on the device from which the user operates the web-based application may be restricted from accessing secure data, for example, for technical reasons (e.g. because web-based application may not be able to initiate communication unless using HTTP Internet protocol and/or cannot receive incoming communication; systems storing secure data may not support incoming HTTP and/or may need to initiate communications; and/or regulatory reasons, such as due to government, industry and/or facility restrictions attempting to maintain the secure nature of the data). The device may communicate with the web server (e.g., Internet/cloud-based web server) that facilitates communication between the device and a HIP (e.g., a proxy server) residing on the same network as the device. The HIP (e.g., proxy server) may translate and transmit requests to a system that includes the secure data and/or receive incoming requests from the system in any appropriate protocol, including protocols other than HTTP. The secure data may be transmitted such that the user may access the information.

In various implementations, accessing secure medical data using a HIP server may include requesting access to a diagnostic interface on a first user device. The diagnostic interface may be generated at least partially by an application device, which is a web server. Presentation of secure medical data on a second user device may be requested, via the diagnostic interface. The secure medical data may be stored on a secure data administrator, and the first user device may be restricted from communicating with the secure data administrator. The first user device may be restricted from communicating with the second user device. Instructions may be generated to provide access to the secure medical data. The instructions may include a key. The generated instructions may be transmitted to a HIP server, and the HIP server may be allowed to determine whether to allow access to the secure data based on the key. A request to present secure medical data on the second user device may be transmitted based at least partially on the instructions, if a determination is made to allow access to the secure data. The secure medical data may be presented on the second user device based on the request, if the determination is made to allow access to the secure data.

Implementations may include one or more of the following features. Generating instructions to allow access to the secure medical data may include generating instructions via the application device. The secure medical data may be related to a diagnosis provided via the diagnostic interface. The application device may receive a selection of a patient record via the diagnostic interface on the first user device and may automatically generate the request for secure medical data based at least partially on at the received selection. Transmitting a request to present secure medical data on the second user device may include transmitting at least a portion of the instructions to the secure data administrator. The processing of instructions by the secure data administrator may push the secure medical data to the second user device for presentation. In some implementations, transmitting a request to present secure medical data on the second user device may include transmitting at least a portion of the instructions to the second user device. The processing of the instructions by the second user device may include requesting the secure medical data from the secure data administrator. The secure medical data may include diagnostic images, test results, patient information, and/or electronic medical record.

In various implementations, accessing secure data using a HIP server may include requesting access to an interface on a first user device. The interface may be generated at least partially by an application device, which may include a web server. Presentation of secure data on a second user device may be requested via the interface. The secure data may be stored on a secure data administrator. The first user device may be restricted from communicating with the secure data administrator and/or the second user device. Instructions to allow access to the secure data may be generated, and transmitted to a HIP. The instructions may include a key, and the HIP may be allowed to determine whether to allow access to the secure data based on the key. A request to present secure data on the second user device may be transmitted based at least partially on the instructions, if a determination is made to allow access to the secure data. The secure data may be presented on the second user device based on the request, if the determination is made to allow access to the secure data.

Implementations may include on e or more of the following features. A selection may be received via the interface from the first user device, and the secure data associated with the received selection may be determined. Requesting presentation of secure data on the second user device may include requesting presentation of the secure data determined to be associated with the received selection. In some implementations, the HIP may be allowed to transmit a notification to the application device, establish a key with the application device by transmitting a key to the application device. A determination of whether to allow access to the secure data may include comparing the key to the key previously established with the application device. Transmitting a request to present secure data on the second user device may include transmitting at least a portion of the instructions from the HIP server to the second user device. In some implementations, transmitting a request to present secure data on the second user device may include transmitting at least a portion of the instructions from the HIP server to the secure data administrator. The instructions may include instructions to push the secure data from the secure data administrator to the second user device. The secure data may be presented on the second user device. Access to the secure data may be restricted if a determination is made to not allow access to the secure data. The first user device may not be communicably coupled to the HIP via VPN.

In various implementations, a method of accessing secure data may include receiving instructions on a HIP from a first user device to present secure data on a second user device. The instructions may include a key. The HIP server may be communicably coupled to the first user device. The secure data may be stored on a secure data administrator. The first user device may not be communicably coupled and/or restricted from communicating with the second user device and/or the secure data administrator. A determination may be made whether the key in the received instructions is valid. Access to the secure data may be restricted if the determination is made that the key is not valid. At least a portion of the received instructions may be transmitted to allow presentation of the secure data on the second user device if the key is determined to be valid.

Implementations may include one or more of the following features. A notification may be transmitted to an application device, and a key may be established with the application device. In some implementations, a notification may be transmitted to an application device, and a key may be established with the application device by transmitting the key to the application device. Validating the key in the received instructions may include comparing the key to a key previously established with a application device, a determination may be made regarding whether the key is valid is based at least partially on the comparison. Transmitting at least a portion of the received instructions to allow presentation of the secure data on the second user device may include transmitting at least a portion of the received instructions to the second user device. The second user device may request and receive the secure data based at least partially on the received instructions. In some implementations, transmitting at least a portion of the received instructions to allow presentation of the secure data on the second user device may include transmitting at least a portion of the received instructions to the secure data administrator. The secure data administrator may transmit the secure data based at least partially on the received instructions.

In various implementations, a method of accessing secure data may include transmitting a first request from a first user device to an application device, which is a web server. The first request may be related to access on a second user device to medical data. Access to the medical data may be restricted and the medical data may be stored on a secure data administrator. The first user device may be restricted from communicating with the second user device and the secure data administrator. Instructions may be received from the application device at least partially based on the transmitted first request. At least a portion of the instructions may be transmitted to a HIP (e.g., HIP server, which may be a proxy server), which allows presentation of the requested medical data on the second user device. The HIP server may be communicably coupled to the first user device, the second user device, and/or the secure data administrator.

Implementations may be include one or more of the following features. The medical data may include diagnostic images, patient information, and/or electronic medical record. The first response may include a key, and the key may be validated by the HIP server. A second request may be transmitted from the HIP server to the second user device to allow presentation of the requested medical device on the second user device. A second request may be transmitted from the HIP server to the secure data administrator to allow presentation of the requested medical device on the second user device. The HIP server may be adapted to initiate outgoing communication via the Internet and restricted from accepting incoming communication from the Internet.

In various implementations, transmitting secure data may include transmitting a first request from a first user device to an application device, and receiving instructions from the application device at least partially based on the transmitted first request. The first request may be related to access on a second user device to medical data. Access to the medical data may be restricted, and the medical data may be stored on a secure data administrator. The first user device may be restricted from communicating with the second user device and the secure data administrator. The application device may include a web server. At least a portion of the instructions may be transmitted to a HIP server, which allows presentation of the requested medical data on the second user device. The HIP server may be communicably coupled to the first user device, the second user device, and/or the secure data administrator.

Implementations may include one or more of the following features. The medical data may include diagnostic images, patient information, and/or electronic medical record. The first response may include a key, and the key may be validated by the HIP server. A second request may be transmitted from the HIP server to the second user device to allow presentation of the requested medical device on the second user device. In some implementations, a second request may be transmitted from the HIP server to the secure data administrator to allow presentation of the requested medical device on the second user device. The HIP server may be adapted to initiate outgoing communication via the Internet and restricted from accepting incoming communication from the Internet.

In various implementations, a system may include an application device, a HIP server, a secure data administrator, a first user device, and a second user device. The application device may include a web server adapted to generate one or more interfaces. The HIP server may be adapted to initiate communication with the application device and restricted from accepting incoming communication from the application device. The secure data administrator may store secure medical data. The application device may be restricted from communicating with the secure data administrator. The first user device may include a memory storing first user device instructions, and a processor adapted to execute one or more of the first user device instructions. The first user device instructions may include: requesting access to the secure medical data on a second user device via the generated interface, receiving instructions from the application device for access to the secure medical data, and transmitting the instructions to the HIP server. Transmitting the instructions to the HIP server may allow secure data to be presented on the second user device. The first user device may not be communicably coupled to the second user device and may be restricted from communicating with the secure data administrator.

Implementations may include one or more of the following features. The system may include a first network. The HIP server, the first user device, the second user device, and the secure data administrator may reside on the first network. In some implementations, the HIP server may establish a connection between the HIP server and the application device. The system may include a second user device. The second user device may include presentation interface for presenting the secure data. The second user device may be communicably coupled to the secure data administrator and may be restricted from accepting communication from the application device and the first user device. The HIP server may include a memory storing HIP instructions and a processor adapted to execute HIP instruction(s). The HIP instructions may include receiving the instructions from the first user device and transmitting at least a portion of the instructions to the secure data administrator to allow presentation of the secure data administrator on the second user device. In some implementations, the HIP instructions may include receiving the instructions from the first user device and transmitting at least a portion of the instructions to the second user device. The second user device may request the secure data from the secure data administrator based at least partially on the instructions. In some implementations, the HIP instructions may include determining whether to allow access to the secure medical data based at least partially on the instructions. The secure medical data may include diagnostic images, in some implementations. The application device may generate one or more diagnostic interfaces. The first user device may include a web module adapted to perform operations with the application device.

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which:

FIGS. 17A-7D illustrate implementations of example work-list graphical user interfaces.

FIG. 20 illustrates an implementation of an example location graphical user interface.

FIG. 22 illustrates an implementation of an example report graphical user interface.

Like reference symbols in the various drawings indicate like elements.

DETAILED DESCRIPTION

Figure 1:
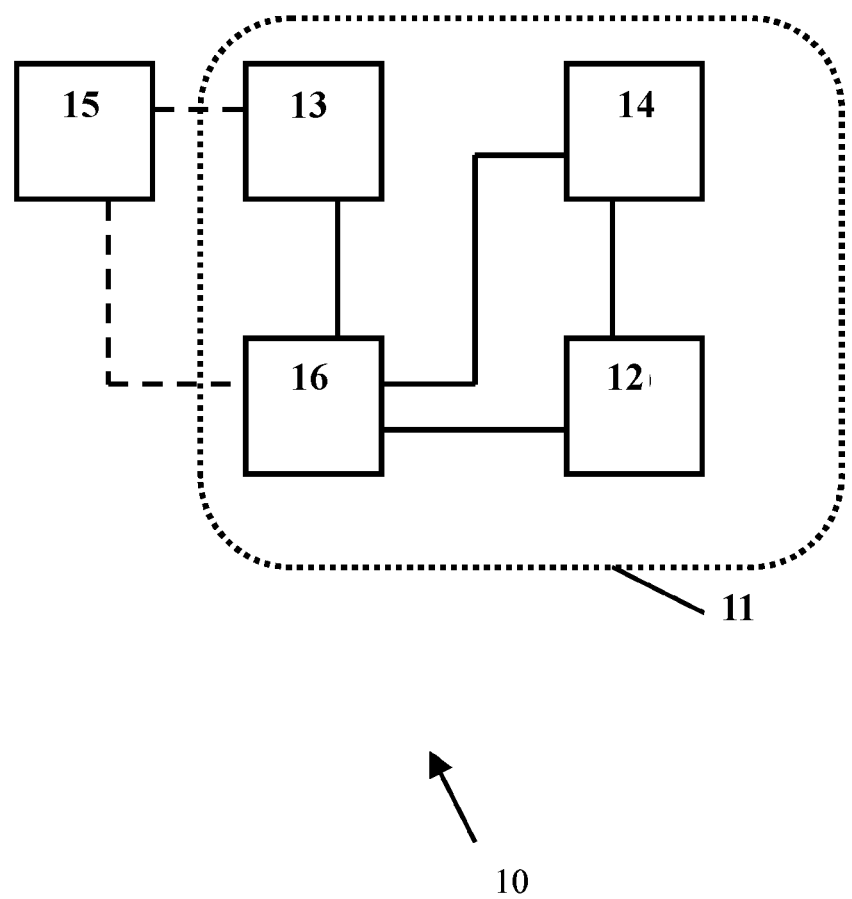
FIG. 1 illustrates an implementation of an example system that facilitates transmission of secure data.

Data is often stored securely. For example, medical data, corporate data, human resources data, marketing data, sales data and/or other data may be stored securely. When data is stored securely, access to the data (e.g., presentation, editing, and/or adding data) may be restricted. For example, computers with access to the Internet may be restricted from accessing the secured data (e.g., the computer may be restricted and/or a secure data administrator may not receive incoming requests from computers with Internet access). In some implementations, access to the secure data may be restricted to computers with specified access restrictions (e.g., restricted from specified Internet sites, restricted from Internet access, restricted from access outside a specified network, and/or other appropriate restrictions).

For example, in the medical industry, data, such as medical data, is often securely stored and/or transmitted based at least partially on facility (e.g., hospital and/or clinic), industry, and/or government (e.g., Health Insurance Portability and Accountability Act of 1996 or HIPPA) regulations. Access to the data may be restricted and/or restrictions (e.g., no Internet access and/or restricted Internet access) may be imposed on devices that are used to access the secure data.

However, a user may utilize various web-based interfaces related to the secure data. For example, a user may access a web-based interface to provide diagnostic and/or analytical information related to the secure data. In some implementations, the user may access a web-based workflow management interface related to the secure data. Thus, access to the secure data on the computer in which the web-based interfaces are presented may be restricted (e.g., since computers with Internet access may be restricted from accessing secure data).

In various implementations, access to secure data may be requested by a user on a first user device. For example, a user on a first device, without access to the secure data, may request access to the secure data on a second device, which has access to the secure data. Rather than directly requesting the secure data on the second user device, the user may request access to the secure data via the first user device for presentation on the second user device. In some implementations, automatically requesting the presentation of secure data on a device that is able to present the secure data using the web-based interface on the first user device may improve productivity (e.g., by decreasing the number of steps utilized to access the secure data), increase accuracy, and/or reduce errors. For example, if the user manually requests the secure data on the second user device, an entry error may cause the user to be presented with different secure data. Thus, errors may be reduced.

In the medical industry, for example, users utilizing web-based software (e.g., to facilitate diagnosing patients and/or to perform research related to medical data, such as test results) may need access to secure data. However, in some implementations, access to the data may be restricted on the user device, since the user device has access to the Internet and/or because the data may reside on medical systems that are not connected to and/or accessible from the Internet. Thus, a user may request access to the secure data on a second user device, which has access to the secure data, from a first user device. By automatically requesting presentation of the secure data, errors may be inhibited since the appropriate secure data may be automatically requested. For example, if a user utilizes a first user device to provide diagnostic information for a patient via a web-based interface and then uses a second user device to request related secure data such as a medical records, information, and/or diagnostic images (e.g., CT scan, MRI, ultrasound, digital x-ray), the wrong patient information may be presented to the user due to errors (e.g., misentry of patient information on second user device, misreading patient information on first device, and/or erroneous key strikes such as hitting the back button to display previously presented information). Thus, errors may be inhibited by automatically requesting the appropriate secure data for presentation on a second user device through an interface on the first user device.

FIG. 1 illustrates an example system 10 that facilitates transmission of secure data. As illustrated, the system 10 includes a Network A 11. The Network A 11 may couple various components in the system 10 and provide one or more levels of access and/or communications within and/or outside Network A.

The system may include a Secure Data Administrator (SDA) 12. The SDA 12 may be any appropriate device, such as a server. The SDA may include and/or be coupled to a memory (e.g., a repository) that stores secure data and/or unsecure data. The secure data may be any appropriate data such as sales data (e.g., sales reports, marketing reports, contact lists, and/or images), personal data (e.g., passwords and/or other personal data such as financial data), medical data (e.g., diagnostic images, patient information, hospital information, and/or electronic medical record), engineering data (e.g., drawings, plans, reports, and/or other appropriate information), legal information (e.g., notes, analysis, cases, and/or opinions), geological information (e.g., surveys, seismology reports), and/or any other appropriate data data. Access (e.g., read and/or write) to the secure data may be provided and/or restricted by the SDA according to access criteria. For example, the access criteria may include restricting access to computers that accept communications outside of the network (e.g., Network A 11). In some implementations, only specified user devices may access the SDA.

A user may utilize more than one user device while performing functions. For example, a user may utilize a first user device A 13 and a second user device 14. The user devices may be any appropriate device, such as a laptop, desktop, smart phone and/or tablet computer. As illustrated, the user devices may not be communicably coupled. For example, user device A 13 may not be coupled (e.g., via Ethernet, via the Internet, and/or via USB) to user device B 14. In some implementations, user device A 13 or portions thereof (e.g., pertinent software, such as web applications and/or modules, running on user device A) may not support communication protocols supported by user device B 14. For example, user device B 14 may not be able to understand instructions transmitted from user device A 13 to user device B 14 based at least partially on the communication protocol utilized in the instructions. Thus, user device A may not be able to directly communicate with user device B 14.

User device A 13 and user device B 14 may reside in Network A 11. User device A 13 may have access outside Network A. For example, user device A 13 may have access to the Internet. Thus, user device A 13 may be capable of accessing web-based interfaces, such as diagnostic interfaces and/or analysis interfaces. Since user device A 13 has access outside Network A 11 (e.g., via the Internet), user device A may be restricted from accessing the secure data stored on SDA 12. In some implementations, user device A or portions thereof (e.g., pertinent applications running on user device A) may not support communication protocols supported by SDA 12. For example, user device A and SDA 12 may not be communicably coupled.

The second user device B 14 may be able to access the secure data. For example, the second user device B 14 may be communicably coupled to the SDA 12. The second user device B 14 may have restrictions that satisfy the access criteria of the SDA 12. For example, the second user device B 14 may be restricted from accessing the Internet and/or may be restricted from accepting incoming communications from devices that have access to the Internet.

Thus, the user may utilize the first user device A 13 to access a web-based interface and a second user device B 14 to access secure data stored in the SDA 12. For example, when a user utilizes a first interface, presentation of secure data (e.g., at least a portion of the secure data stored in the SDA or a repository coupled to the SDA) to the user may facilitate providing the appropriate entry in the first interface. However, rather than a user requesting the secure data via the second user device B 14 (e.g., which may cause errors), presentation of the secure data on the second user device B may be requested via the first user device A 13 (e.g., via the first interface presented on the first user device).

An Application Device (AD) 15 may generate the web-based interface utilized by the first user device A 13. The AD 15 may be a web server. The AD 15 may run applications (e.g., enterprise applications, diagnostic applications, analysis applications, data management applications, workflow applications, and/or other appropriate applications). The AD 15 may run an application and generate interfaces (e.g., graphical user interfaces) that can be presented to users (e.g., on a presentation device of a user device). For example, a user on a first user device A 13 may access a web site that includes interfaces generated by the AD 15. The user may provide selections (e.g., via free-form, text boxes, fields, icons, and/or other appropriate selection techniques) and/or be presented with information through the interfaces.

The AD 15 may not reside on the same network, such as Network A 11, as first user device A 13, second user device B 14, and/or SD 12. The AD 15 may not be able to access secure data stored on SD 12. The AD 15 may not be able to access and/or communicate with SDA 12 (e.g., since SDA may be restricted from communicating and/or from being communicably coupled with devices that have access to the Internet). The AD 15 may not be able to communicate with second user device B 14 (e.g., since second user device B may be restricted from communicating and/or from being communicably coupled with devices that have access to the Internet).

The system may include a HIP 16. A HIP 16 may include any appropriate device such as a server. In some implementations, the HIP 16 may include a proxy server. The HIP 16 may reside on the same network (e.g., Network A 11) as the SDA 12. The HIP 16 may include a set of instructions, such as the described operations, stored in a memory of a device of the system and executed by the processor of the device.

Figure 2:
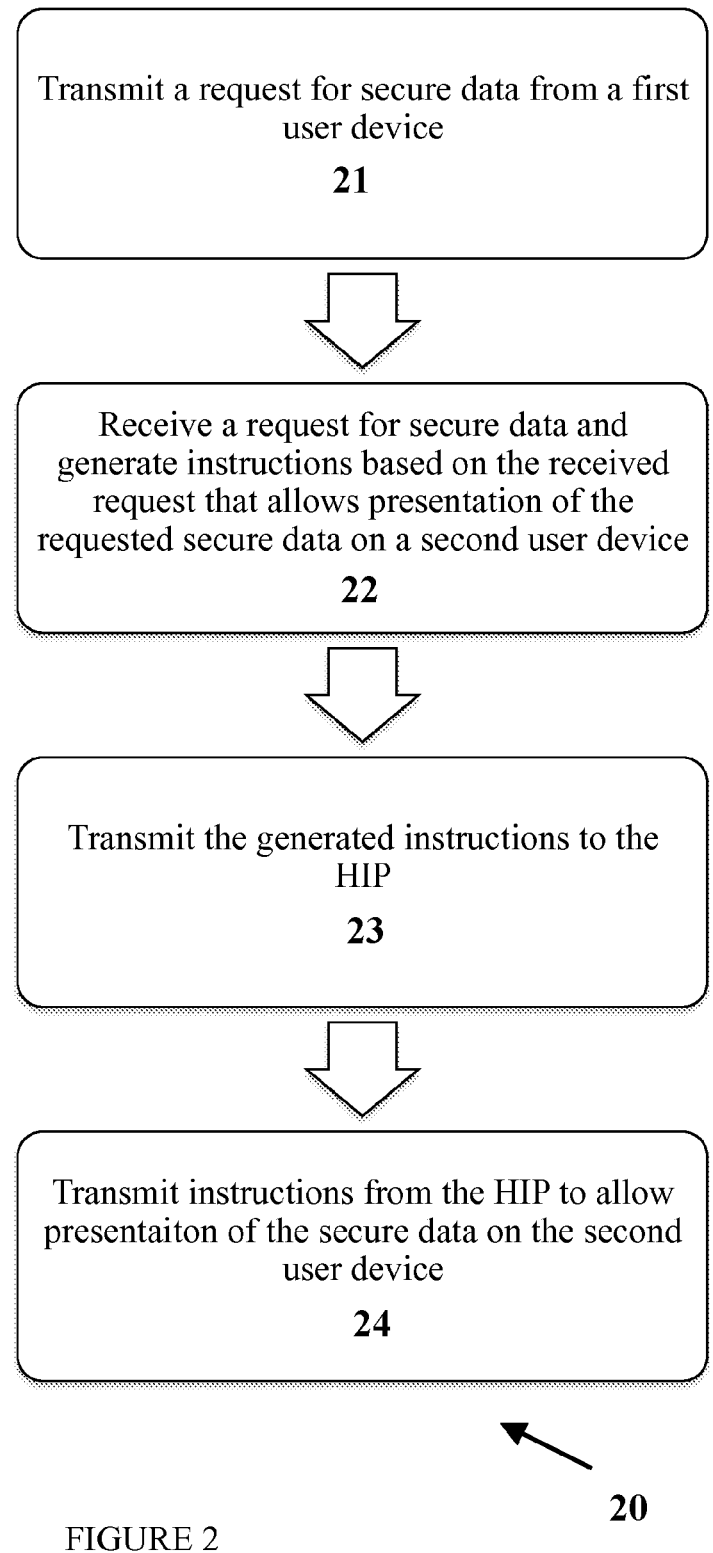
FIG. 2 illustrates an implementation of an example process that facilitates transmission of secure data.

The HIP 16 may facilitate the presentation of information on the second user device B 14 based on requests from a first user device A 13, which is restricted from accessing the secure data and the second user device B. FIG. 2 illustrates an implementation of an example process 20 for utilizing a HIP to facilitate transmissions of secure data.

A request for secure data may be transmitted from a first user device A 13 (operation 21). The request may include a request for presentation of the requested secure data on presentation on a second user device (e.g., specified in the request). For example, the first user device A 13 may be utilized to access a web-based interface. A user may provide a selection through the interface that requests access to secure data. In some implementations, secure data and unsecure data may be requested via the first user device A 13.

The AD 15 may receive the request for secure data and generate instructions based on the received request that allows presentation of the requested secure data on the second user device B (operation 22). For example, the AD 15 may receive the request and generate instructions that identify the secure data, the SDA 13, and/or the second user device B 14. The AD 15 may generate the instructions based on properties (e.g., communication protocol and/or identification information) of the SDA 13 and/or second user device 14.

The generated instructions may be transmitted to the HIP 16 (operation 23). For example, the AD 15 may transmit the generated instructions to the first user device A 13 and the first user device A may transmit the instructions to the HIP 16. Since the HIP 16 may be restricted from receiving communications from devices not residing on the network (e.g., Network A 11) on which the HIP resides, the AD may be restricted from directly transmitting the generated instructions to the HIP 16. In some implementations, HIP 16 may support communications protocols, such as HTTP (HyperText Transfer Protocol) so that device A or portions thereof (e.g., application running on device A) may initiate communicate with HIP 16.

The instructions may be transmitted by HIP 16 to allow presentation of the secure data on the second user device B 14 (operation 24). For example, the HIP 16 may transmit the instructions to the second user device 14 and/or the SDA 12. The instructions may be received, stored and/or processed by the second user device 14 and/or the SDA 12, as appropriate. In some implementations, when the second user device 14 receives the instructions, the instructions may be in a format compatible with other software applications executable by the second user device for the viewing and/or retrieving of the secure data. Thus, the second user device may transmit the received instructions to the other software data for retrieval and/or presentation of the secure data.

Process 20 may be implemented by various systems, such as system 100. In addition, various operations may be added, deleted, and/or modified. For example, the first user device A, second user device B, HIP, and SDA may reside on network A. The AD may reside on a network B, different from network B. The AD may be restricted from accessing portions of network A, such as the SDA. In some implementations, the process may be implemented in a medical environment (e.g., hospital, clinic, practice group, and/or other medical associations). The secure data may be secure medical data, such as diagnostic image(s), billing information, patient information, test results, electronic medical record(s) or portions thereof, and/or any other appropriate medical data. For example, the secure data may be data available through RIS (radiological information system), BRIS (breast specific radiological information system), and/or PACS (picture archiving and communication system) and/or other medical data viewing software. The process may be performed to maintain security of the data (e.g., in compliance with government, industry, and/or company standards and/or regulations). In some implementations, at least a portion of the secure data may include unsecure data.

Although FIG. 1 illustrates an implementation of a system that facilitates secure communications, other implementations may be utilized as appropriate. For example, the system may not utilize VPN (Virtual private networking). In some implementations, the user device A and/or the AD may not utilize VPN to communicate with devices in Network A and/or each other. In some implementations, the first user device, second user device, AD, SDA, and/or HIP may include any appropriate device, such as a computer.

In some implementations, the access criteria may allow access to computers that do not accept communications from outside the network. In some implementations, the access criteria may be based on Internet accessibility. For example, if a computer is allowed to access and/or accept communications via the Internet, then the computer may be restricted from access. If a computer is not allowed to access and/or accept communications via the Internet, then the computer may be allowed access. In some implementations, the access criteria may include restricting access based on communication language. For example, if a computer communicates (e.g., sends requests) via HTTP, then access may be restricted.

In some implementations, the SDA may restrict the first user device 13 from accessing secured data due to the ability of the first user device to access the Internet. The SDA may not accept communications from the first user device 13 because the first user device has access outside the network on which the SDA resides, network A.

Figure 3:
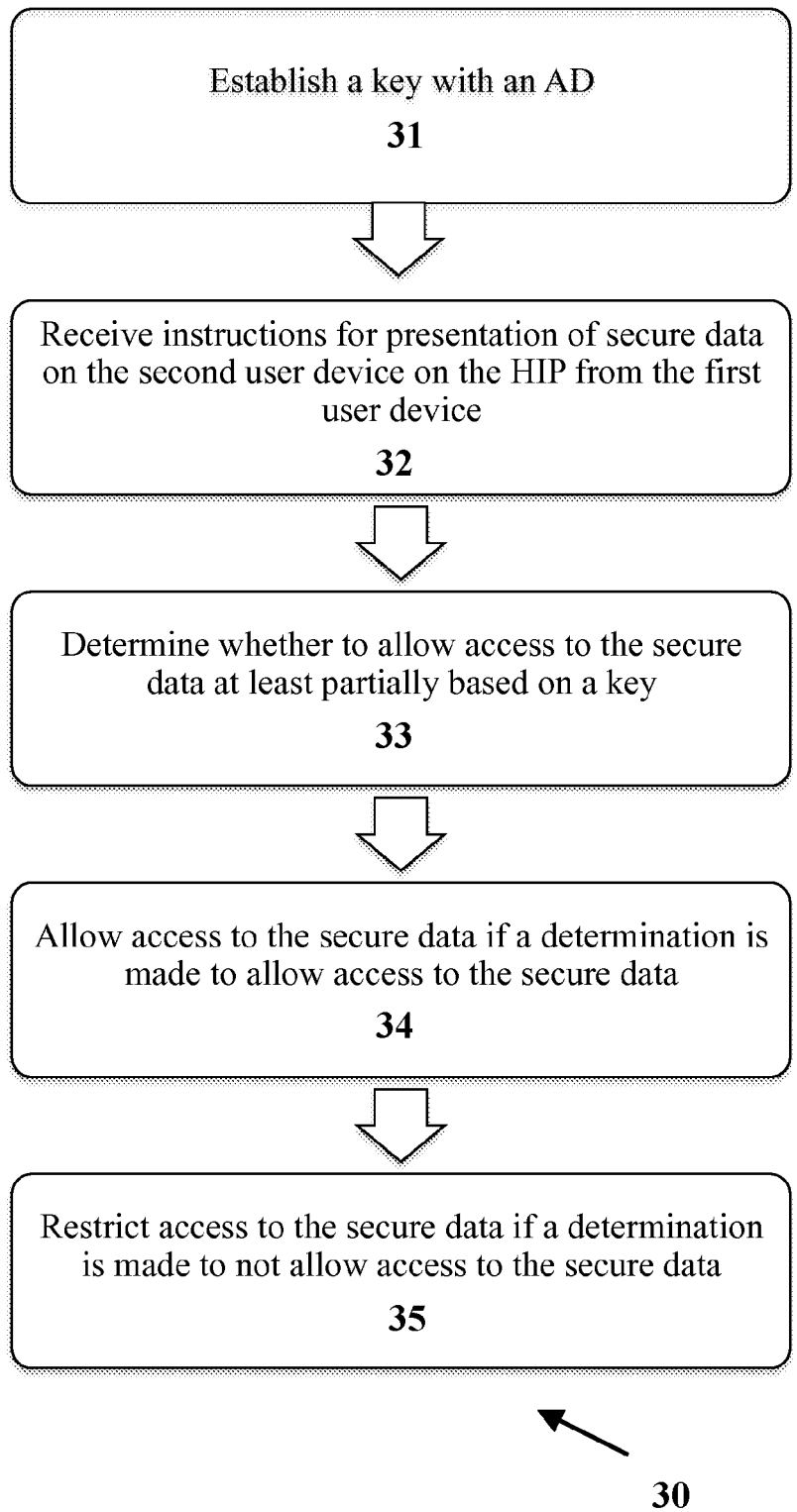
FIG. 3 illustrates an implementation of an example process that facilitates transmission of secure data via a HIP.

In some implementations, the HIP may facilitate presentation of the secure data on a second user device. FIG. 3 illustrates an implementation of an example process 30 for utilizing the HIP to facilitate presentation of the secure data on a second user device. The HIP may establish a key with an AD (operation 31). For example, the HIP may transmit a notification to the AD (e.g., since the HIP may be restricted from receiving incoming communications from outside the network on which the HIP resides). The notification may include information about the HIP (e.g., identity, location information, any appropriate security association such as a key, and/or communication protocol), information about user devices, information about SDA, information about a network on which the HIP resides, and/or any other appropriate information.

Instructions may be received on the HIP from a first user device for presentation of secure data on a second user device (operation 32). A first user device may transmit to the AD a request for access to secure data to be presented on a second user device. The AD may analyze the request for access and generate instructions to allow presentation of secure data on the second user device. For example, the AD may generate the instructions based on communication protocols, identity of the first user device, identity of the second user device, identity of the SDA, information about the HIP (e.g., identity of the HIP and/or an established key) and/or other appropriate information. The generated instructions may be transmitted to the first user device, which transmits the instructions or portions thereof to the HIP. The HIP may be communicably coupled to the first user device, the second user device, and/or the SDA. The AD may be restricted from directly communicating with the HIP (e.g., since the HIP may not accept incoming communications from Internet applications), in some implementations.

A determination may be made whether to allow access to the secure data based at least partially on a key (operation 33). The key may be included in the instructions. For example, the AD may retrieve a key previously established with the HIP (e.g., established daily, monthly, manually, and/or automatically). The AD may include the retrieved key in the generated instructions to allow transmission to the first user device. The HIP may analyze the key to determine whether it is a valid key based on validation criteria, for example.

Access to the secure data may be allowed if a determination is made that access to the secure data is to be allowed (operation 34). For example, the HIP may transmit the instructions or portions thereof such that the secure data may be retrieved from a SDA and presented on the second user device. The HIP may determine the appropriate device to which the instructions may be transmitted and transmit the instructions to the appropriate device. The secure data may then be retrieved and/or pushed to the second user device and presented on a presentation interface of the second user device.

Access to the secure data may be restricted if a determination is made that access to the secure data is not allowed (operation 35). For example, the HIP may not transmit the instructions. The HIP may restrict the transmission of the secure data, in some implementations.

Process 30 may be implemented by various systems, such as system 100. In addition, various operations may be added, deleted, and/or modified. In some implementations, process 30 may be performed in combination with other processes or portions thereof, such as process 20. For example, establishing a key with an AD may include transmitting a key to the AD. In some implementations, the HIP may not receive a key with the instructions. In some implementations, other types of security associations may be included in the HIP and the HIP may validate based on the other type of security associations. The HIP may not validate the key, in some implementations. The HIP may establish a key with the first user device and validate based at least partially based on the established key.

In some implementations, the process may be implemented in a medical environment (e.g., hospital, clinic, practice group, and/or other medical associations). The secure data may be secure medical data, such as diagnostic image(s), billing information, patient information, electronic medical record(s), and/or any other appropriate medical data. For example, the secure data may be data available through RIS, BRIS, and/or PACS and/or other medical data viewing software. The process may be performed to maintain security of the data (e.g., in compliance with government, industry, and/or company standards and/or regulations). In some implementations, at least a portion of the secure data may include unsecure data.

Determining whether to allow access to the secure data based on the key may include identifying the key. In some implementations, the HIP may parse or otherwise analyze the received instructions to identify the key. The key may be compared to an established key. For example, a key transmitted to the AD for establishing a key may be retrieved and compared to the key received in the instructions. If the key is the same as the established key, then a determination may be made to allow access to the secure data. If the key is not the same as the established key, then a determination may be made to restrict access to the secure data.

In some implementations, the HIP may transmit a notice to the first user device based at least partially on the determination of whether to allow access to the secure data. For example, the HIP may transmit a notification to the first user device and/or the second user device that the transmission will be processed and/or the secure data will be transmitted on the second user device. The HIP may transmit a notification to the first user device and/or the second user device that access to the secure data is restricted, in some implementations.

The HIP may be a proxy server. In some implementations, the HIP may transmit the instructions to the SDA. The SDA may be restricted from receiving instructions from the first user device and/or the AD, and thus the HIP may transmit the instructions. The SDA may retrieve the secure data based on the instructions received by the SDA (e.g., previously generated by the AD and transmitted to the HIP via the first user device). The SDA may then transmit (e.g., push) the retrieved secure data to the second user device. The transmitted secure data may then be presented on a presentation interface of the second user device.

In some implementations, the HIP may transmit the instructions to the second user device. Since second user device may be restricted from communications with (e.g., restricted from accepting communications from) the first user device and/or the AD, the HIP may transmit the instructions to the second user device. The second user device may then request the secure data based on the received instructions from the SDA. For example, the second user device may include an application for accessing, presentation, creation and/or editing of the secure data. The second user device may request the secure data through the application based on the received instructions. The SDA may receive the request from the second user device and retrieve the secure data (e.g., from a repository, local and/or remote to the SDA). The SDA may then transmit the secure data to the second user device. The second user device may then present the secure data.

Figure 4:
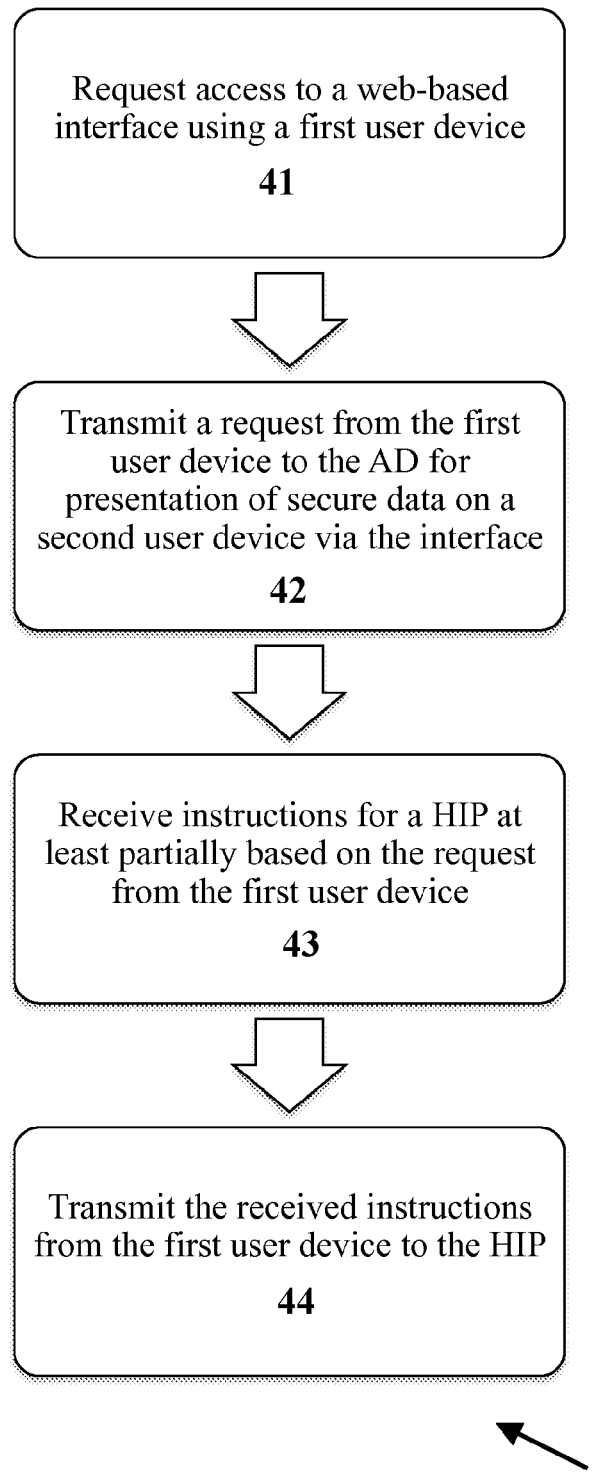
FIG. 4 illustrates an implementation of an example process that facilitates transmission of secure data.

In some implementations, a first user device, which is not coupled to the SDA, may be used to initiate requests for access to the secure data. The first user device may be used to access web-based interfaces that provide information related to the secure data and/or about the secure data. By allowing the secure data requests to be initiated by the first user device, errors (e.g., due to reading which secure data should be requested on the second user device and/or due to entering the secure data request erroneously) may be minimized and/or inhibited. FIG. 4 illustrates an implementation of an example process 40 for utilizing a first user device.

Access to a web-based interface may be requested by the first user device (operation 41). The first user device may be coupled to an AD. For example, a website that includes interfaces generated by an AD (e.g., a web server operating an application for providing information, such as diagnoses, patient information, information about secure data, information related to secure data, analysis, etc.) may be accessed using a first user device.

A request may be transmitted from the first user device to the AD for presentation of secure data on the second user device via the interface (operation 42). The first user device may not have access to the secure data (e.g., the first device is not communicably coupled to the SDA and/or the SDA is restricted from accepting incoming communication from the first user device). Thus, the first user device may request presentation of secure data on a second user device via the interface. The first user interface may not be communicably coupled to the second user device, and thus may utilize other components of the system (e.g., AD, HIP) to request presentation of secure data on the second user device.

Instructions for a HIP may be received at least partially based on the request by the first user device (operation 43). For example, the AD may receive the request for presentation of secure data on the second user device and generate instructions based on the request. The instructions may be in a format (e.g., language) that the HIP is adapted to receive. The instructions may be in a format that the second user device and/or the AD is adapted to receive such that the instructions may be operable by the second user device and/or the AD to retrieve and/or present secure data.

The received instructions may be transmitted to a HIP from the first user device (operation 44). Since the AD may be inhibited from initiating communications with the HIP (e.g., since the AD is not on the same network as the HIP), the first user device may transmit the instructions generated by the AD to the HIP. The first device may be restricted from communicating directly with the second user device and so the first device may transmit the instructions to the HIP to indirectly transmit instructions, responses, and/or requests with the second user device and/or SDA. Transmission of the received instructions may allow presentation of the secure data on a second user device. For example, the HIP may transmit the instructions received to the second user device and/or the AD such that the secure data is retrieved from the AD and presented on a presentation interface of the second user device.

The secure data may be retrieved and presented on a second user device. The secure data may be related to the information presented on and/or information provided by the first user device via the interface. By automatically requesting the secure data related to the information presented and/or provided through the interface on the first user device, errors due to requesting unrelated data may be inhibited.

Process 40 may be implemented by various systems, such as system 100. In addition, various operations may be added, deleted, and/or modified. In some implementations, process 40 may be performed in combination with other processes or portions thereof, such as process 20 and/or 30. The HIP may be a proxy server. A notification may be received from the HIP based at least partially on the received instructions. For example, the HIP may transmit a notification that an error occurred (e.g., invalid key, invalid path for secure data to be retrieved, etc.). The HIP may transmit a notification to the first user device that a transmission was received and/or retransmitted successfully In some implementations, the process may be implemented in a medical environment (e.g., hospital, clinic, practice group, and/or other medical associations). The secure data may be secure medical data, such as diagnostic image(s), billing information, patient information, electronic medical record(s), and/or any other appropriate medical data. For example, the secure data may be data available through RIS (radiological information system), BRIS (breast specific radiological information system), and/or PACS (picture archiving and communication system) and/or other medical data viewing software. The process may be performed to maintain security of the data (e.g., in compliance with government, industry, and/or company standards and/or regulations). In some implementations, at least a portion of the secure data may include unsecure data.

In some implementations, a selection may be provided by the first user device via the interface. The selection may correspond to secure data. For example, the interface may manage workflow and a selection of an item in the workflow may be associated with secure data. The AD may determine which secure data (e.g., kind, type, location, record information, and/or any other appropriate information) should be requested and/or automatically request access to the appropriate secure data.

In some implementations, the AD may generate the instructions including a key or other security application. The key may be associated with the HIP. For example, the key may be a key established between the AD and the HIP. The HIP may determine whether to allow access to the secure data based at least partially on the key in the instructions. For example, the HIP may compare the key to the key established with AD(s) and determine whether the keys are the same. If the key and the established key are the same, then the HIP may transmit the instructions or portions thereof to allow presentation of the secure data on the second presentation device. If the key and the established key are not the same, then the HIP may restrict transmission of the instructions.

Figure 5:
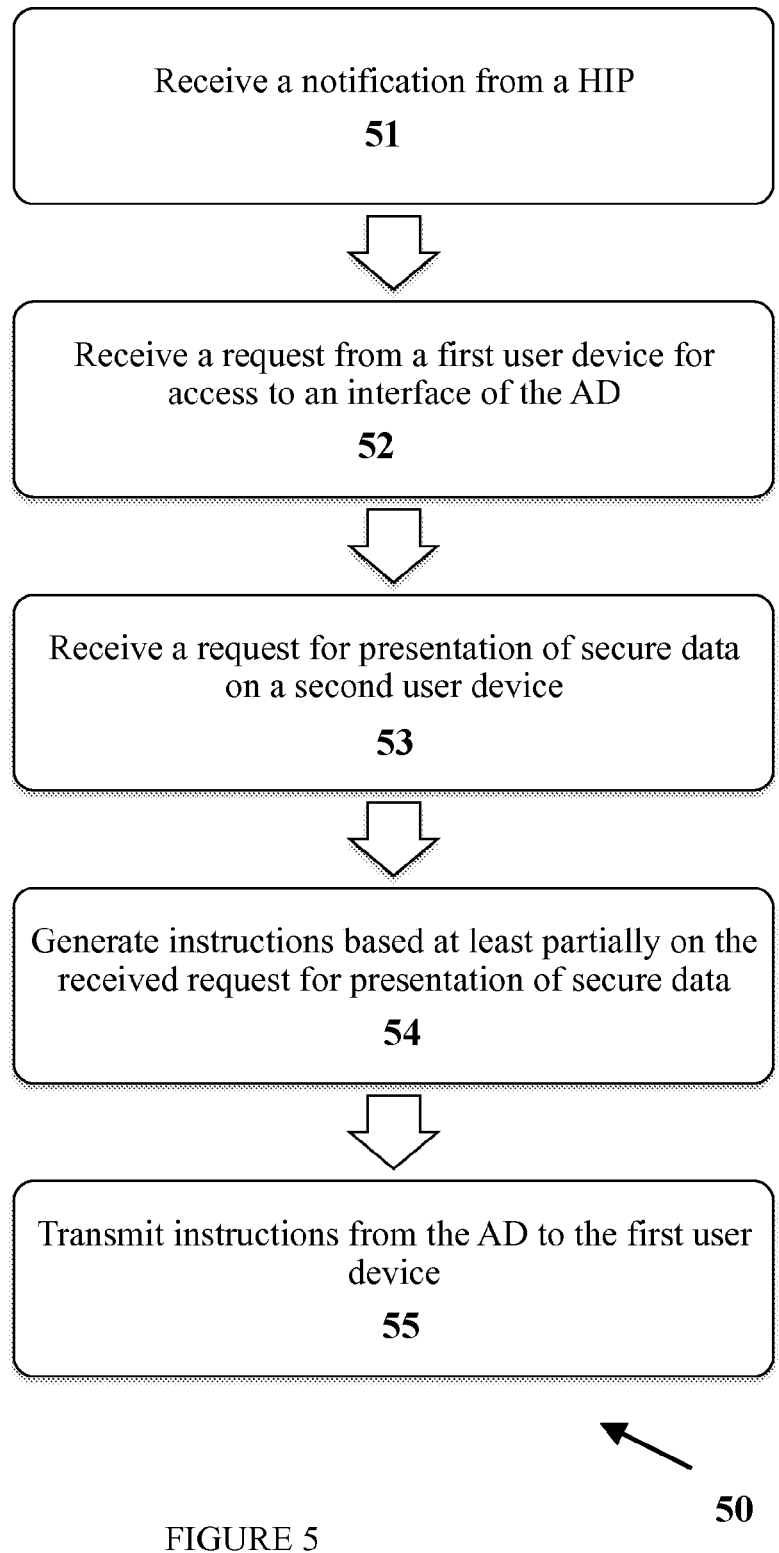
FIG. 5 illustrates an implementation of an example process that facilitates transmission of secure data

FIG. 5 illustrates an implementation of an example process 50 for facilitating transmission of secure data using a web-based AD. A notification may be received from a HIP (operation 51). The notification may at least partially establish a key between the HIP and the AD. For example, the notification may include a key and/or identifying information about the HIP.

A request may be received from a first user device for access to an interface of the AD (operation 52). For example, the AD may generate interfaces (e.g., graphical user interfaces (GUIs)) that the first user device may access via the Internet. The interfaces may allow a user to make selections, request secure data, provide information related to secure data, view other information, and/or other appropriate functionality.

A request for presentation of secure data on a second user device may be received (operation 53). The second user device may not be communicably coupled to the AD. For example, the second user device may reside on the same network as the first user device and not have access outside the network (e.g., which the first user device may access devices and/or information outside the network). The first user device may be restricted from communicating with the second user device. Thus, the first user device may request facilitation of the presentation of secure data on the second user device from the AD.

Instructions may be generated based at least partially on the received request for presentation of secure data (operation 54). The instructions may include information about how to access the secure data (e.g., appropriately formatted requests for a SDA and/or second user device), an identification of a HIP, and/or a key to be provided for validation of the request (e.g., by the HIP). The AD utilize a previously established relationship with a HIP to determine the key to be included in the instructions.

The instructions may be transmitted from the AD to the first user device (operation 55). For example, the AD may transmit a message to the first user device, in response to receiving a request for presentation of the secure data, that includes the instructions. Since the AD may not be able to initiate communications directly with the HIP, the AD may transmit instructions via the first user device to the HIP. The instructions may be transmitted by the first user device to the HIP to allow presentation of the secure data on a second user device. The HIP may transmit the instructions or portions thereof to all the secure data to be retrieved and presented on a presentation interface of the second user device.

Process 50 may be implemented by various systems, such as system 100. In addition, various operations may be added, deleted, and/or modified. In some implementations, process 50 may be performed in combination with other processes or portions thereof, such as process 20, 30 and/or 40. For example, the process may be implemented in a medical environment (e.g., hospital, clinic, practice group, and/or other medical associations). The secure data may be secure medical data, such as diagnostic image(s), billing information, patient information, electronic medical record(s), and/or any other appropriate medical data. For example, the secure data may be data available through RIS (radiological information system), BRIS (breast specific radiological information system), and/or PACS (picture archiving and communication system) and/or other medical data viewing software. The process may be performed to maintain security of the data (e.g., in compliance with government, industry, and/or company standards and/or regulations). In some implementations, at least a portion of the secure data may include unsecure data.

In some implementations, a selection from the first user device may be received by the AD via the generated interface. The AD may determine the secure data associated (e.g., patient records associated with a selected patient, diagnostic images associated with a selected patient, seismological test results associated with a selected location, topographical maps associated with a selected location, and/or other associations) with the generated interface and/or received selection. The AD may generate instructions to allow presentation of secure data on the second user device at least partially based on the determination of associated secure data.

Figure 6:
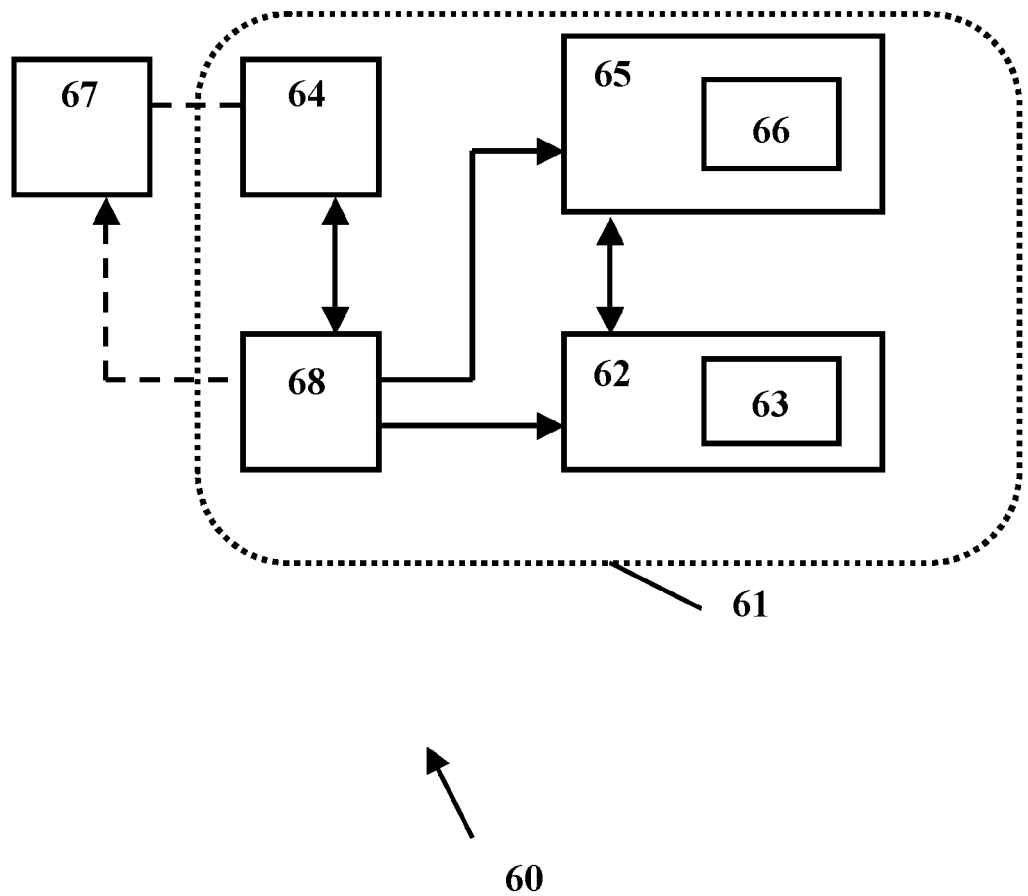
FIG. 6 illustrates an implementation of an example system that includes secure medical data.

In some implementations, a system that facilitates secure transactions may be utilized in the medical industry. For example, hospital(s), clinic(s), medical practice(s), laboratories, and/or any other medical industry may utilize a system for facilitating secure transactions. At least some medical data may be store securely. Government, industry, and/or medical facility regulations and/or standards may dictate that some medical data be secure medical data (e.g., access to the medical data may be restricted). FIG. 6 illustrates an example system 60 for facilitating secure medical data transactions. As illustrated, a network 61 may be utilized. Access to and/or from the network 61 may be regulated.

FIG. 6 illustrates an implementation of an example system 60 for facilitating communication. System 60 includes a network A 61. The network A 61 may be a local area network, in some implementations. Access to the network A 61 may be restricted.

The network A 61 may include an SDA, such as a medical data system ("medical SDA") 62. The medical SDA may reside in a different network, in some implementations. The medical SDA may be restricted from accessing the Internet and/or portions thereof. Access to the medical SDA by a first user device A 64 may be restricted. The medical SDA may be coupled to the second user device B 65. The medical SDA may include restrictions in communication protocols, such as a lack of support for HTTP.

The medical SDA may store data, such as secure data (e.g., data that should be secured under regulations such as Health Insurance Portability and Accountability Act "HIPAA"; patient information, electronic medical records, insurance information, billing information, diagnostic imaging, and/or other data) and/or unsecure data (e.g., hospital map). The secure data may be any data to which access is restricted. In some implementations, the secure data may include electronic medical records including patient information and/or test results (e.g., blood test results, biopsy results, and/or diagnostic imaging such as x-rays, CAT scans, radiographs, and/or computed tomography [CT] scans). The medical SDA 62 may include any appropriate server and/or any appropriate repository in which the data (e.g., medical data) is stored. As illustrated, medical data 63 may be stored in a memory of the medical SDA 62.

The network A 61 may include user device(s), such as a first user device A 64 and a second user device B 65. The user devices may include similar or different types of devices, such as laptops, desktop computer, tablet computers, and/or smart phones. The user device(s) may include a processor, a memory, a communication interface, and a presentation interface. The processor may include a programmable logic device, a microprocessor, or any other appropriate device for manipulating information in a logical manner and memory may include any appropriate form(s) of volatile and/or nonvolatile memory, such as a repository. The communication interface may allow the user device(s) to communicate with other computers and/or repositories via a network. The communication interface of a user device may communicate with other computers and/or repositories, such as the web server and/or HIP server, via one or more network protocols (e.g., TCP/IP, Wi-Fi, 802.11g, 802.11n, IR or Bluetooth). A presentation interface may present data on the user device to a user, such as via a monitor and speakers.

The user devices 64, 65 may have similar or different access to other computers on the network A 61 and/or the Internet. As illustrated, first user device A 64 resides in network A 61 and has access outside network A (e.g., to the Internet). The first user device A 64 may include restrictions in communication protocols, such as being limited exclusively to HTTP for communication. The first user device A may be restricted from accessing the medical SDA 62 and/or the second user device B 65. The first user device A 64 may be restricted to being able to initiate communication, but not accept incoming communication, in some implementations. In some implementations, the first user device A 64 may be restricted, with respect to initiating communications, to initiate communication only in predetermined protocols, such as HTTP, in some implementations.

The second user device B 65 may reside in network A 61, as illustrated, and/or may reside in a different network to which the HIP server is configured to access. The second user device B 65 may be restricted from accessing the Internet and/or portions thereof. Access to the second user device B 65 from the first user device A 64 may be restricted. The first user device B may be coupled to the medical SDA 62. The user device B 65 may include restrictions in the communication protocols, such as lack of support for HTTP.

In some implementations, a user may utilize at least one of the user devices for a different application than another user device. For example, the first user device A 64 may include a web-based application and/or module of the web-based application. The web-based application, such as a management web module, may facilitate an operation, such as providing diagnoses. The management module on the AD (e.g., a web server) and the management web module on the first user device A may communicate and/or perform various operations together and/or separately. For example, U.S. Provisional Patent Application No. 61/666,492 filed on Jun. 29, 2012; U.S. Provisional Patent Application No. 61/674,773 filed on Jul. 23, 2012; U.S. Nonprovisional patent application Ser. No. 13/907,167 filed on May 31, 2013; and U.S. Nonprovisional patent application Ser. No. 13/907,304 filed on May 31, 2013, all of which are incorporated by reference as if fully included herein, describe examples of a management web module and management module that facilitates providing diagnoses and/or billing for diagnoses. The first user device may access interfaces to providing diagnoses and/or billing for diagnoses via the Internet. The interfaces may be generated by a web server, such as a SDA and/or a medical SDA.

As illustrated the second user device B 65 may include one or more medical data presentation module(s) 66. The medical data presentation module(s) 66 may allow presentation of medical data, such as diagnostic images and/or electronic medical records. The medical data presentation module(s) 66 may request secure data from the medical SDA in which the secure data is stored. For example, the second user device may include modules such as RIS (radiological information system), BRIS (breast specific radiological information system), and/or PACS (picture archiving and communication system).

The system 60 may include a HIP 68 (e.g., a server) that resides in network A 61. The HIP 68 and the first user device A 64 may reside in the same network. The HIP 68, in some implementations, may be communicably coupled to devices, such as user devices (e.g., first user device A 64 and second user device B 65) and the medical SDA 62. If a second user device B 65) and/or medical SDA 62 reside in a different network, then the HIP server may include a communication interface (e.g., including a router of network A 61). The HIP server may be able to initiate outgoing communication to the Internet but not accept incoming communication from the Internet, in some implementations.

In some implementations, the HIP 68 may include a module stored in a memory of a computer or other device in the Network A 61. The module may perform various operations such as retrieving communication protocols for communication with other devices in network A 61, including the first user device A 64, and/or the AD 67 (e.g., web server). The module may receive requests, such as from the first user device A 64, for data stored in the medical data system and transmit a request to the medical SDA 62 for the data to be transmitted to the HIP 68 and/or another device (e.g., second user device B 65). The HIP 68 may be able to access computers and/or networks outside network A 61. For example, the HIP 68 may be able to access the AD 67 through the Internet or access other networks which may host the second user device B 65 and/or medical SDA 62. The HIP 68 may be restricted from receiving incoming communications from outside the network on which it resides, in some implementations. For example, by restricting the receipt of incoming communications (e.g., from AD 67), communications with the medical SDA and/or the second user device B 65 may be allowed (e.g., by government, industry, and/or company standards and/or regulations).

The system 60 may include an AD 67, such as a web server. The AD 67 may generate interfaces, which are accessed via a website by the first user device A 65. The AD 67 may include any appropriate server, such as a web server. The AD 67 may include a processor that executes instructions and manipulates data to perform operations of the AD 67 and a memory. The memory of the AD 67 may include a repository of data. For example, the data may include image icons, coding (e.g., diagnostic coding, medical billing coding), data related to medical diagnoses, uniform/common terminology for diagnoses, tracking information related to medical diagnoses, tracking information related to users, medical references, and/or other information. The AD 67 may receive and/or respond to incoming communication from the Internet and/or other networks, but the web server may not be able to initiate the communication with at least some portions of the system (e.g., HIP 68), in some implementations.

The memory of the AD 67 may store various software modules. For example, management modules may generate interfaces on a user device. Management module of the AD 67 may be capable of providing instructions to allow communicating with medical data systems and devices, such as commercially available software for medical image viewing and/or electronic medical record software. In some implementations, the management module may be restricted from initiating the communication due to the restricted Internet/web access of the devices that run this software, as illustrated. The memory of the AD 67 may include any appropriate type of memory.

A communication interface of the AD 67 may allow the AD to communicate with other repositories and/or user devices (e.g., other devices in network A 61). The communication interface may transmit data from AD 67 and/or received data from coupled repositories and/or other user devices via network protocols (e.g., TCP/IP, HTTP, Bluetooth, and/or Wi-Fi) and/or a bus (e.g., serial, parallel, USB, and/or FireWire).

Although not illustrated, additional repositories may be coupled to AD and/or the system via network A and/or other networks. Data useful to the system may be stored in repositories in a plurality of locations such as in a memory of the HIP 68, the AD 67 (e.g., web server), the user devices (e.g., first user device A 64 and/or second user device B 65), the medical SDA 62, and/or remotely. Remote, as used herein, means any component, object, value, variable, and/or data and/or data schema that is not directly processable, accessible, or otherwise capable of communicating with a device (e.g., a server). Indeed, remote data is merely in terms of a specific server. The remote data may be remote to a specific server but may be local to another server or even physically resident on a client (e.g., user device) coupled to the server.

Although FIG. 6 illustrates an implementation of a system 60, other implementations may be utilized as appropriate. For example, one or more of the described components and/or operations associated with FIGS. 1-5 may be utilized in combination with and/or in replacement of portions of the components of FIG. 6. In some implementations, the system 60 may include other components, such as repositories that store electronic medical data and/or diagnostic images. The repository may reside in the same network as the medical SDA 67 and/or remote to the medical SDA. The medical SDA may retrieve the data from the remote repository when requested, in some implementations.

In some implementations, a system, such as system 100 and/or 60, may be utilized in medical environment, such as a hospital. The hospital may store secure data such as patient information and/or test results in a medical SDA. For example, testing laboratories and/or imaging equipment may transmit test results to the medical SDA. In some implementations, hospital staff may enter and/or transmit patient information to the medical SDA. The medical SDA may not be accessible by all users, and/or access to the data by user devices may be restricted based on properties of the user devices (e.g., access to the Internet, user information, etc.). Access to the medical SDA and/or secure data on the medical SDA may be maintained to satisfy government, industry, and/or company regulations and/or standards.

A user, such as a doctor in the hospital, may have more than one user device. A first user device that is coupled to a web server, such as an AD, may facilitate various operations that the user would like to perform. For example, the user may access a web module on the first user device that communicates with an AD to facilitate providing diagnoses and/or billing information. The first user device may be restricted from accessing the medical SDA, in some implementations.

A second user device may be coupled to the medical SDA and may display data (e.g., secure medical data) from the medical SDA, such as test images (e.g., x-rays) and/or electronic medical records. The user may access on the second user device the secure data that the user may be restricted from accessing on the first user device. For example, the user may view test images (e.g., CAT scans) on a presentation interface of the second user device and may utilize a web module on the first user device to enter and/or facilitate entry of a diagnosis related to the viewed test images.

In various implementations, the described systems and processes may perform various operations to facilitate retrieval of the appropriate data from the medical system. Thus, in some implementations, even though the first user device is restricted from directly communicating with the second user device and/or the medical SDA, the appropriate data may be retrieved and/or presented to the user (e.g., on a second user device).

Figure 7:
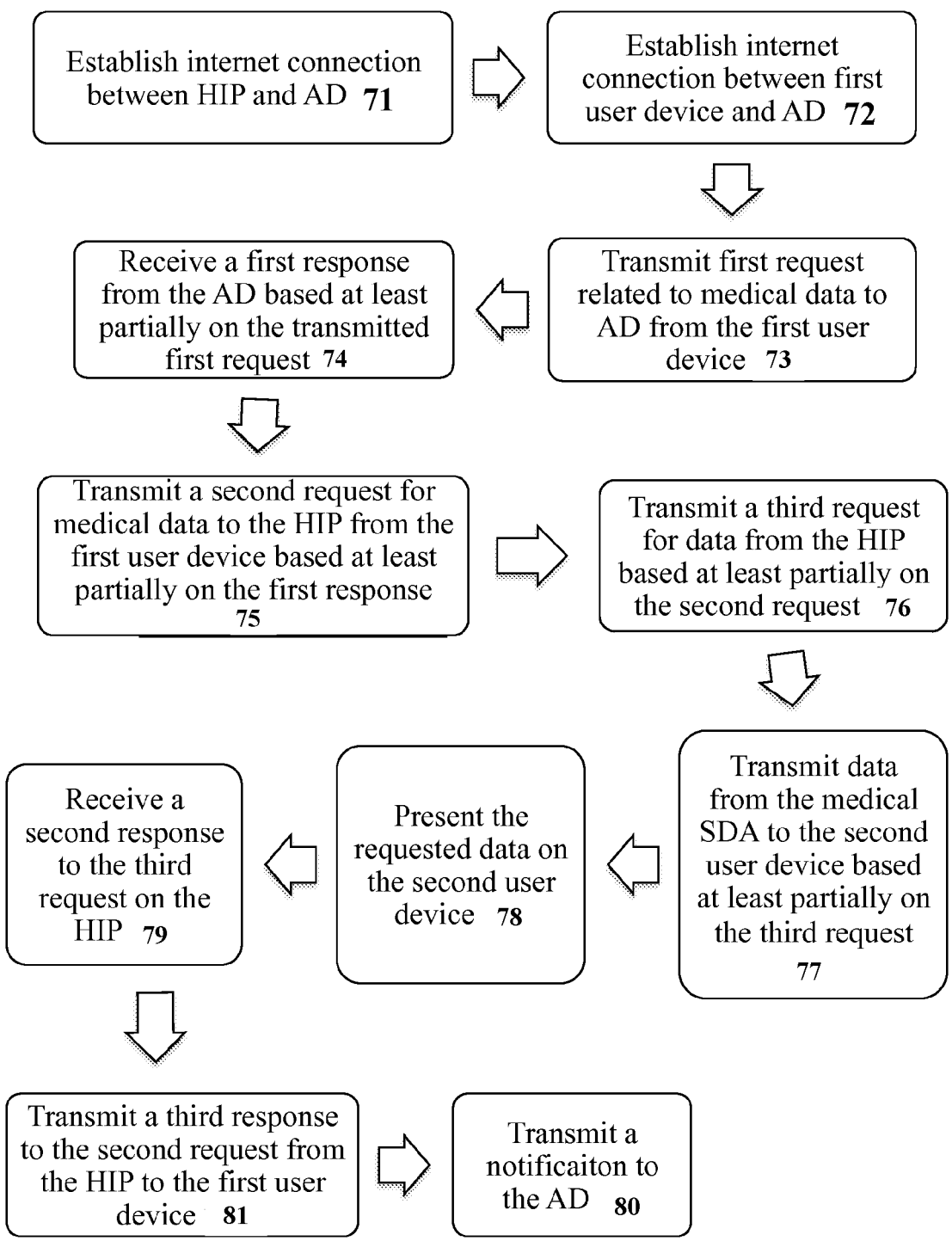
FIG. 7 illustrates an implementation of an example process for transmitting secure data in systems.
Figure 8:
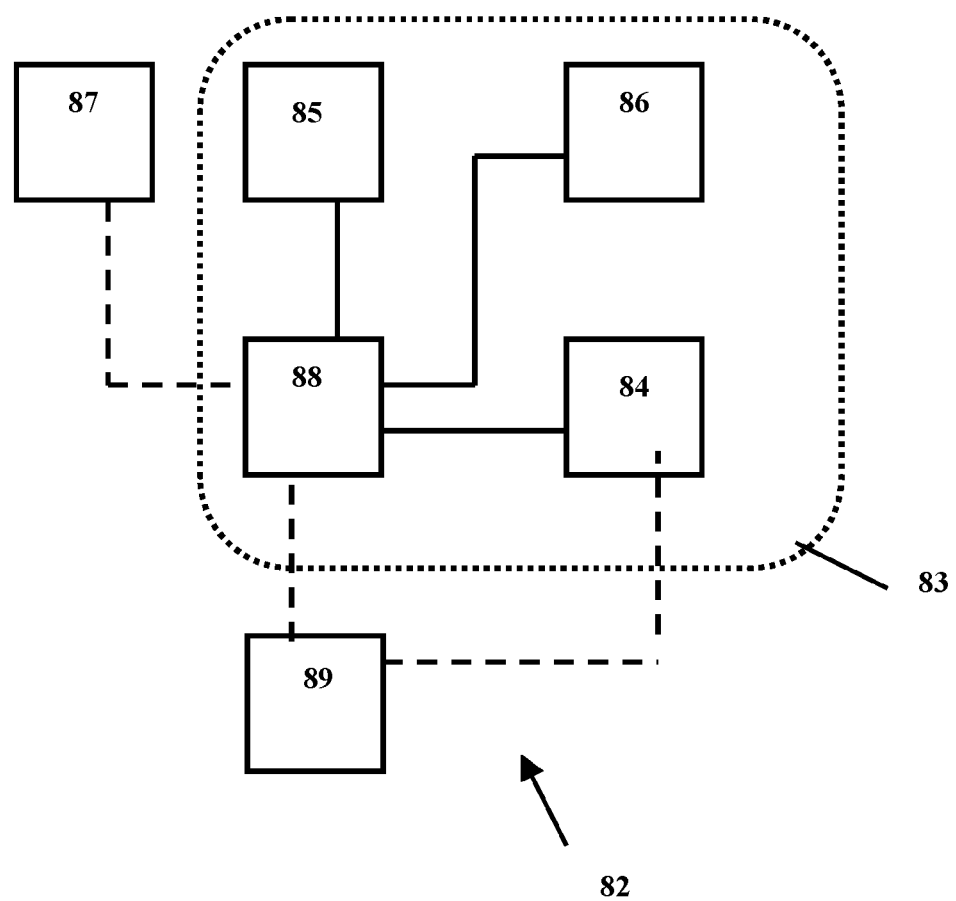
FIG. 8 illustrates an implementation of an example system for allowing access to devices in a network.

FIG. 7 illustrates an implementation of an example process 70 for facilitating communication in systems, such as system 100 illustrated in FIG. 1 and/or system 60 illustrated in FIG. 6. Although the process 70 may be implemented in a variety of facilities and with respect to any data, the process is described with respect to the above described hospital facility that includes a doctor with two user devices.

A user, such as a doctor, may work in a facility, such as a hospital. The doctor may be a radiologist assigned to perform various operations, such as provide diagnoses for patients and/or provide billing information. To perform at least a part of these assigned operations, the user may request to view data from the medical data system on the second user device. The data may be secure data (e.g., to protect patient privacy). For example, to provide diagnoses, the user may need to view one or more test images. In some implementations, to provide billing information, the user may need to access secure data, such as patient insurance information. Since the user may be restricted from accessing the secure data from the medical SDA through the first user device, the first user device may communicate with the HIP to have data presented to the user (e.g., via a second user device).

An Internet connection may be established between the HIP and the AD (operation 71) and an Internet connection may be established between the first user device and the AD (operation 72). For example, the user may access a module (e.g., for providing diagnoses) on the first user device to provide a diagnosis for a first patient. The user may access the module via a website and the first user device may log in and/or automatically provide user information to the web server. The module on the first user device may communicate user information to the AD (e.g., web server) to establish a connection between the first user device and the AD. In some implementations, the HIP may establish communication with the AD, independent of the user's access to the module on the first user device. For example, the HIP may transmit a notification to the AD (e.g., to establish a key with the AD). The HIP may be restricted from receiving information directly from the AD.

A first request related to medical data may be transmitted from the first user device to the AD (operation 73). For example, the user may request to provide a diagnosis for a patient and/or to obtain access to images related to the first patient to provide a diagnosis for the first patient through the management web module on the first user device. Thus, the management web module may transmit a request to the AD based on the user request.

A first response from the AD based at least partially on the transmitted first request may be received (operation 74). For example, the first response may include a graphical user interface (GUI) and/or instructions to allow generating a GUI to facilitate entry of a diagnosis of the first patient by the user. The response may include instructions that the web module on the user's device should transmit to the HIP server. The instructions may relate to the data associated with the first patient that is stored in the medical data system. Since the AD and the first user device are not communicably coupled to the medical SDA, in some implementations, the instructions may be transmitted to the HIP and the HIP may facilitate access to the data. In some implementations, the AD may communicate directly with the HIP.

A second request for medical data may be transmitted to the HIP from first user device based at least partially on the first response (operation 75). The first user device may receive the first response and generate a second request based on the first response. For example, the first user device may extract the instructions to allow the HIP from the first response and send the extracted instructions from the first response to the HIP as the second request. The first user device, in some implementations, may not be able to process the instructions to allow the HIP server (e.g., the instructions may be written in HL7 and/or the instructions may utilize transmission in protocols other than HTTP and the first user device or portions there of may be restricted to communication in HTTP) but may be able to pass them on directly to the HIP server for execution.

A third request for data may be transmitted from the HIP based at least partially on the second request (operation 76). For example, the third request may be to the medical SDA and/or to the second user device, as appropriate. The HIP server may receive the second request and generate a third request based at least partially on the second request. For example, a request for access to the data in the medical SDA associated with the first patient may be sent from the HIP to the medical SDA based on the instructions to allow access generated by the AD in the first response (e.g., on which the second request and third request are based).

Data may be transmitted from the medical SDA to the second user device based at least partially on the third request (operation 77). The medical SDA may receive the request for access to the data and transmit the requested data based on the third request. For example, the request may instruct the medical SDA to transmit the data requested to the second user device, which is coupled to the medical SDA. In some implementations, if the third request was sent directly to the second user device, the second user device may receive a third request and, based at least partially on the third request, receive the medical data from the medical SDA.

The requested data may be presented on the second user device (operation 78). An interface may be generated on the second user device to display the data to the user. For example, the second user device may present the images (e.g., the data requested from the medical data system) requested by the user (e.g., doctor) who is providing a diagnosis for the first patient through the web module at least partially residing on the first computer. In some implementations, the second user device may include a module (e.g., RIS and/or PACS) that allows the medical data to be presented on a presentation interface of the second user device.

A second response to the third request may be received by the HIP (operation 79). For example, after the receiver of the third request (e.g., the medical SDA or the second user device) performs operation 78 based at least partially on the third request, the receiver may respond to the HIP server with a status notification. For example, if the requested data fails to be presented on the second user device, then an error notification may be transmitted to the HIP and/or the first user device (e.g., indirectly via the HIP). If the requested data is presented on the second user device, then a success notification may be transmitted to the HIP and/or the first user device (e.g., indirectly via the HIP). The HIP may notify the AD, with which it has an established connection from operation 71, of the response the HIP server received in operation 79.

Process 70 may be implemented by various systems, such as system 100 and/or system 60. In addition, various operations may be added, deleted, and/or modified. In some implementations, process 70 may be performed in combination with other processes, such as process 20, 30, 40, and/or 50. For example, the process may be repeated as the web module on the first user device communicates with the AD (e.g., web server) and requests patient information. In some implementations, a user may transmit a report (e.g., diagnosis information and/or billing) using the first user device via the interface generated by the AD. The AD may then transmit the report to one or more devices. For example, the AD may email the report or the availability of a report to a referring physician and/or a patient. The AD may indirectly transmit a request for storage on the medical SDA (e.g., since the AD does not have access to and/or may be restricted from initiating communications with the medical SDA). The AD may transmit storage instructions to the first user device. The storage instructions may include the report for storage, a key for the HIP, and/or other information regarding instructions to allow the storage of the report. The first user device may transmit the storage instructions to the HIP, which transmits the storage instructions to the medical SDA. The medical SDA may process the storage instructions and store the report.

In some implementations, the HIP may be utilized in combination with one or more applications at least partially residing outside the network in which the HIP resides, such as web-based applications. Utilizing the HIP may reduce maintenance issues, feasibility, and/or security issues (e.g., when compared with VPN connections).

The system 82 may include a network A 83. The system 82 may include a first device 84 that runs a third party web-based application. For example, the first device 84 may be allowed to access networks and/or devices outside the network on which the first device 84 resides. For example, the first device 84 may be allowed to access the Internet and be able to access web-based interfaces generated for presentation.

The system 82 may include one or more second devices 85, 86, such as an SDA, may reside in the network A 83. The second devices 85, 86 may be restricted from accessing data and/or devices on networks outside the network on which the second devices reside (e.g., outside network A 83).

The system 82 may include an AD 87. The AD may reside outside the network on which the first device 84 and/or second devices 85, 86 reside. For example, the AD may be a web server. The AD 87 may be restricted from initiating communications with the second devices 85, 86.

The system 82 may include a HIP 88. The HIP 88 may reside on the same network as the first devices 84 and/or the second devices 85, 86. Access to the HIP 88 may be restricted. For example, computers outside the network on which the HIP 88 resides may be inhibited from initiating communications with the HIP.

In some implementations, the HIP 88 may establish a connection with the AD 87. For example, the HIP 88 may log into the AD 87. The AD 87 may transmit a message to the HIP 88 that includes information such as what devices are connected to other devices and/or the system, from which devices to receive communications, information regarding security credentials to utilize for validation, and/or any other appropriate data. The AD 87 may be able to transmit the message to the HIP 88 since the HIP initiated communications with the AD.

The message from the AD 87 may include information regarding establishing a connection with a third party web server 89. For example, the message may include security credentials (e.g., a key) for establishing a connection between the HIP 88 and the third party web server 89. The message may indicate which devices residing on the network A 83 to receive communications from.

The HIP 88 may establish a connection with the third party web server 89 based at least partially on the message received from the AD 87. The HIP 88 may establish a security credential (e.g., a key) with the third party web server 89 (e.g., by transmitting a key to the third party web server). By establishing a security credential with the third party web server 89, the third party web server 89 may utilize the established security credential when communicating with and/or transmitting information via the first device 84.

A user may utilize the first device 84 to access the interfaces generated by the third party web server 89. The user may provide user information (e.g., user name, password, security credential) to the first device 84 to access the first device and/or interfaces generated by the third party web server 89. The user may perform one or more operations (e.g., provide selections, provide analysis, view information, and/or any other appropriate operation) using the generated interfaces via the first device 84. The first device 84 may communicate with the third party web server 89 via HTTP and/or HTTPS requests and/or responses.

One or more operations allowed by the third party web server 89 may utilize information stored on and/or operations performed by second devices 85, 86. For example, the third party web server 89 may request presentation of data, such as diagnostic images, and/or request an analysis of a test (e.g., automated breast density analysis) which may be accessible using second device(s). Thus, since the third party web server 89 may be restricted from directly communicating with the second devices (e.g., since the second devices may not accept incoming communications from devices outside the network on which the second devices resides). The third party web server 89 may transmit a request for the operation (e.g., presentation of data and/or performance of an operation) to the first device 84. The request may include a key.

The first device 84 may transmit the request or portions thereof to the HIP 88. The HIP 88 may determine whether to allow the further transmission of the request based at least partially on the key (e.g., the key may be compared to the key established with one or more devices, such as the AD 87 and/or the third party web server 89 and if the key is the same as the established key, further transmission may be allowed). If a determination is made to allow further transmission, the HIP may transmit the request for the operation to the appropriate second device. If a determination is made to restrict further transmission (e.g., a key provided with the request is not the same as an established key), then further transmission may not be allowed by the HIP. The HIP may transmit a notification of failure to the first device 84 and/or the third party web server 89. In some implementations, after transmission of the request for the operation by the second device, the HIP may transmit a response to the first device. The response may include results of the operation (e.g., presentation of data on a device that is capable of presenting the data).

In some implementations, the third party web server may not be coupled to a first device, which resides in the network A and which operates a web module associated with the third party web server. During operations of the system, the third party web server may request operations from one or more second devices, which reside on network A. Since the third party web server does not reside on the same network as the second devices, the second devices may not accept incoming communications from the third party web server. Since a first device which is used to communicate with the third party web server and/or in which a web module associated with the third party web server resides is not included in the network A, the third party web server may transmit instructions to the HIP. To allow the HIP to receive instructions from the third party web server, when the HIP establishes a connection with the third party web server, the connection is maintained (e.g., kept open). Thus, the third party web server may transmit requests for operations to be performed by the second device(s) via the HIP through the maintained connection. The HIP may receive the requests and transmit at least a portion of the request to the appropriate second device. The HIP may validate a key provided with the request (e.g., by comparing the key to an established key) prior to allowing the further transmission of the request or portions thereof. The second device may perform the operation based on the request. In some implementations, the HIP may transmit a notification to the third party web server. The notification may include the results of the requested operations performed by the second device and/or results of validation (e.g., error and/or successful transmission).

In some implementations, the third party web server may include systems that include PACS, BRIS, RIS, electronic medical record, billing, scheduling, and/or other appropriate systems. In some implementations, the HIP may replace one or more VPNs utilized in a network. The HIP may allow third party access to systems residing on a secure network.

In some implementations, the HIP may reside on any appropriate device. The HIP may reside on non-web based third party servers and utilized to communicate with devices that reside on a network.

In some implementations, a user may utilize at least one of the user devices for a different application than another user device. For example, the user device may include a web-based application and/or module of the web-based application. The web-based application, such as a management web module, may facilitate an operation, such as providing diagnoses. The management module on the AD (e.g., a web server) and the management web module on the first user device A may communicate and/or perform various operations together and/or separately. The first user device may access interfaces to providing diagnoses and/or billing for diagnoses via the Internet. The interfaces may be generated by a web server, such as a SDA and/or a medical SDA.

Records and/or test results are often electronically presented to users. Providing systems and processes to allow electronic entry and/or formation of the analysis of the test results may improve turnaround time, accuracy, and/or uniformity of analysis reports for aggregation of results. In various implementations, users may utilize an image-based analytic (IMA) system to provide and/or formulate analyses based on test results. The IMA system may include image icon(s) and other icon(s). Selection of the image icon(s) and/or the other icon(s) may allow the IMA system to generate analyses reports. In some implementations, a user may view test results and provide an analysis of the test results via selection of one or more image icons on a graphical user interface (GUI) generated by the IMA system. The IMA system may generate one or more reports based the icon(s) selected by the user. In various implementations, the IMA system may allow image-based research. The IMA system may be used in a variety of environments, such as medical environments, structural analyses, geotechnical analysis, and/or other environments.

In some implementations, a user, in a medical environment, may access an IMA such as an image-based medical diagnostic (IMD) system. A user, such as a physician, may view medical images such as patient test results (e.g., radiographs, ultrasound scans, MRI scans, nuclear medicine scans, and/or computed tomography [CT] scans) and formulate a diagnosis based on the medical images. For example, a radiologist may view and analyze CT scans to determine if a benign mass exists and/or aneurism is present.

An image based medical diagnostic system (IMD system) may generate graphical user interface(s) (GUI) that allow selection of image icon(s) on the GUI(s) to automatically prepare diagnoses of test results, such as patient test results that include one or more medical images. The user may research and/or obtain further information about image icons, and thus diagnoses, through the IMD system. The IMD system may utilize a plurality of image icons in various GUIs.

An image icon is an icon that includes at least a portion of a photographic image. A photographic image may include an image created by a lens or a sensor such as an image created on a photographic film or an electronic image. A photographic image may be 2D or 3D. For example, the photographic image may include medical photographic images such as photographic images obtained from MRI scans, nuclear medicine scans, CT scans, ultrasounds, and/or radiographs. The image icon may be an example, such as a typical presentation, of a diagnosis or portion thereof (e.g., a characteristic of a diagnosis). For example, the image icon may include at least one photographic image of an example of a characteristic. A characteristic may include a property, appearance, and/or other information related to one or more analyses or portions thereof, (e.g., the characteristic may be present in test results). For example, in a medical environment, a characteristic may be a medical characteristic, which describes, provides information related to, and/or differential information related to a diagnosis and/or portions thereof. The image icon may be an image of a particular characteristic of a diagnosis selected by, for example, an expert or other authority in the field. For example, the medical photographic image utilized in the image icon may be selected from a plurality of presentations of a particular characteristic and/or diagnosis from a plurality of patients (e.g., the image in the image icon is not from the test results being analyzed and/or from the other test results associated with the same patient). For example, the image icon may include a photographic medical image from a previously diagnosed presentation of a diagnosis in another patient. In various implementations, the image icons may include text. The text of the image icon may at least partially describe at least a portion of the photographic image in the image icon. For example, an image icon may include a portion of a CT scan of showing a calcification and the image icon may include text, such as "calcification". The text may overlap at least a portion of the photographic image on the image icon.

In some implementations, utilizing image icons that include photographic images, as opposed to representations and/or drawings, may facilitate use of the IMD system by a user, increase accuracy, and/or increase efficiency (e.g., by reducing time spend per selection of an image icon). For example, the user may not need to translate what a representation and/or drawing is illustrating, but rather the user may quickly view the photographic image in the image icon that may present similarly to a presentation of a characteristic in a patient test result. In some implementations, accuracy may be increase by using photographic images in image icons since obvious errors (e.g., misstrike a key and/or inadvertent selections) may be quickly apparent to a user since the photographic image of the image icon should represent the same characteristic as the user is identifying on the patient test results.

Utilizing an IMD system may allow a user, such as a radiologist or pathologist, who analyzes medical images (e.g., electronic and/or non-electronic medical images) to continue to use the right side of the brain, associated with studying images, to generate diagnoses reports related to viewed medical images (e.g., patient test results). Free-form and/or structured language reporting may be viewed as left-brain activity. Continued repetitive switching between right-brain and left-brain activity, as often occurs when physicians view images and then enter/dictate language based reports, may prematurely fatigue a user. Utilizing a graphical user interface with image icons may reduce fatigue associated with switching between right-brain and left-brain activity by allowing a user to utilize right-brain activity while selecting image icons.

In various implementations, determining a diagnosis through image icons generated in a GUI of the IMD system may increase the speed and accuracy of diagnoses provided by users. For example, a user examining a CT scan may be able to quickly identify a lesion from the image disposed on and/or that is a portion of the image icon. In some implementations, if a user suspects a first diagnosis and then selects the image icon associated with the first diagnosis, if the first diagnosis is incorrect, the user may notice that the presentation shown in the image icon is different than the presentation shown in the patient' test result. Thus, the user may notice that the first diagnosis is incorrect and re-analyze the patients test results, search for variations in presentation, request reference materials, ask a colleague for assistance, etc.

Utilizing an IMD system may allow a user to generate diagnostic reports using predetermined common terminology with other users. The use of common terminology may facilitate searching reports; aggregation of reports or outcomes; and/or conducting literature reviews of diagnoses. Common terminology use may be based, in some implementations, on government regulations, business practices, and/or industry preference.

In some implementations, greater efficiency may be found through the automatic and contemporaneous (e.g., contemporaneous with the viewing of medical images and/or with the formation of the diagnosis) generation of the diagnostic report. For example, a user may review and/or edit the report while the analyses of medical images is fresh in the user's mind. Errors due to transcription and/or voice recognition, which may be often found in dictated diagnoses reports, may be reduced and/or may be more likely to be caught (e.g., since the patient's case history is fresh in the user's mind) since the system automatically generates reports contemporaneously based on image icon selection by a user.

Figure 10:
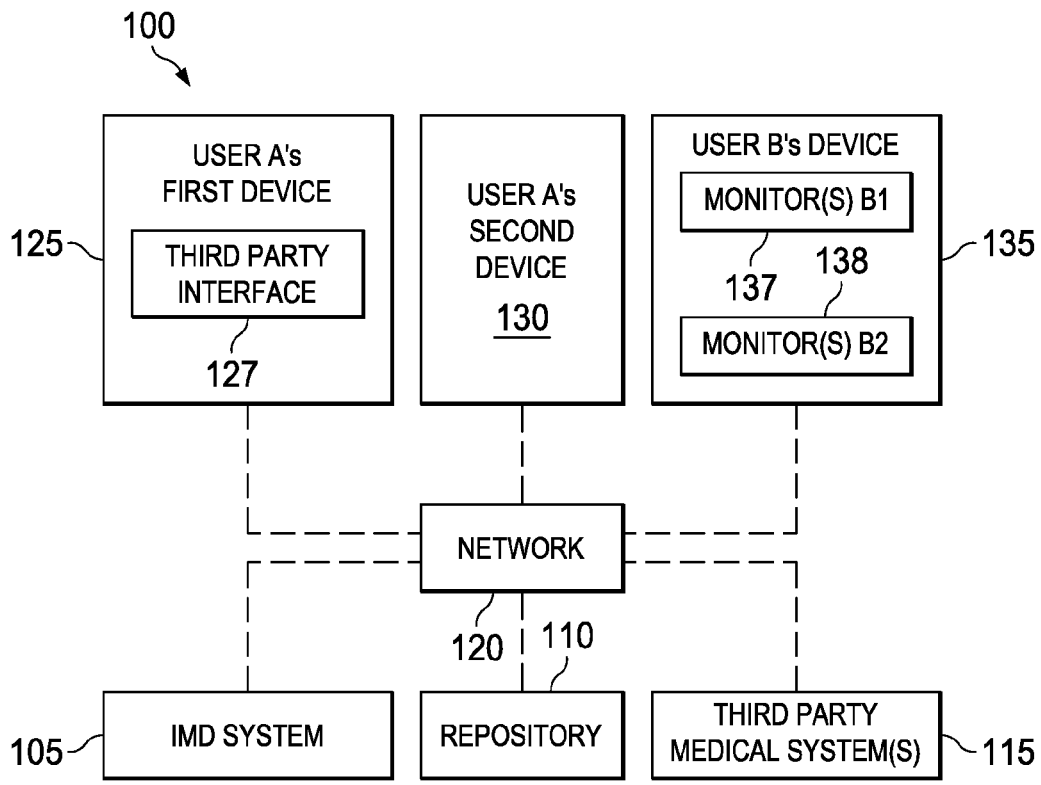
FIG. 10 illustrates an implementation of system that includes an example image based diagnostic system.

FIG. 10 illustrates a system 100 that may be utilized to provide access to the IMD system (e.g., a computer system, such as a web server). One or more users, such as user A and user B, may access the IMD system 105, a Repository 110, and/or Third Party Medical System(s) 115 through a network 120 (e.g., Internet and/or LAN). For example, medical images (e.g., patient test results) for viewing and/or analysis by a user may be viewed utilizing commercially available software (e.g., commercially available medical image viewing software, such as RIS/BRIS modules available from GE, Phillips, Siemens, McKesson; Hologic and may include MRI, CT scan, PET scan, ultrasound, and/or radiographs). The medical images may be stored in the repository 110 coupled to the user device(s) 125, 130, 135 and/or the third party medical system 115. The commercially available software may also include patient information, such as patient history and/or previous tests and/or results. (e.g., via an electronic medical record and/or appropriate commercially available viewing software). The image based diagnostic system 105 may communicate (e.g., through one or more application interfaces) with the medical image viewing software, such third party medical systems 115, to retrieve and/or display patient history and/or previous tests and/or results. The image based diagnostic system may confirm diagnosis information is being associated with the appropriate patient by communicating with the medical image viewing software. For example, when a user selects a patient for which to provide a diagnosis, the IMD system 105 may communicate with the third party system 115 to determine whether the selected patient is the same as the patient associated with the test results being presented by the third party system.

The users may each utilize one or more user devices (e.g., computer such as laptops, desktops, specialized computers, tablet computers, and/or smart phones) to access various parts of the system 100. As illustrated, user A may utilize a first device 125 and a second device 130, and user B may utilize a user device 135 that includes more than one monitor, such as Monitors B1 137 and Monitors 138.

Figure 11:
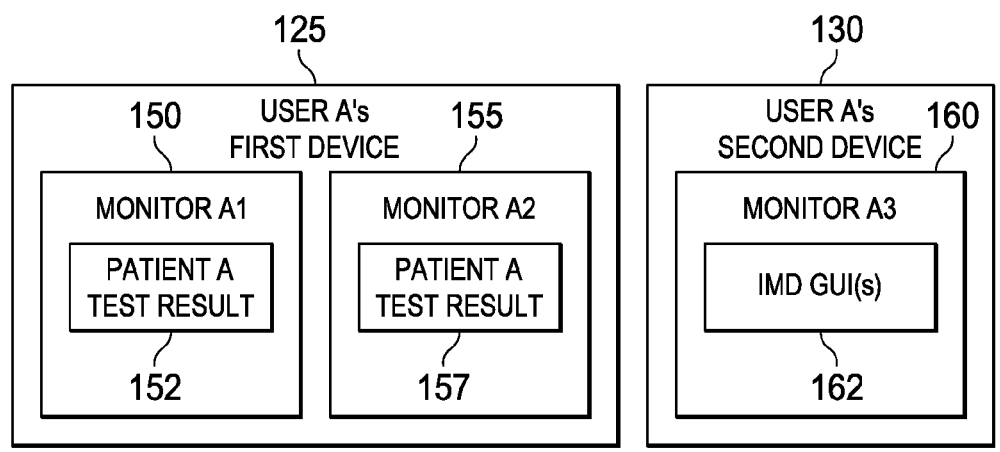
FIG. 11 illustrates an implementation of a portion of an example user device, illustrated in FIG. 10.

User(s) may access various parts of the system 100 through various user devices or portions thereof. For example, user A may access medical images, such as patient test results (e.g., CT scan(s), MRI scan(s), ultrasounds, and/or radiograph(s)), which are viewable through a third party medical system 115, via a third party interface 127, a portion of which resides on User A's first device 125. As illustrated in FIG. 11, patient A test results 152 are presented on monitor A1 150 and patient A test results 157, which may be different from test results 152, are presented on monitor A2 155 of User A's first device 125. User A may access the IMD system 105 and/or view GUIs generated by the IMD system through the User A's second device 130. As illustrated in FIG. 11, the IMD GUI(s) 162 may be presented on monitor A3 160 of User A's second device 130.

As illustrated in FIG. 10, some users, such as user B, may access various parts of the system through the same user device, such as user B device 135. For example, patient test results may be presented on Monitor(s) B1 137 and IMD GUIs may be presented on Monitors B2 138 of user B's device 135.

For example, the described system may be utilized in a radiology reading room where one or more radiologist access third party systems to view medical images, such as patient test results stored on a repository coupled to the system, and access the IMD system through which diagnoses of patient test results are provided.

FIG. 10 illustrates an implementation of an example image-based medical diagnostic (IMD) system 105. The IMD system 105 may include a server, such as a web server. The IMD server 105 may include a processor that executes instructions and manipulates data to perform operations of server and a memory. The memory may include a repository of data. Data may include various image icons, various text icons, coding (e.g., diagnostic coding, medical billing coding), data related to medical diagnoses, uniform/common terminology for diagnoses, user metrics, practice metrics, diagnosis outcome metrics, monitoring information related to government and/or industry standards, tracking information related to medical diagnoses, tracking information related to users, variations in presentations, reference materials, and/or other information. Data may include image-indexed reference materials. The image-indexed reference materials may include medical references (e.g., videos, journal articles, diagnostic references and/or images) that are correlated to and/or approximately related to image icons of the IMD system. The medical references may be expert reviewed and/or selected. Selection of an image icon may retrieve correlated data and/or references. For example, references and/or image icons may be associated by one or more associations (e.g., primarily related and/or secondarily related, such as presentations often confused for each other, similar presentations, etc.) Text based searching and/or indexes may also provide a process for searching the information in the image-indexed reference. The data and/or portions thereof may be alternatively and/or additionally stored in a repository coupled to the server.

The memory of the IMD system 105 may store various modules (e.g., diagnosis module(s), reference module(s), monitoring module(s), and/or communication module(s)). For example, interfaces, such diagnosis interfaces for receiving, presenting and/or generating medical diagnoses and/or reference interfaces for accessing image-indexed references may be generated by one or more of the modules stored in the memory. The module(s) stored in a memory of the IMD system 105 may perform one or more of the described processes. The graphical interfaces may facilitate interaction between a user and the diagnostic interface and/or reference interface. The modules may also generate communication interface coupled to the other interfaces (e.g., an interface to communicate with commercially available software for medical image viewing and/or electronic medical record software). The communication interface may accesses data upon request from other interfaces (e.g., diagnostic modules) and/or access to various forms of data. Memory may include any appropriate type of memory.

A communication interface of the IMD system 105 may allow the server of the IMD system to communicate with other repositories and/or user devices via the network 120. The communication interface of the IMD system 105 may transmit data from server and/or received data from coupled repositories and/or other user devices via network protocols (e.g., TCP/IP, Bluetooth, and/or Wi-Fi) and/or a bus (e.g., serial, parallel, USB, and/or FireWire).

Data useful to the system may be stored in repositories in a location or a plurality of locations, such as in a memory of the IMD system 105 and/or remote to the server in one or more repositories 110. For example, data, such as patient test result(s) and/or patient information may be stored in one or more of the additional repositories 110. Additional repositories 110 may be coupled to the IMD system 105 via a network 120. Diagnosis and/or reference interface may utilize the communication interface of the IMD system 105 to access data on the additional repositories 110. Remote, as used herein, means any component, object, value, variable, and/or data and/or data schema that is not directly processable, accessible, or otherwise capable of communicating with server. Indeed, remote data is merely in terms of IMD server—in other words, the remote data is typically remote to IMD server but may be local to server or even physically resident on a client (e.g., user device) coupled to the server.

The user devices 125, 130, 135 may be clients of the IMD system 105. For example, clients, such as user A first device 125, user A second device 130, and/or user B device 135, may allow a user, such as a radiologist, to access a server and/or interfaces stored on a memory of the IMD system 105. In some implementations, interface(s) of the IMD system 105 and/or portions thereof may be stored on a user device 125, 130, 135. Portions of the interface(s) stored on the user device 125, 130, 135 may be updated and/or altered by updates pushed from the IMD server (e.g., the IMD server may transmit an update to the user device). A user device 125, 130, 135 may be a computer server such as a personal computer, a laptop, a personal digital assistant, a smart phone, tablet or any computer system appropriate for communicating with the IMD system. In some implementations, user(s) may utilized more than one type of user device (e.g., a desktop and a tablet computer). The user device(s) may include a processor, a memory, a communication interface, and a presentation interface. The processor of a user device may include a programmable logic device, a microprocessor, or any other appropriate device for manipulating information in a logical manner and memory may include any appropriate form(s) of volatile and/or nonvolatile memory, such as a repository. The communication interface of a user device may allow the user device(s) to communication to other computers and/or repositories via a network. The communication interface of a user device may communicate with the IMD server via one or more network protocols (e.g., TCP/IP, Wi-Fi, 802.11g, 802.11n, IR or Bluetooth). A presentation interface of a user device may present data on the client to a user, such as via a monitor and speakers.

One or more graphical user interface (GUI) of the interface(s) generated by the IMD system may be displayed on a presentation interface of the user device, such as a monitor or screen, of the client. GUI may be operable to allow the user of a user device to interact with repositories and/or various interface(s). Generally, GUI provides a user with an efficient and user-friendly presentation of data provided by the IMD system. GUI includes a plurality of displays having interactive fields, such as image icons, text icons, tabs, pull-down lists, fillable fields, and editable text operated by the user. And in one example, GUI presents an explore-type interface and receives commands from the user. It should be understood that the term graphical user interface may be used in the singular or in the plural to describe one or more graphical user interfaces in each of the displays of a particular graphical user interface. Further, GUI contemplates any graphical user interface, such as a generic web browser, that processes information in the IMD system and/or user device and efficiently presents the information to the user. In some implementations, GUI may present a web page embedding content. The server can accept data from a user device(s) via the web browser (e.g., Microsoft Internet Explorer, Safari, or Google Chrome) and return the appropriate Hyper Text Markup Language (HTML) or eXtensible Markup Language (XML) responses.

Although FIG. 10 provides one example of an IMD server that may be used with the disclosure, the server can be implemented using computers other than servers, as well as a server pool. For example, a server may include a general-purpose personal computer (PC), a Macintosh, a workstation, a UNIX-based computer, a server computer, or any other suitable device. According to one implementation, a server may include a web server. Server may be adapted to execute any operating system including UNIX, Linux, Windows, or any other suitable operating system. In short, server may include software and/or hardware in any combination suitable to provide access to data and/or translate data to an appropriate compatible format.

Although a single processor has been described in the IMD server and/or user devices, multiple processors may be used according to particular needs, and reference to processor is meant to include multiple processors where appropriate. Processor may include a programmable logic device, a microprocessor, or any other appropriate device for manipulating information in a logical manner.

A memory of the server, memory of user device(s), and/or additional repositories may be any appropriate form of memory. For example, additional repositories may include a relational database. However, a variety of repositories may be used, such as, SQL databases, relational databases, object oriented databases, distributed databases, XML databases, and/or web server repositories. Furthermore, memory may include one or more forms of memory such as volatile memory (e.g., RAM) or nonvolatile memory, such as read-only memory (ROM), optical memory (e.g., CD, DVD, or LD), magnetic memory (e.g., hard disk drives, floppy disk drives), NAND flash memory, NOR flash memory, electrically-erasable, programmable read-only memory (EEPROM), Ferroelectric random-access memory (FeRAM), magnetoresistive random-access memory (MRAM), non-volatile random-access memory (NVRAM), non-volatile static random-access memory (nvSRAM), and/or phase-change memory (PRAM).

Although FIGS. 10 and 11 illustrate an implementation that may be utilized with the IMD system, other appropriate systems may be utilized. For example, a user may utilize a desktop computer to access third party medical systems, to view patient test results stored in a coupled repository, and/or other medical systems (e.g., hospital and/or clinic systems) and a tablet computer through which diagnoses reports are generated through the IMD system. In some implementations, a user may utilize a laptop computer coupled to monitor(s). The user may utilize a desktop computer and a smart phone, in some implementations.

Although FIGS. 10 and 11 illustrate implementations utilized with the IMD system, similar systems may be utilized with IMA systems, as appropriate. For example, a user may view test results on a first user device via a third party interface. The user may access the IMA system via a network, such as the internet and provide analyses of test results via GUIs generated by the IMA system. In addition, one or more modules of the IMA system may perform various functions similar to the modules of the IMD system and/or one or more memories may store similar data to the IMD system, as appropriate.

Figure 12A:
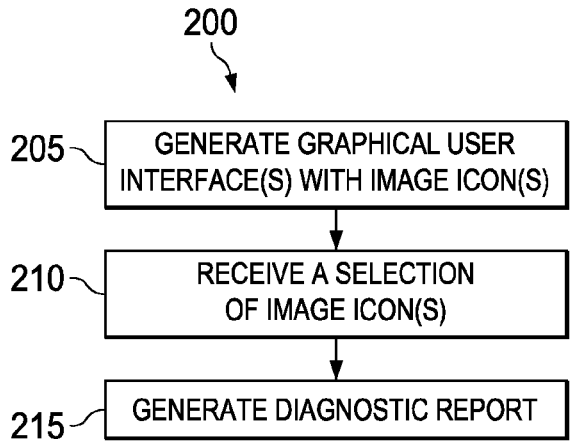
FIG. 12A illustrates an implementation of an example process performed by the IMD system.

FIG. 12A illustrates an implementation of a process 200 performed by the IMD system, such as IMD system 105 illustrated in FIG. 10, to generate diagnostic report(s). One or more GUI(s) with one or more image icons may be generated (operation 205). For example, a diagnosis module stored in a memory of the IMD system may generate the GUI(s). The GUI(s) may be generated such that one or more diagnoses may be provided by a user through the generated GUI(s). The GUI(s) may include image icons and/or text icons. The image icons may include photographic images. For example, the photographic images may be an example of a characteristic (e.g., a medical characteristic such as breast density, mass, and/or cyst). In some implementations, the photographic images selected to be included in an image icon may include images of lesion characteristics (e.g., calcification, powdery, skin, crushed, lymph node, obscured, and/or lobulated), and/or breast density. The photographic image(s) or portions thereof selected for inclusion in an image icon may be a specific presentation of a characteristic, such as a typical presentation of a characteristic, a presentation of a characteristic most commonly associated with a characteristic, etc. (e.g., as opposed to generating a graphical user interface with image icons that include images selected from the patient test results being analyzed).

A selection of one or more image icons may be received (operation 210). A user may select one or more image icons on the generated GUI(s) through a user device. For example, the user may touch an image icon on a touchscreen of a user device to select the image icon and/or use a pointing device (e.g., mouse, stylus, and/or touchpad) to select the image icon. The user device may transmit the selections of image icons to the IMD system (e.g., through a website generated by the IMD system). The IMD system may receive the selections and/or store the selections.

A diagnostic report may be generated (operation 215). The IMD system may generate the wording of the report diagnosis based on the image icons and/or text icons selected. For example, the a template of possible wording associated with one or more image icons, text icons, and/or combinations thereof may be stored in a memory coupled to the IMD system. The IMD system may determine the wording for a diagnostic report by determining the wording associated with the selected image and/or text icon(s) in the template and generating the diagnostic report based on the determined wording. The diagnostic report may automatically retrieve and/or include patient information, patient test result types being analyzed by the user, and/or one or more generated diagnoses. The diagnostic report may include other information provided by the use, such as follow-up tests recommended, comments, change from previous test results, etc. The diagnostic report may be provided through a GUI (e.g., the report GUI(s)) generated by the IMD system for presentation to a user (e.g., on presentation device of a user device).

Process 200 may be implemented by various systems, such as system 100. In addition, various operations may be added, deleted, and/or modified. For example, user credentials (e.g., user name and/or password) may be received (e.g., through a generated GUI) by the IMD system. In some implementations, the GUI may be generated based at least partially on user credentials. For example, a work-list for the user may be generated based at least partially on user credentials; the GUI may be generated based on clinic preferences, such as a specific variation of a lesion characteristic; and/or the GUI may be generated such that user preferences, such as for home page, colors, etc. are presented. In some implementations, the described process and/or operations thereof may be performed by the IMD system and/or IMA system in other environments (e.g., forensic analysis, body imaging, and/or security screening).

Figure 12B:
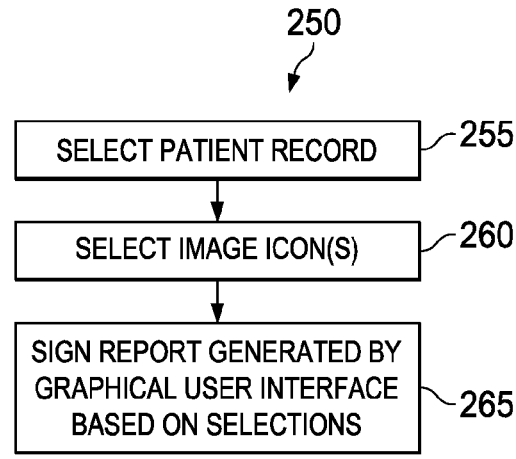
FIG. 12B illustrates an implementation of an example process for generating diagnostic report(s).

FIG. 12B illustrates an implementation of a process 250 for generating diagnostic report(s) through the IMD system. A patient record may be selected (operation 255). For example, the user may login to the IMD system via a website and the GUI generated (e.g., by the IMD system) for presentation to the user may include a work-list that includes a listing of patients which the user must evaluate. In some implementations, the work-list may include a listing of patients associated with test results for analysis by one or more users, and the user may select one or more patients from the listing to provide a diagnosis. The user may select a patient from the work-list through the GUI and the selection may be transmitted to the IMD system.

One or more image icons may be selected (operation 260). The user may view a GUI (e.g., diagnostic GUI) generated by the IMD system that includes image icons and/or text icons. The image icons and/or the text icons may be selected for inclusion in the GUI based at least partially on the type of patient test results (e.g., anatomical location of the imaging in the test result, such as breast imaging; type of machine utilized to provide the test results, such as an MRI; and/or whether the patient test results include previous diagnoses), user properties (e.g., physician specialty, group memberships, and/or compliance requirements), facility properties (e.g., type of clinic and/or hospital), and/or user preferences. The image icons may include at least a portion of a medical photographic image of an example of a medical characteristic. The text icons may include text that describes a portion of a diagnosis and/or information to be included in a diagnosis. For example, text icons may include association icons (e.g., icons that indicate a relationship between two icons such as "and", "or", and/or "versus"), coding icons (e.g., BI-RADS® Category), level of suspicion icons (e.g., benign, mild suspicion, moderate suspicion, arch distortion, high suspicion, and/or malignant mass), notation markers icons (e.g., implant, post-op, marker, negative) and/or comparison icons (e.g., gone, better, same, worse, new when compared with previous test results). The text icons may provide anatomical location information. The user may select one or more of the image icons and/or one or more of the text icons to describe the patient test results. By allowing the user to select image icons, as opposed to dictating and/or typing diagnoses, the user may more quickly and/or accurately provide a diagnosis (e.g., since the user may not have to repeatedly switch between right and left brain activities; since the user may quickly select icons rather than dictating an entire diagnosis; and/or when viewing all the options available for selection on the GUI, the user may be reminded to provide more information such as comparison to previous exam when seeing the icons on the GUI). The selected image icon(s) and/or text icon(s) may be received by the IMD system and/or stored in a memory coupled to the IMD system and/or the user device.

A report generated by the GUI based on the selected image icons may be signed (operation 265). For example, a diagnostic report (e.g., a report including at least a portion of a diagnosis), a billing report (e.g., a report including at least a portion of billing information, such as billing codes and/or insurance provider), compliance report (e.g. a report that includes information to comply with industry, association, and/or government regulations), etc. may be generated. The report may be stored in a memory coupled to the IMD system. The report may be generated based at least partially on selections of icons, industry criteria, practice group criteria, insurance requirements, governmental requirements, etc. In some implementations, a diagnostic report may be automatically generated by the IMD system based at least partially on selected image icon(s) and/or text icon(s). The diagnostic report may be presented to the user via a GUI of the IMD system. The user may review the diagnostic report and "sign" or otherwise provide approval of the diagnostic report (e.g., select an "approve" button). By allowing the user to contemporaneously view the diagnostic report (e.g., since the diagnostic report is generated by the IMD system, for example, when the user selects a report GUI and/or after receiving a selection of image icon(s)), the user may provide a more accurate and timely diagnostic report. For example, since the patient's case is fresh in the memory of the user, the accuracy of the report may be increased and/or the report may be provided in a more timely manner. In some implementations, unlike when transcription services are provided (e.g., voice recognition and/or human transcription), since the report does not need to be corrected and/or proofread, the amount of time to produce a signed report may be reduced. The signed report may be automatically transmitted, for example, to a referring physician, to a patient, to a hospital, to an insurance company, etc.

Process 250 may be implemented by various systems, such as system 100. In addition, various operations may be added, deleted, and/or modified. For example, after a user logs into the system, the user may be presented a homescreen with a listing of patients whose test results need to be analyzed. The user may select one or more of the patient records to be assigned to his/her caseload. In some implementations, the IMD system may communicate with third party medical systems to determine whether the patient record in which a diagnosis is being provided is the same as the patient record associated with the patient test results being viewed by the user. In some implementations, the described process and/or operations thereof may be performed by the IMD system and/or an IMA system in other environments (e.g., forensic analysis, body imaging, and/or security screening).

Figure 13:
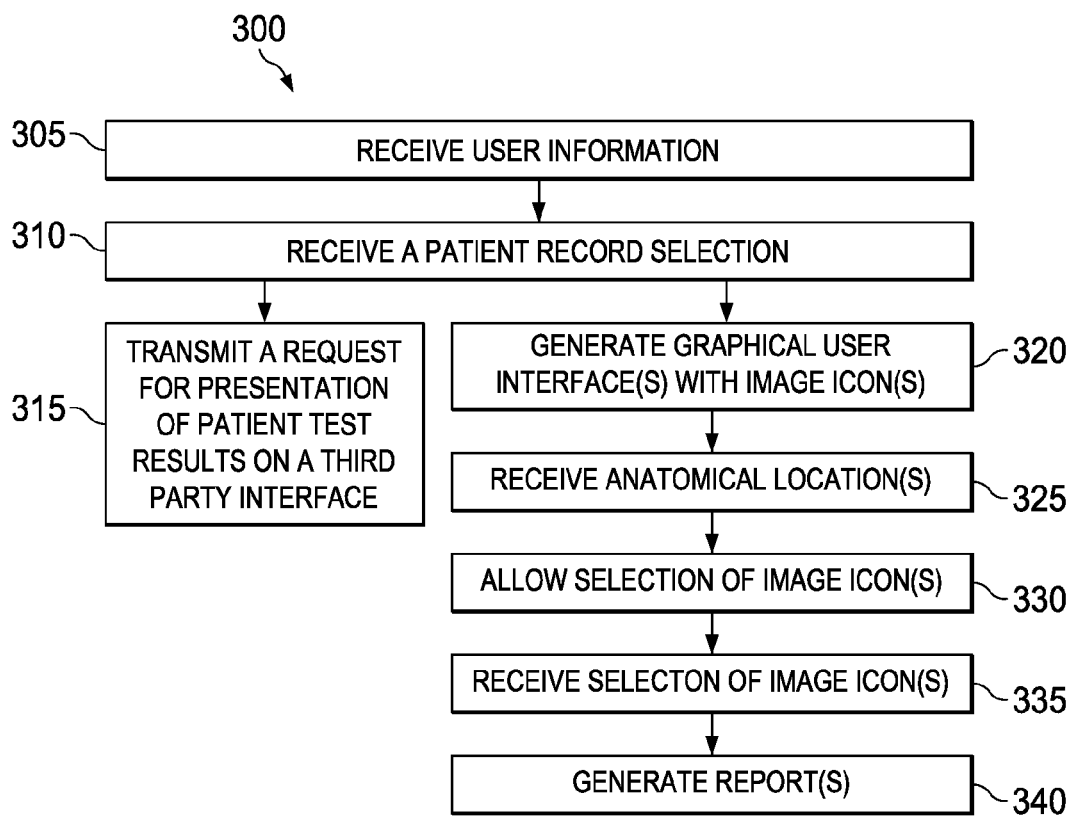
FIG. 13 illustrates an implementation of an example process for receiving diagnosis information.

In some implementations, diagnostic report(s), billing report(s), and/or other report(s) may be generated based on the image icon(s) and/or other icon(s) (e.g., text icons, such as association icons, diagnosis text icons, etc.) selected. FIG. 13 illustrates an implementation of example process 300 for receiving diagnosis information using the IMD system. User information may be received (operation 305). For example, a user may utilize a user device, such as a personal computer, to access an interface of the IMD system (e.g., through the internet) and provide credentials, such as a user name and security information (e.g., password, key code, and/or public key/private key). The IMD system may receive the user information and compare the user information to stored user information (e.g., stored in a memory coupled to the IMD system) to determine whether to allow the user access to at least portions of the IMD system. If a determination is made to allow the user access to the IMD system, then the IMD system may generate GUI(s), such as work-list GUIs, to facilitate the entry of analysis information by the user.

A patient record selection may be received (operation 310). A GUI may be generated by the IMD system to present a listing of patients. For example, a work-list for the user may be generated based at least partially on the received user information. In some implementations, the IMD system may present, via a generated GUI, a listing of patients corresponding to test results to be analyzed for a group of users (e.g., physicians on duty at a hospital, practice group, and/or specialty of a practice group, such as the mammography group of a radiology practice). The user may select a patient record and the selection may be transmitted to the IMD system.

A request for presentation of patient test results on a third party interface may be transmitted to a third party system (operation 315). The IMD system may be coupled directly or indirectly to a third party system, which allows presentation of patient test results on a user device. The IMD system may communicate with the third party system. For example, the IMD system may transmit a request to a third party system, such as a commercially available software platform for viewing patient test results (e.g., medical images, such as CT scans, MRI scans, and/or other medical images), so that test results associated with the received selection of a patient record may be retrieved (e.g., from a repository coupled to the third party system) and presented to the user via the third party system on a user device.

GUI(s) may be generated with one or more image icons (operation 320). For example, a diagnostic GUI may be generated that includes image icon(s) and text icon(s). The image icons may include breast density image icons that include at least a portion of a photographic image associated with an example of a breast density category. For example, a first breast density image icon may include a radiograph of a first breast density category (e.g., defined by industry, government, and/or insurance standards), a second breast density image icon may include a radiograph of a second breast density category, a third breast density image icon may include a radiograph of a third breast density category and fourth breast density image icon may include a radiograph of a fourth breast density image icon. In some implementations, a level of breast density may be required (e.g., by government standards) to be reported to patients and the user may select a level of breast density that corresponds to the breast density depicted in a patient test result through a breast density image icon.

An anatomical location may be received (operation 325). The user may select an anatomical location corresponding to a location on a patient in at least a portion of the patient test results. For example, a right breast, a left breast, or bilateral may be selected as an anatomical location. In some implementations, a specific location on the breast may be indicated using location indicia, such as a circle, dot, highlight, and/or other indicia. In some implementations, a representation of a breast including lymph nodes proximate the breast and/or a transverse view of a breast may be included in the GUI. An anatomical location may be provided by the user by selecting text icons, such as location icons (e.g., relative and/or anatomical location), associated with the breast images. In some implementations, a location icon may be selected via the GUI and transmitted to the IMD system.

Selection of one or more image icons may be allowed (operation 330). When an anatomical location selection is received, selection of image icon(s) may be allowed. For example, selection of image icon(s) may be restricted prior to selecting an anatomical location being selected. In some implementations, the image icon(s) may appear differently when selection is restricted than when the image icon(s) may be selected. For example, the image icon(s) may be have a grey appearance or shading when selection is restricted.

A selection of one or more image icons may be received (operation 335). For example, the user may select breast density image icon. The user may select a characteristic icon that corresponds to at least a portion of a diagnosis. For example, a characteristic icon may be a lesion-characteristic icon, such as an icon indicating calcification or cyst. The characteristic icon, such as the lesion characteristic, may include a photographic image of a visual characteristic. The visual characteristic may be at least partially included in the portion of the photographic image selected for inclusion in the characteristic icon.

Report(s) may be generated (operation 340). For example, reports, such as billing reports, diagnostic reports, compliance reports (e.g., based on metrics and/or required by facilities, such as hospitals, industry requirements, and/or government requirements). In some implementations, a diagnostic report may be generated based on image icon(s) and anatomical location(s) selected. In some implementations, a billing report may be generated based at least partially on the image icon(s), anatomical location(s) and/or diagnostic reports. The billing reports may be generated at least partially based on industry codes, such as CPT and/or ICD-9 codes, and one or more image icons, text icons, and/or combinations thereof may be associated with one or more CPT and/or ICD-9 codes such that billing reports may be generated based on selected icons. In some implementations, one or more compliance reports maybe generated based on user properties (e.g., time spent analyzing patient test results, types of test results analyzed, number of test results analyzed over a time period, and/or other metrics).

Process 300 may be implemented by various systems, such as system 100. In addition, various operations may be added, deleted, and/or modified. For example, one or more report GUI(s) may be generated to present report(s) to the user. In some implementations, the user may transmit notice of approval of the report (e.g., sign a diagnostic report and/or approve automatic transmission of a compliance report to an appropriate entity). In some implementations, the IMD system may determine whether the patient record selected is associated with the test results being presented via a third party system. If the determination is made that the selected patient record is associated with the test results being presented, then selection of one or more image icons and/or anatomical location(s) may be allowed. If the determination is made that the selected patient record is not associated with the test results being presented, then a selection of image icon(s) and/or anatomical location(s) may be restricted; a notification may be transmitted to the user; and/or a message may be transmitted to the third party system (e.g., such that the appropriate test results may be presented to the user). In some implementations, the described process and/or operations thereof may be performed by the IMD system and/or an IMA system in other environments (e.g., forensic analysis, body imaging, and/or security screening).

In some implementations, reference materials may be accessible through IMA systems, such as the IMD system. The reference materials may be accessible independently from the analytical GUIs generated by the IMA system and/or through GUIs that facilitate the receipt of analyses through the IMA system. For example, the image icons presented in a graphical user interface of an IMA system, such as the IMD system, may be correlated to reference information. For example, reference information may be indexed and/or associated with various image icons. The reference information correlated to the image icon may include images and/or text that may be relevant and/or related to the image in the image icon. The reference information may include journal articles, expert opinions, textbooks, videos, variations of presentations and/or other relevant medical reference information. During use, a user may conduct research by selecting an image icon and viewing the correlated reference information. By allowing a user to quickly access information related to a diagnosis and/or potential diagnosis while analyzing patient test results, accuracy may be increased. For example, accuracy may be increased since: research on diagnosis is quickly and easily provided through the interface; since a diagnosis can be researched without knowing key words by using image icons to search references; and/or since variations of presentations of lesions may be quickly searched to provide more accurate diagnoses. In some implementations, users may use the reference materials accessible through the IMA system to retrieve references related to image icon(s) to further study a characteristic in an image icon.

Figure 14:
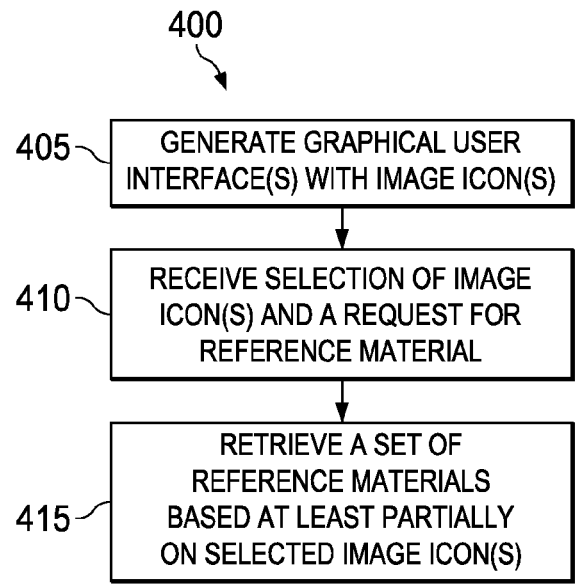
FIG. 14 illustrates an implementation of an example process for retrieving reference materials.

FIG. 14 illustrates an example process 400 for retrieving reference materials. The process 400 may be performed by systems, such as system 100. GUI(s) may be generated including one or more image icons (operation 405). For example, the IMD system may generate interfaces, such as a diagnostic GUI and/or a reference GUI. For example, the diagnostic GUI through which diagnoses may be provided, may be generated with one or more image icons and/or one or more other icons, such as text icons. In some implementations, a reference GUI may be generated that includes image and/or text icons through which reference materials related to the image icons and/or text icons may be retrieved. The GUI may include fields through which the reference materials may be searched. A user may be presented with free-form fields in the diagnosis GUI and/or reference GUI, through which keywords may be provided for a search to be executed upon by the IMD system.

A selection of one or more image icons and a request for reference material may be received (operation 410). For example, a user may double click an image icon on a GUI generated by the IMD system to request reference material associated with the image icon. In some implementations, the user may select an image icon and another icon, such as a reference text icon to request reference material related to the image icon. In some implementations, the user may select more than one image icon and an association icon (e.g., versus) to indicate a relationship among the image icons about which the user would like further information (e.g., reference materials).

A set of reference materials may be retrieved based at least partially on the selected image icon(s) (operation 415). For example, the IMD system may determine a set of reference materials to retrieve based on associations between reference materials, image icon(s), and/or text icon(s) stored in a memory coupled to the IMD system. In some implementations, the set of reference materials may include one or more levels of association, such as a primary association, a secondary association, etc. For example, an image icon may have a primary association with a set of references, such as the set of references primarily associated with the image icon may provide further information about the image icon. An image icon may have a secondary association with a set of references, such as the set of references secondarily associated with the image icon may provide additional information about the image icon (e.g., similar characteristics and/or diagnoses, commonly confused and/or related characteristics and/or diagnoses, etc.).

Process 400 may be implemented by various systems, such as system 100. In addition, various operations may be added, deleted, and/or modified. For example, the set of retrieved materials or a portion thereof (e.g., titles) may be presented to the user. The user may select one or more of the reference materials in the set and the IMD system may present the selected reference material(s) to the user via GUI(s) generated by the IMD system. In some implementations, the GUI with image icons may be generated independently of a patient, test results, and/or patient record. In some implementations, a set of references may be retrieved and recommended to a user and/or group of users (e.g., based on metrics, such as accuracy, error rates, new information, etc.). A user may access image icon-based searching of references while analyzing test results and providing a diagnosis through the IMD system. In some implementations, allowing searching of references based on image icons may be performed independently of providing diagnoses for patients. In some implementations, the described process and/or operations thereof may be performed by the IMD system and/or an IMA system in other environments (e.g., forensic analysis, body imaging, and/or security screening).

In some implementations, various metrics may be monitored, such as user information, user statistics, user group statistics, costs, diagnoses information, error rates, accuracy, outcomes, overall Receiver Operator Characteristic (ROC) curves, ROC curves relative to specific diagnoses, etc. The information may be tracked to comply with government regulations, industry regulations, licensing requirements, and/or to further research and/or educational goals.

Figure 15:
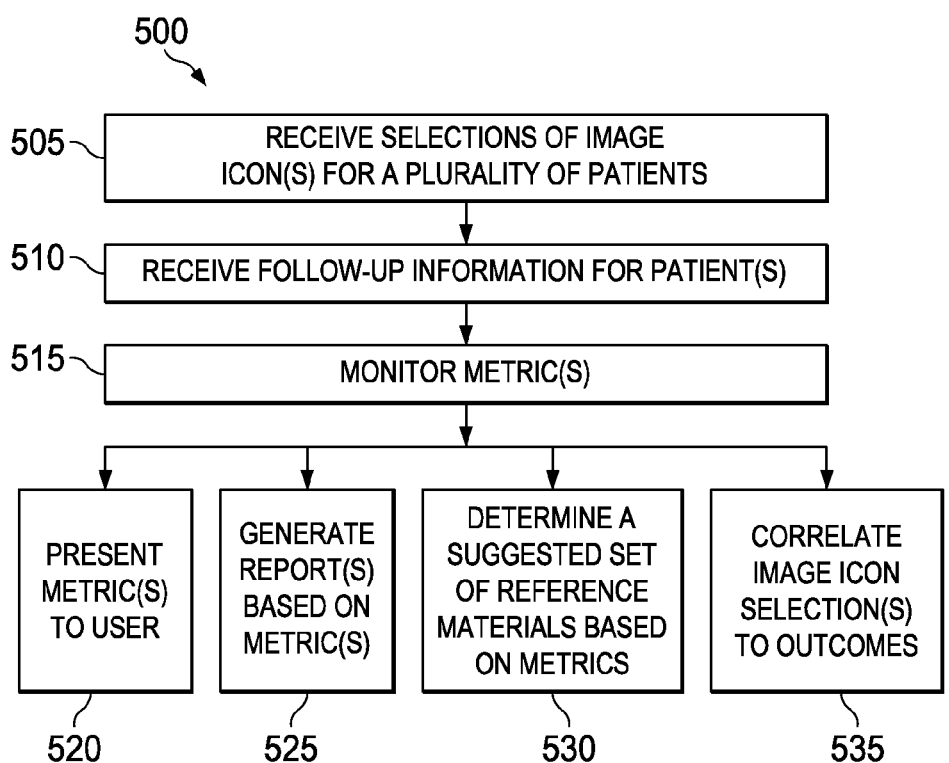
FIG. 15 illustrates an implementation of an example process for monitoring metric(s).

FIG. 15 illustrates an example process 500 for monitoring metric(s). A selection of image icon(s) may be received for a plurality of patients (operation 505). For example, the IMD system may store information provided to the IMD system, such as image icons selected, text icons selected, and/or diagnosis generated, in a memory coupled to the IMD system.

Follow-up information may be received for one or more of the patients (operation 510). Follow-up information may include test results, such as biopsy results, blood tests, etc., related to one or more of the patients. The follow-up information may be transmitted to the IMD system (e.g., automatically and/or by a user) and associated with one or more of the patient records previously stored in a memory coupled to the IMD system.

Metrics may be monitored (operation 515). The data from the stored information, such as selected icon(s) and the follow-up information may be aggregated and/or analyzed to produce one or more metrics (e.g., based on statistical methods and/or commercially available statistical software). Metrics may include: error rates, outcomes associated with diagnoses and/or selected image icons, time spent analyzing images (e.g., per image, per patient, and/or per predetermined category of diagnoses), patient test results analyzed per time period, number of patient records analyzed during a predetermined time period (e.g., per user and/or per groups of users), etc. Metric(s) may be determined based on information provided to the IMD system such as selected icons, follow-up information, time(s), etc. The metrics may be stored in a memory coupled to the system (e.g., user system and/or IMD system) and monitored. One or more statistical analyses may be performed to the stored metrics to determine one or more trends and/or for tracking purposes. For example, an upward or downward trend in number of patient records analyzed may be determined and/or tracked.

Metric(s) may be presented to a user (operation 520). For example, a metric GUI may be determined by the IMD system. A notification may be transmitted based on and/or including the metric. In some implementations, the metric(s) may be presented to the user, a designated user (e.g., Clinic head) and/or groups of users (e.g., via a transmitted notification and/or GUI(s) generated by the IMD system).

Report(s) may be generated based on the metrics (operation 525). For example, compliance with one or more industry and/or government standards may include transmission of reports of various metrics, such as number of patients test results analyzed. The IMD system may automatically determine metric(s) and/or automatically generated reports for compliance with industry and/or government standards (e.g., based at least partially on the determined metric(s) and/or criteria of the industry and/or government standards). The IMD system may automatically transmit the report(s) to the appropriate entity. In some implementations, the IMD system may automatically generate a compliance report, present the compliance report to a user (e.g., user associated with the compliance report and/or a department head), and/or automatically transmit the report(s) to the appropriate entity after receiving approval (e.g., via the GUI) from the user to which the report is presented.

A suggested set of reference materials may be determined based on the metrics (operation 530). In some implementations, the IMD system may generate a listing of references for presentation to the user based on determined metric(s). For example, the IMD system may determine metrics, such as accuracy and/or error rates, based on follow-up test and determine whether the metric is correlated to a specific area (e.g., associated with the selection or lack of selection of particular image icon(s)). The IMD system may then retrieve a suggested set of references related to the specific area (e.g., a set of references primarily and/or secondarily associated with image icon(s)). In some implementations, the IMD system may track metrics such that new areas of diagnoses for a user may be identified. The IMD system may generate a suggested set of reference materials based on the new areas of diagnoses. The IMD system may determine that a user is diagnosing using a statistically significant greater number of a particular image icon than other users, and may correlate the user error rate to suggest a set of references related to the image icon.

Image icon(s) selections may be correlated to outcome(s) (operation 525). For example, selections of image icon(s) may be aggregated from patient-de-identified data sets and correlated to outcomes (e.g., to comply with industry, government, and/or insurance regulations). For example, the IMD system may correlate follow-up information, such as outcomes (e.g., from biopsies, further testing, operative testing, and/or temporal follow-up), with diagnoses provided (e.g., via image icons selected) and determine probabilities of future outcomes based at least partially on the image icon or icons selected for the patient case in question.

Process 500 may be implemented by various systems, such as system 100. In addition, various operations may be added, deleted, and/or modified. For example, the determination of metrics, monitoring, and/or storage of information may comply with government, industry, and/or facility regulations, such as HIPAA (Health Insurance Portability and Accountability Act) and/or ACA (Affordable Care Act). In some implementations, the determined outcomes may be presented to user(s). In some implementations, the described process and/or operations thereof may be performed by the IMD system and/or an IMA system in other environments (e.g., forensic analysis, body imaging, and/or security screening).

Figure 16:
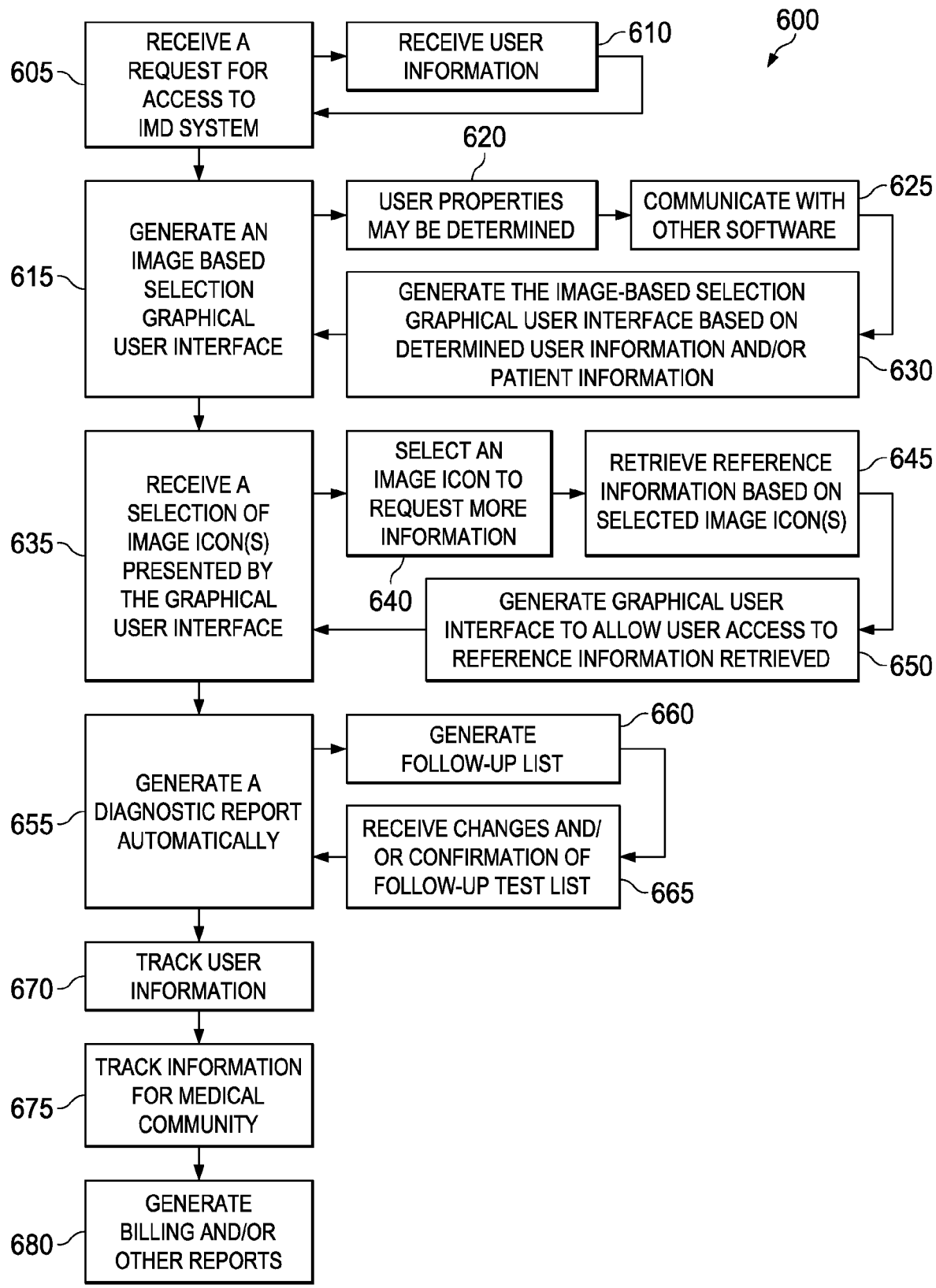
FIG. 16 illustrates an implementation of an example process for operating an image based medical diagnostic (IMD) system.

FIG. 16 illustrates an implementation of an example process 600 for operating an image-based medical diagnostic (IMD) system. A request may be received for access to an IMD system (operation 605). For example, a user may access a website that is a GUI generated by the IMD system. In some implementations, a portion of the presentation interface of the IMD system may be stored on a user device and/or access to the IMD system may be provided through the GUI generated by the portion of the presentation interface stored on the IMD system. The GUI may be a website accessed by the user.

User information may be received (operation 610). For example, a user may log into the IMD system by providing a user name and/or password. As another example, user information may be stored on a memory of the user device and the user information may be transmitted by the user device to the IMD system. The IMD system may compare the user information to user information in a memory of the IMD system to retrieve appropriate information (e.g., task lists, unconfirmed generated reports, statistics based on tracking, and/or notifications such as notification that user has satisfied regulatory requirements).

An image-based selection GUI may be generated (operation 615). For example, the diagnostic interface, reference interface, presentation interface and/or portions thereof may generate the image-based selection GUI.

User properties may be determined (operation 620). For example, specialty, assigned cases, and/or name and/or type of hospital that is serviced may be determined (e.g., from user records and/or user input). The user properties may indicate preferences for report generation, reporting requirements (e.g., government, industry, licensing, and/or research), and/or billing practices that may be utilized at least in part by the IMD system. In some implementations, the user properties may be retrieved based on the user information received to login to the IMD system.

The IMD system may communicate with other software, such as a third party interface for viewing patient test results (operation 625). For example, the IMD system may retrieve patient medical history. As another example, the IMD system may compare the patient identification information associated with the generated GUI for a patient with the patient information related to medical images generated by commercially available software, such as PACS/RIS/BRIS modules available from GE, Phillips, Siemens, McKesson (e.g., Magview module); Hologic (e.g., MRS module), and/or PenRad. In some implementations, the GUI may not retrieve and/or restrict presentation of medical images of a patient within the GUI.

The image-based selection GUI may generate the image-based selection GUI based on determined user properties and/or patient information (operation 630). For example, the image-based selection GUI may include image icons based on the medical cases to be analyzed and/or the types of tests that produced the medical images. The image-based selection GUI may include image icons based on the specialty of the physician. The image-based selection GUI may generate the GUI based on patent information such as reason for imaging. Other icons and/or tabs within the GUI may be presented on the image-based selection GUI based on the user properties and/or patient information.

A selection of one or more image icons presented by the image-based selection GUI may be received (operation 635). For example, a user may click, touch, and/or otherwise select an image icon on a user device, such as a tablet computer, and the information may be transmitted to the IMD system. The user may select one or more image icons to enter a diagnosis for a patient. Allowing the user to select an image to enter diagnosis, rather than dictating a diagnosis, may facilitate tracking since common diagnosis terms may be associated with the image icons for use in reports; can be assigned specific codes in the database; may be more cost efficient since users may be able to quickly enter diagnosis information; may reduce errors due to transcription of dictation; may reduce errors by providing reports approximately concurrently with diagnosing patients; and/or may be generally quicker for a user because as a user gains familiarity with the GUI and image icons, diagnoses may be quickly selected (e.g., when compared with the amount of time associated with having to repeat common diagnosis terms for each patient file when dictating).

A user may utilize the image-based selection GUI to request more information by selecting an image icon (operation 640). For example, if a user selects an image icon to request more information, the IMD system may retrieve reference information (e.g., via the reference interface and/or by retrieving information by accessing repositories) (operation 645). The reference information may be indexed based on images (e.g., image icons) and/or other icons and thus by selecting an icon, information that may be relevant to diagnosing and the image in the icon may be viewed. In some implementations, users may flip through a plurality of images in the reference information to facilitate a formulation of a diagnosis.

The image-based selection GUI may be generated so that the user may access reference information retrieved (operation 650) and/or view reference information correlated (e.g., through the index) to the selected image. For example, if a user is unsure that a possible diagnostic term (e.g., image icon and/or other icon) accurately reflects at least a portion of a patient medical image, a user may select the possible diagnostic term image icon and access reference information related to the icon. Thus, a user may access reference information that may be relevant to diagnosing based on a possibly similar image rather than search terms and as such may be able to retrieve reference information without knowledge of appropriate search terms, in some implementations.

A diagnostic report may be automatically generated (operation 655). For example, the IMD system may utilize the selected image icons to formulate the diagnosis in words for transmission to a patient and/or referring physician. The diagnostic report may be generated based at least partially on common terms in the field and/or uniform diagnostic terms. For example, governments, medical boards, hospitals, and/or insurers may require diagnostic reports to utilized specified uniform diagnostic terms. The IMD may retrieve the specified uniform diagnostic terms and generate the patient report at least partially based on the retrieved terms. The report may also be generated at least partially based on retrieved patient information (e.g., from interfacing with other commercially available software). The report may be text and/or image searchable.

Generating text and/or image searchable reports may facilitate compliance with government regulations, industry recommendations, and/or research endeavors.

Other reports may be automatically generated. For example, a follow up test list may be generated (operation 660). A potential follow up test list may be generated by the system at least partially based on icons selected in the GUI and/or other information (e.g., based on common practices in industry, based on hospital preferences, insurance preferences, and/or based on user preferences). Changes and/or confirmation by a user of a generated list of follow up tests may be received (e.g., from a user device) (operation 665). The follow up test list and/or other reports may be automatically transmitted to as appropriate (e.g., to electronic medical record, to physicians, to patients, to medical testing laboratories, etc.).

Information about the user may be tracked (operation 670). For example, regulations may require specific information to be tracked (e.g., to comply with confidentiality requirements, to maintain licensing, to manage business goals, to track efficiency). For example, a radiologist reading mammography may need to track, report, and/or confirm that a predetermined number of mammography records have been read by a user in a specified time. For example, the IMD system may retrieve a predetermined compliance value and compare the value to the number of cases read by the user and determine if a compliance value has been satisfied.

The information may be tracked for the medical community (operation 675) and a report may be generated. Reports based on the tracked information may be generated and/or transmitted (e.g., via email and/or printed) to appropriate other parties (e.g., regulatory boards, hospitals, etc.). For example, a compliance form may be retrieved form a repository and tracked information may be added to the retrieved form. As another example, a nuclear medicine radiologist may be required to comply with various regulations (e.g., government regulations regarding nuclear material, etc.) that would be automatically tracked by the IMD system. In some implementations, user efficiency and/or the efficiency of a group of users (e.g., number read, time required to read, and/or mistakes made) may be tracked and/or reports may be generated for business goals.

Other information related to diagnoses generated (e.g., through the selection of image icons) may be tracked. For example, the CDC or FDA may require reporting of specified diagnosis and/or prevalence of specified diagnosis. The IMD may automatically track and/or report the information to automatically comply with the requirement.

One or more other reports and/or billing reports may be generated (operation 680). For example, reports, such as compliance reports, metric reports, etc. may be generated. A billing report may be generated based at least in part on the image icon(s) selected. For example, CPT and/or ICD-9 codes may be correlated to image icons and billing reports may be automatically generated based at least partially on the selection of image icons.

Process 600 may be implemented by various systems, such as system 100. In addition, various operations may be added, deleted, and/or modified. For example, tracking of patient information and/or portions of patient information (e.g., to comply with regulations such as HIPPA) may be inhibited. As another example, the GUI may have default settings. The default settings may be based on user preferences and/or industry preferences. In some implementations, the described process and/or operations thereof may be performed by the IMD system and/or an IMA system in other environments (e.g., forensic analysis, body imaging, and/or security screening). Although FIGS. 12A-16 illustrate implementations of processes performed by the IMD system, similar processes and/or portions thereof may be performed by the IMA system, independently and/or in combination with one or more other processes and/or portions thereof, as appropriate.

In some implementations, the IMD system may receive and/or retrieve other information. Other information may include pathology from biopsies, results at follow-up, information from electronic medical records, location information and/or measurements related to images and/or occurrences, and/or other appropriate information from image presentation systems such as PACS, other computer aided diagnostic systems, and/or other appropriate systems. The other information may be retrieved automatically from other commercially available software systems by the IMD system and/or input by a user and transmitted to the IMD system.

The system may utilize the other information for compliance with various governmental agency requirements (e.g., Mammography Quality Standards Act [MQSA]) and/or business practice requirements (e.g., billing and/or uniform reporting). For example, a governmental agency may require tracking and/or correlating of various data (e.g., analysis, follow-up recommendations, and/or test results). The IMD system may track and/or generate report(s) based on the tracking and/or correlating. The tracked information may be utilized to create probability of diagnoses and/or malignancies based on diagnoses received through the system (e.g., the system may aggregate diagnoses and/or test results to determine probabilities of malignancy based at least in part on the aggregated information).

In some implementations, the system may present (e.g., through a GUI) a probability of an outcome for a selected image icon(s), other icon(s), and/or selected diagnoses. For example, the system may generate a probability of a diagnosis using the other information received by the system. The system may track and/or correlate selection(s) of image icon(s), other icon(s), and/or test results (e.g., pathology results such as biopsy results). The system may then be able to determine a probability of an outcome (e.g., malignancy) based at least in part selected icons. The system may utilize other information (e.g., from other commercially available software, such as electronic medical record information) when determining correlations and appropriate probabilities between selected icon(s) (e.g., image icons and/or other icons) and outcomes.

The results information (e.g., at follow-up and/or biopsy results) may be aggregated and/or correlated to diagnoses selected and various statistical models may be utilized to generate probabilities (e.g., of outcomes). In some implementations, the probability information may be determined from expert opinions (e.g., input into the system) and/or from other reference materials. The probability information may be stored in a memory of the system and/or in remote repositories. The system may receive a selection of image icon(s) and/or other icon(s) and retrieve a correlated probability based at least in part on the received selections. The probability information may be presented to a user and/or included in reports generated by the system (e.g., probability of malignancy may be included in diagnoses reports and/or the billing code selected may be at least partially based on the probability information).

For example, when a user analyzes a breast image and the user selects an image icon correlated to BI-RADS 4a, a probability of malignancy of 2-10% may be indicated by the system. As another example, a user may analyze an image and the user may select a diagnosis by selecting image icon(s) and/or other icon(s) through the GUI. The system may retrieve probability information (e.g., related to the selected image icon(s) and/or other icon(s)) and present the probability information to the user. The probability information may be at least partially based on the other information retrieved by the system. The system may generate a GUI, such as a pop-up window, that presents at least a portion of the probability information to the user. The GUI may, for example, indicate various things to the user, such as the rarity of the diagnosis selected by the user, the malignancy rate of the occurrence, and/or other probability related information. The user may alter the selection of image icon(s) and/or other icon(s) based at least in part on the probability information, in some implementations. For example, the user may select various follow-up tests based on the probability information and/or the user may re-examine the images and alter a diagnosis based on the probability information. Report(s) generated by the system may include information at least partially based on the probability information (e.g., probability information may be included for compliance with government reporting requirements).

In some implementations, the probability information may be utilized to determine if one or more users is selecting the appropriate icon related to a category (e.g., BI-RAD® or other level of suspicion). For example, if a level of suspicion is related to a 5% or less malignancy outcome and a user's selection of the category is correlated to an approximately 20% malignancy outcome, then the user may be notified of the discrepancy. In some implementations, a reporting agency may be notified when a plurality of user designate a category with an outcome (e.g., percentage of malignancy found) that is different from the outcome the reporting agency and/or other in the industry associate with the category.

In some implementations, other information received and/or retrieved by the IMD system may include location information (e.g., location within the anatomical region, size, signal characteristics such as T1, T2, STIR (Short Tau Inversion Recovery), contrast enhancement (CE), dynamic contrast enhancement (DCE), DWI (diffusion weighted imaging), and/or DTI (diffusion tensor imaging) for MRIs). The location information may be input by a user while obtaining the image (e.g., an ultrasound technician may enter location information). In some implementations, commercial image analysis systems may allow location information such as measurements and position to be obtained through the commercial image analysis system. For example, the user may be able to measure a location of an occurrence (e.g., lesions) through the system through which the user views the x-ray.

The IMD system may generate one or more GUIs to facilitate interaction, receipt of information, and/or presentation of information to user(s), FIGS. 17-25 illustrate implementations of example GUI(s) generated by the IMD system. The GUI(s) may be presented on a user device, for example, through a website and or via a local site. Access to the GUI(s) and/or information therein may be secured (e.g., to ensure compliance with one or more government and/or industry standards). The GUI(s) may include a home-screen (e.g., preset home-screen and/or based on user preferences) and tabs corresponding to one or more other GUIs, such as diagnostic GUI(s) including abbreviated diagnoses GUI(s) and other diagnoses GUI(s), report GUI(s), work-list GUI(s), etc.

During use, a user such as a radiologist, may access the IMD server through a GUI (e.g., logon GUI) generated by the IMD server. The radiologist may view the GUI(s) generated by the IMD server on a first user device, such as a tablet computer, and view medical images of a patient (e.g., patient test results) on additional user device(s). In some implementations, the user may view medical images, such as ultrasounds and CT scans, on one more monitors coupled to the additional user device(s) and view the GUI generated by the IMD system on another monitor coupled to the user device and/or screen of a tablet computer, as illustrated in FIG. 10. The medical images of the patient may be retrieved using commercially available medical image software (e.g., third party systems, as illustrated in FIG. 10). The IMD system may interface with the medical image software to ensure diagnostic information entered through the GUI is correlated to the medical images presented by the medical image software. For example, the IMD system may request patient information from the medical image software and generate GUIs based on the patient information. The IMD system may allow a user to input patient identification information (e.g., scan a barcode, type a number) into the generated GUI and retrieve information about the associated patient based on the input patient identification information and/or transmit a request to the medical image software for confirmation of the patient identification information.

Figure 17A:
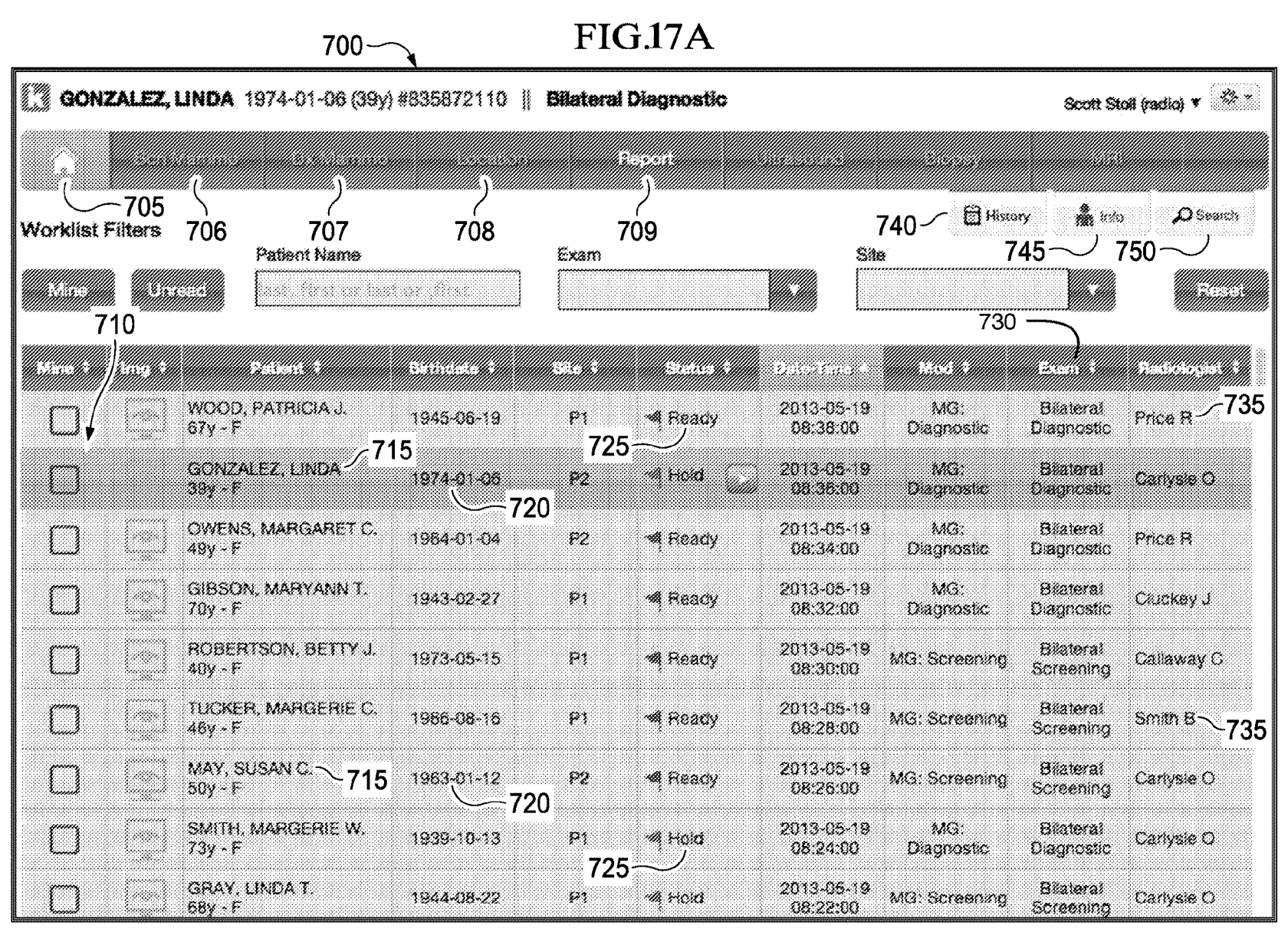

In various implementations, the IMD system may generate a work-list GUI. FIG. 17A illustrates an implementation of an example work-list GUI 700. A user may access the IMD system (e.g., via the Internet) and provide one or more credentials, such as user names and/or passwords. The IMD system may generated a work-list GUI as illustrated in FIG. 17A, based at least partially on the provided credentials. As illustrated, the work-list GUI 700 may be accessible to a user by selecting a tab on the interface, such as a home-screen tab 705. A listing 710 of one or more patients, with whom test results are associated, may be included in the work-list GUI 700. The listing 710 may include patient record information such as patient name 715; identifying information, such as birth date 720; status and/or status indicia 725, type of examination 730, and/or username 735 or other user information related to a user assigned to evaluate test results associated with the patient record. Additional information about a selected user may be presented to a user via one or more tabs, such as exam history tab 740 and/or patient information tab 745. FIG. 17B illustrates an example of a work-list GUI 760 in which the exam history tab 740 has been selected for presentation.

Figure 17C:
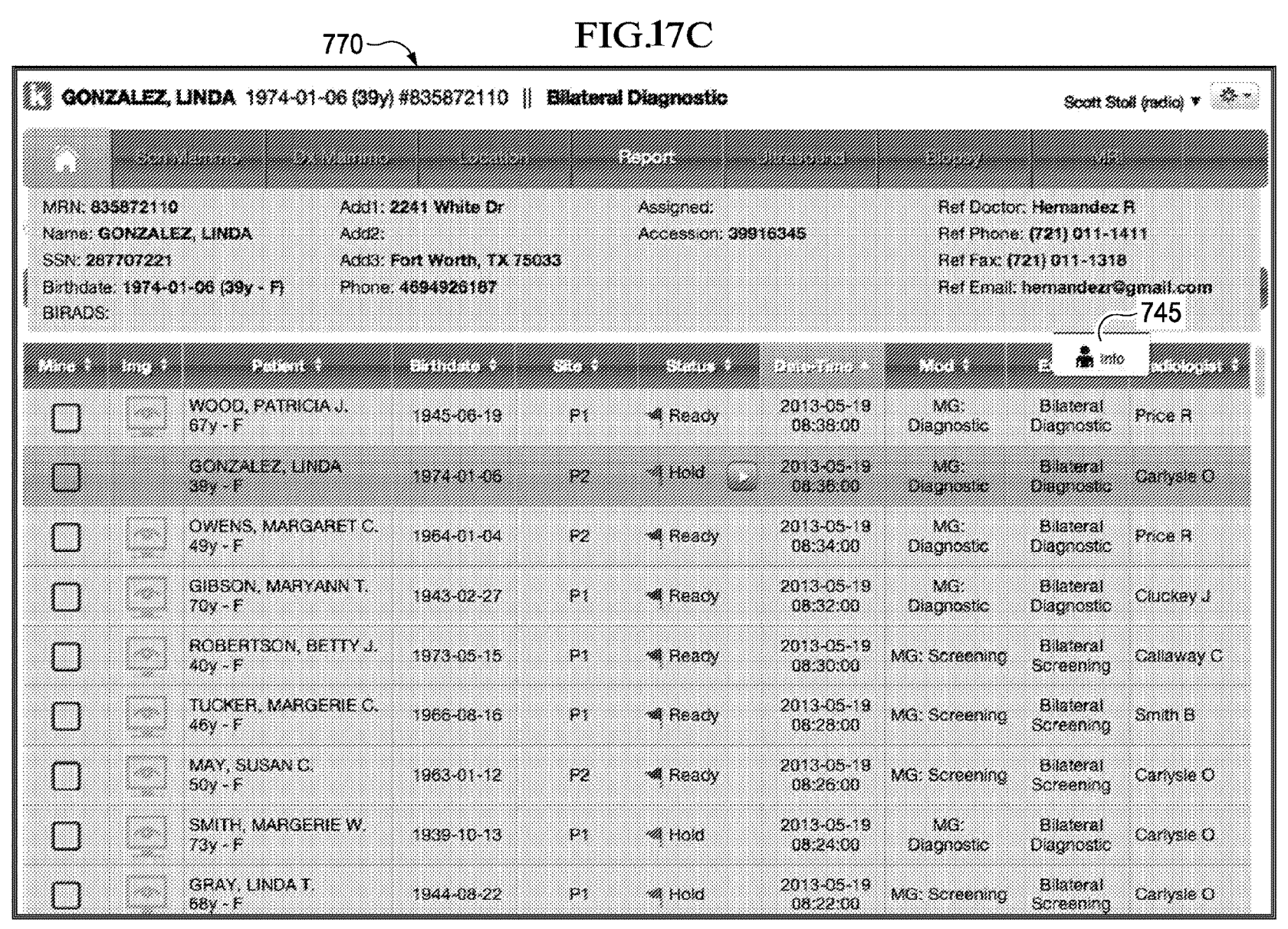
Figure 17D:
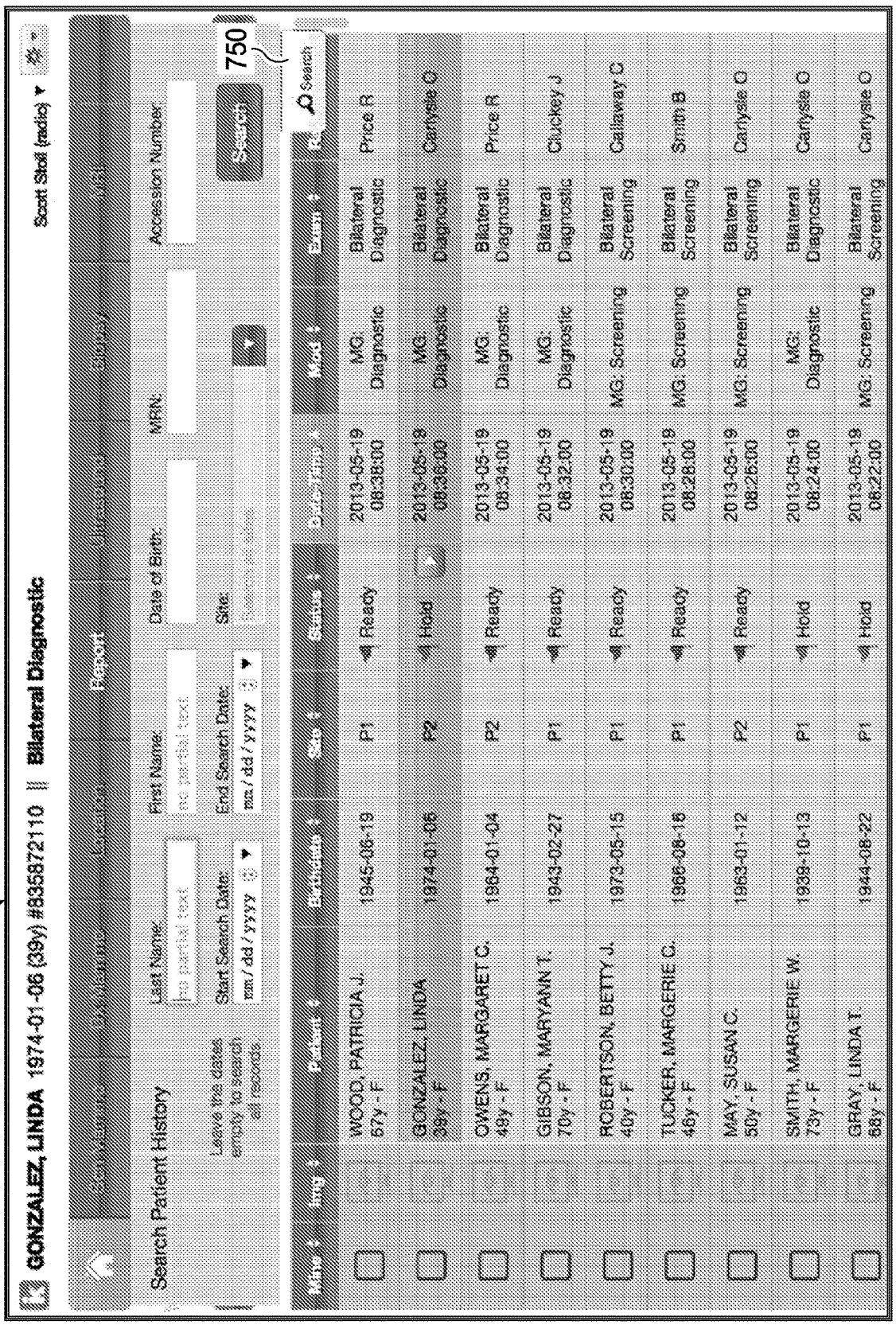

In some implementations, the IMD system may communicate with one or more third party systems to determine the additional information, such as exam history, patient history, medical record information, etc. For example, the IMD system may pull examination history from an electronic medical record stored in a memory (e.g., database) coupled to the IMD system. FIG. 17C illustrates an example of a work-list GUI 770 in which the patient information tab 745 has been selected for presentation. A user may search for information such as a patient record via a search tab 750. FIG. 17D illustrates an example of a work-list GUI 780 in which the search tab 750 has been selected for presentation.

As illustrated in FIG. 17A, the GUI(s) generated by the IMD system may include tabs that allow the user to request presentation of various GUIs. For example, the GUI(s) may include a home-screen tab 705; one or more diagnoses GUIs presented through one or more diagnoses tabs, such as an abbreviated diagnosis tab 706 and/or a diagnosis tab 707; a location tab(s) 708; and/or report tab(s) 709.

In some implementations, tabs may allow presentation of GUIs that include information such as task lists that include assigned cases, generated reports, and/or custom screens. The user may customize a custom screen by inputting user preferences (e.g., user tracking data including number of cases read, efficiency, and/or billing reports). The tabs may also include various tabs that relate to different types of medical images that may be viewed and/or analyzed by the user. For example, a <Dx Mammo> tab may generate an interface that allows entry of a diagnosis (e.g., by selection of image icons and/or other icons) related to a mammography case. An <Ultrasound> tab may generate an interface that allows entry of a diagnosis (e.g., by selection of image icon(s) and/or other icons) related to the analysis of an ultrasound. A <Screen Mammo> tab may generate a home page or initial starting point page for selection of image icons and/or other icons related to a diagnosis.

In some implementations, a user may select a patient from the work-list GUI 700 and then select a diagnoses GUI through a diagnosis tab. The diagnostic GUI may include image icon(s). The image icon(s) may include at least a portion of a photographic image, such as a medical image (e.g., CT scan and/or ultrasound). The photographic image selected for inclusion in the image icon may be a typical, exemplary, and/or common occurrence of a diagnosis or portion thereof. For example, a cyst may typically present in a CT scan in a similar manner as a first photographic image. The first photographic image or portions thereof may be included in a characteristic image icon for a cyst.

In some implementations, the IMD system may include more than one diagnostic GUI, in some implementations. For example, diagnosis GUIs may include abbreviated diagnostic GUI(s); one or more specialized diagnosis GUI(s), such as MRI diagnostic GUI(s), ultrasound diagnostic GUI(s), and/or body imaging GUI(s); and/or other diagnostic GUI(s). In some implementations, an abbreviated diagnostic GUI may be available with fewer image icons than a non-abbreviated diagnostic GUI. The abbreviated diagnostic GUI may allow a user to quickly provide a selected set of diagnoses. For example, the abbreviated diagnostic GUI may allow a user to quickly select a benign diagnosis or BI-RADS® 0 Category of assessment.

Figure 18A:
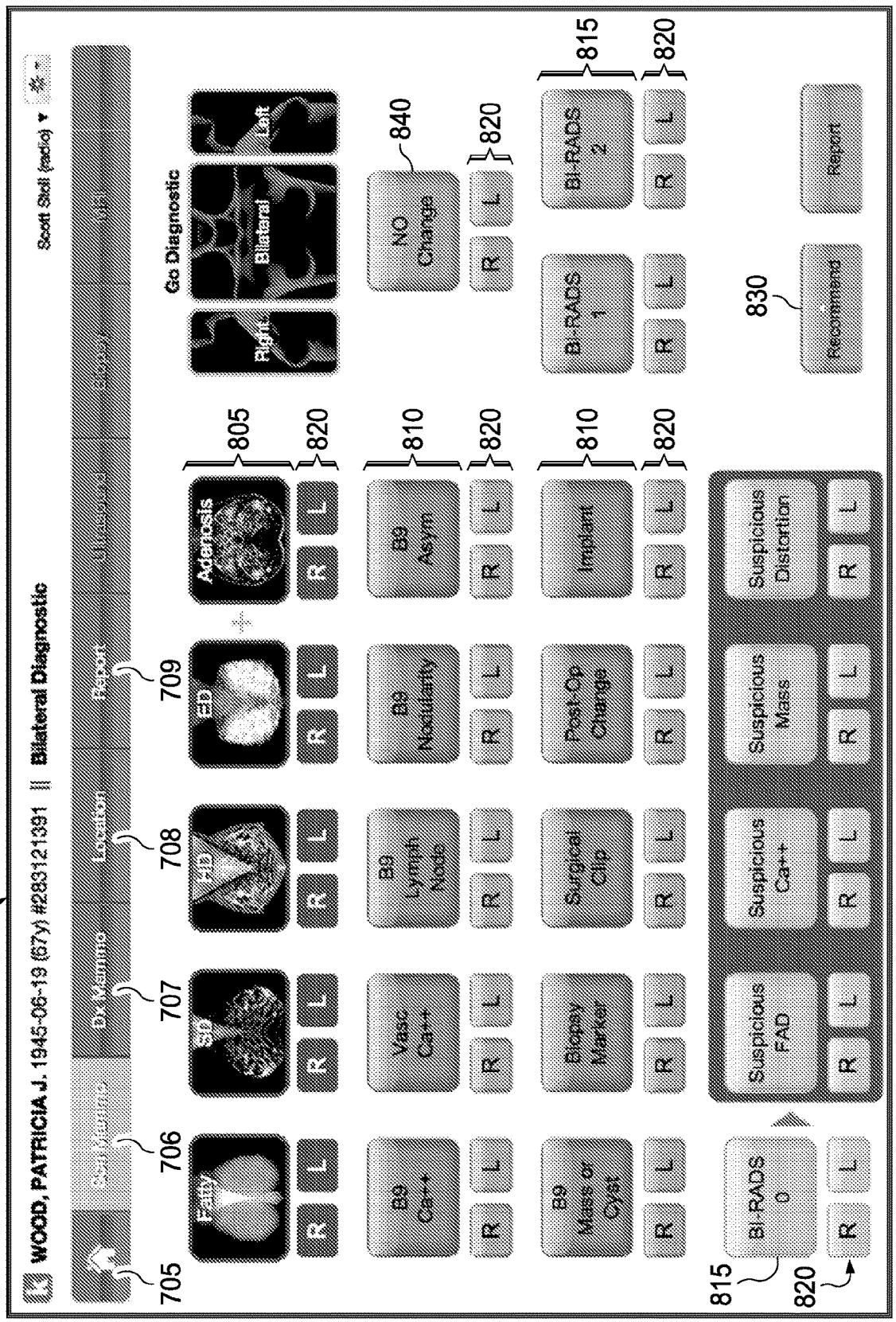
FIG. 18A illustrates an implementation of an example abbreviated diagnosis graphical user interface.

FIG. 18A illustrates an implementation of an example of an abbreviated diagnostic GUI 800 generated by the IMD system. In some implementations, after a user selects a patient form a work-list, a user may select the abbreviated diagnostic GUI though which diagnosis information related to the selected patient and/or test results of the patient may be provided. In some implementations, a user may select the abbreviated diagnosis tab 706 to request presentation of the abbreviated diagnostic GUI 800. The abbreviated diagnostic GUI 800 may include one or more image icons. As illustrated, the diagnostic GUI 800 includes characteristic image icons, such as breast density image icons 805. In some implementations, each breast density image icon 805 may correspond to a different level of breast density. As illustrated, the breast density image icon(s) 805 may include text (e.g., abbreviations of diagnoses) that is related to the photographic image in the breast density icon. The user may request variations of an image icon (e.g., by double-click the image icon, by selecting the image icon and one other text icon, and/or by selecting image icon(s) and requesting variation information). The IMD system may retrieve one or more images and/or image icons depicting variations of the characteristic in the image icon selected. For example, if variations of a fatty breast density image icon is requested by a user, then the IMD system may retrieve variations of fatty breast density (e.g., examples of different presentations of fatty breast density). Selection among two or more image icons may be facilitated by presenting variations to the user. For example, if the patient test results include breast imaging and the user is unsure which categorization of breast density the patient test results fall within, then presentation of variations facilitate selection of the categorization. In some implementations, a third party system may pre-screen patient test results to determine breast density and indicia may be presented on the diagnostic GUI breast density image icon proximate the breast density category determined by the pre-screening. The user may then confirm the breast density category and/or alter the category (e.g., by selecting a different image icon).

The abbreviated diagnostic GUI 800 may include one or more text icons, such as text diagnosis icons including characteristic text icons 810 and/or BI-RAD text icons 815. The text diagnosis icons 810 included in the abbreviated diagnostic GUI 800 may be a preselected set of the text diagnosis icons included in a non-abbreviated diagnostic GUI 800.

In some implementations, an anatomical location corresponding to a selected image and/or text icon may be selected. The abbreviated diagnostic GUI 800 may include text icons, such as anatomical location text icons 820, selection of which may indicate a location of a patient corresponding to a selected image icon(s) and/or diagnosis text icon(s). In some implementations, the abbreviated diagnostic GUI 800 may include an anatomical location graphic 810 through which an anatomical location may be provided.

Figure 18B:
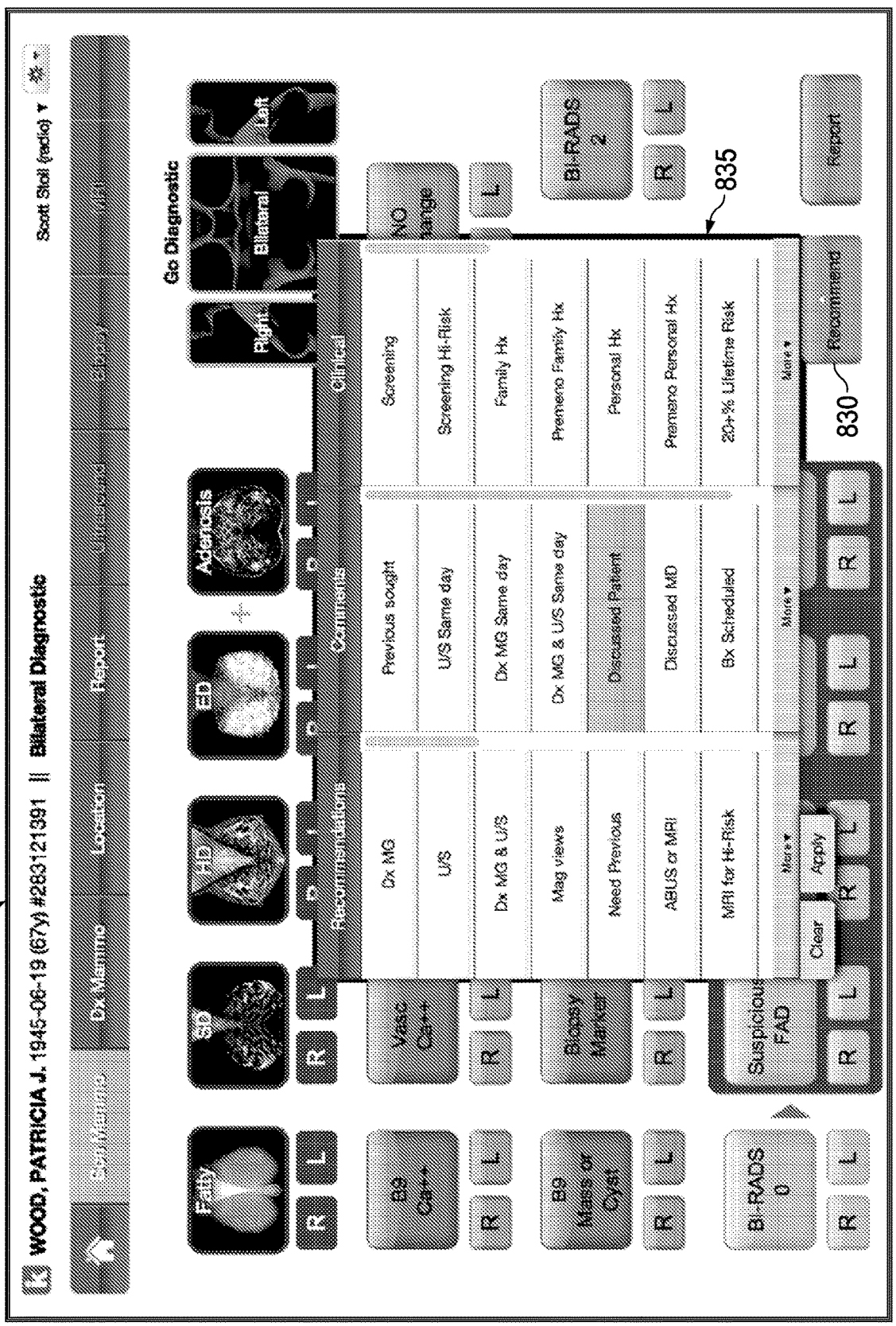
FIG. 18B illustrates an implementation of an example abbreviated diagnosis graphical user interface.

The abbreviated diagnostic GUI 800 may include icons 830 that when selected allow a user to provide additional information for inclusion in the diagnostic report and/or the patient record. As illustrated in FIG. 18B, when an icon 830 is selected, recommendations may be provided through an additional information interface 835 generated by the IMD system. The additional information interface 835 may allow recommendations, comments, follow-up tests and/or other additional information to be provided by a user (e.g., through selection of fields). In some implementations, the abbreviated diagnostic GUI 800 may include a text icon to indicate whether a change has occurred since a previous test result 840.

Figure 19A:
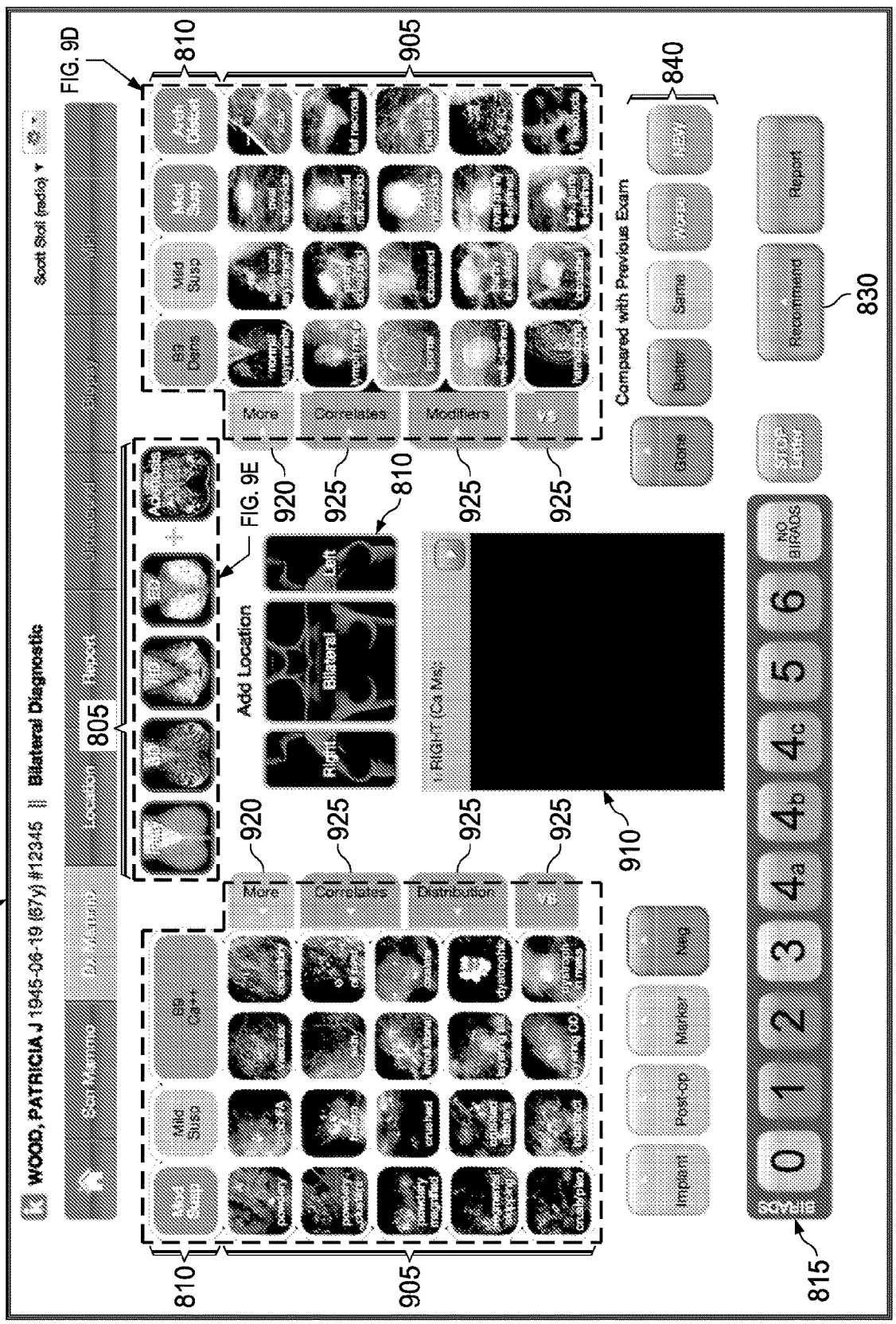
FIG. 19A illustrates an implementation of an example diagnosis graphical user interface.
Figure 19B:
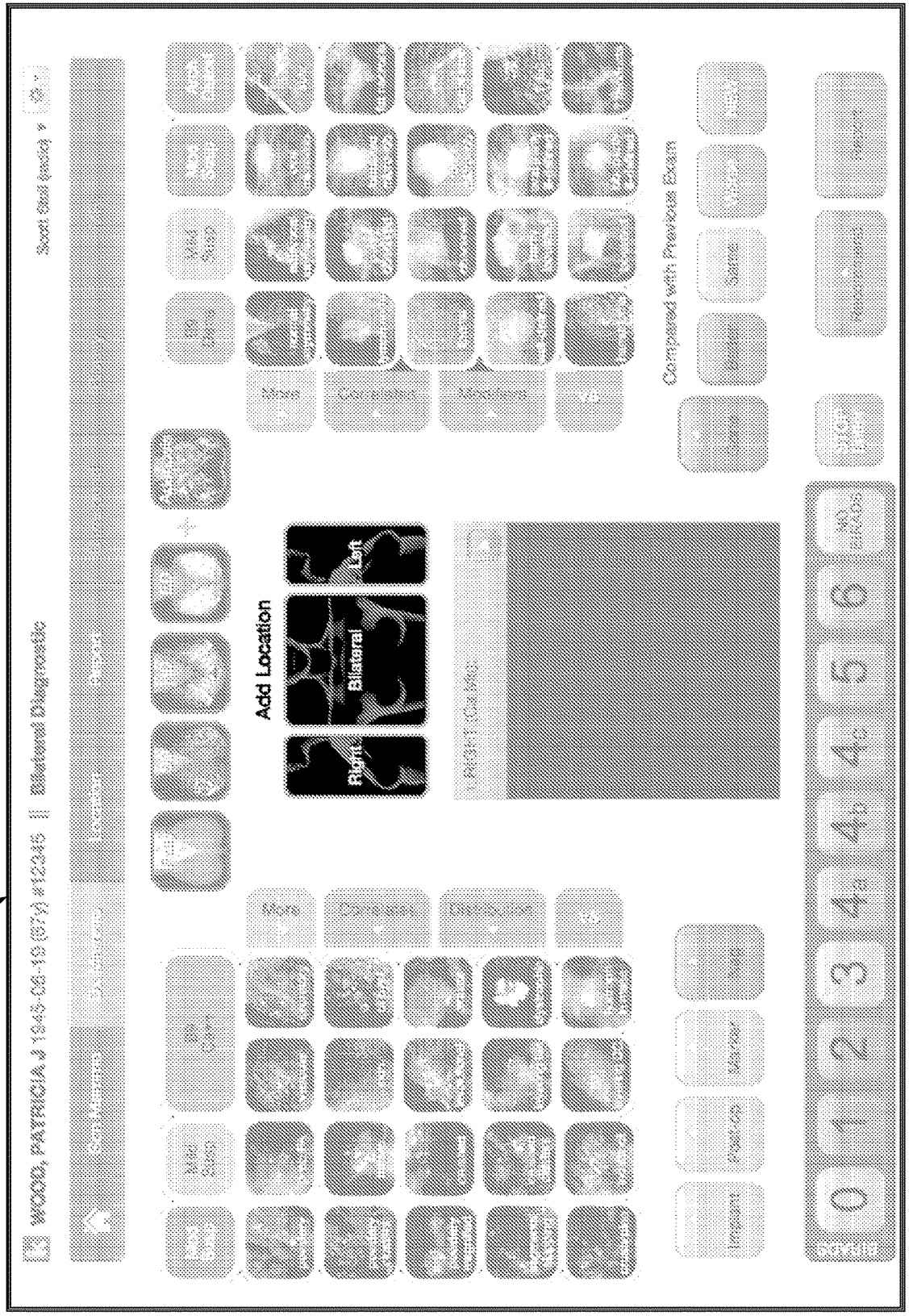
FIG. 19B illustrates an implementation of an example diagnosis graphical user interface in which selection of one or more icons is restricted.
Figure 19:
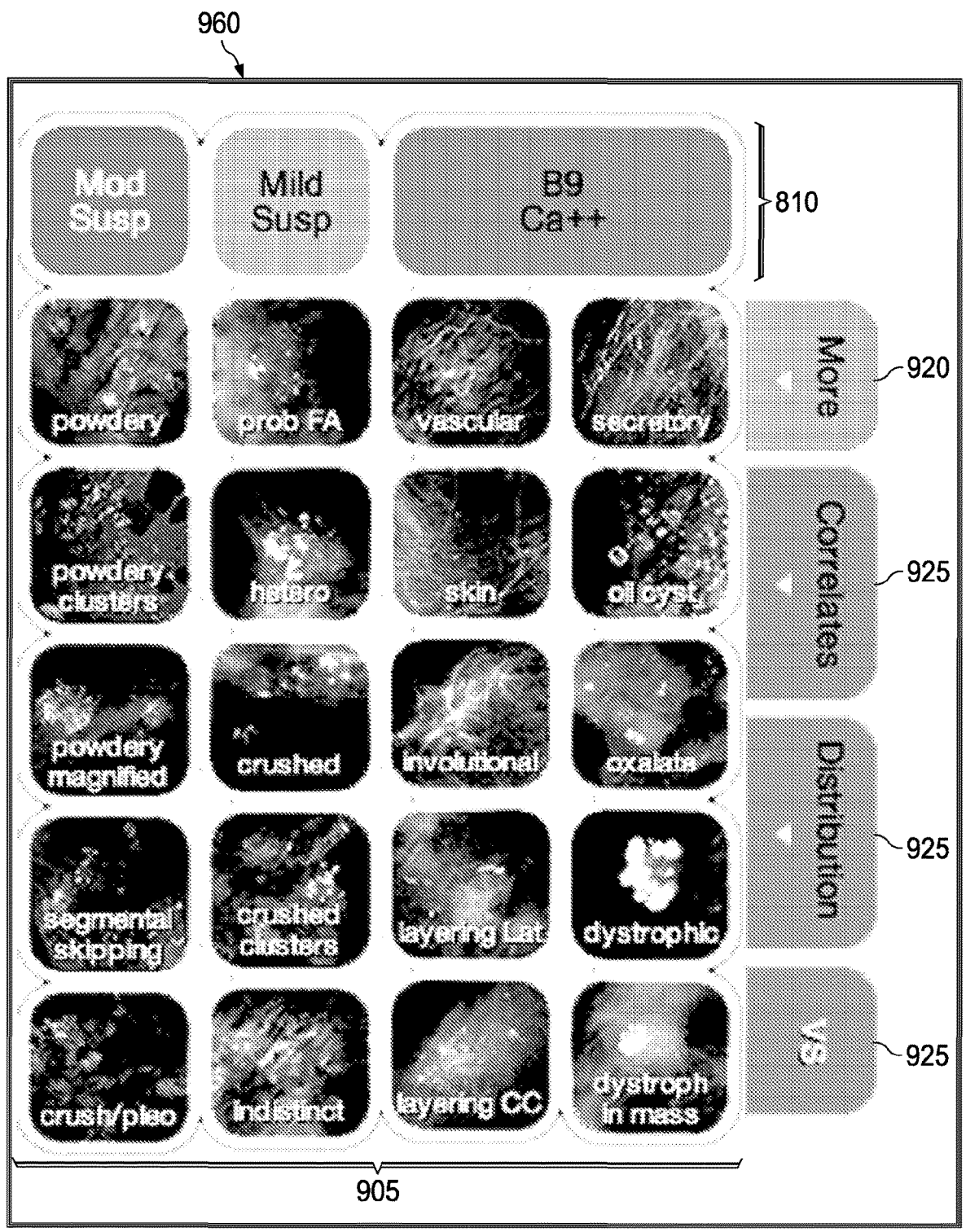
FIG. 19C illustrates an implementation of a portion of the example diagnosis graphical user interface illustrated in FIG. 9A.
FIG. 19D illustrates an implementation of a portion of the example diagnosis graphical user interface illustrated in FIG. 9A.
FIG. 19E illustrates an implementation of a portion of the example diagnosis graphical user interface illustrated in FIG. 9A.
FIG. 19F illustrates an implementation of an example diagnosis graphical user interface.
Figure 19D:
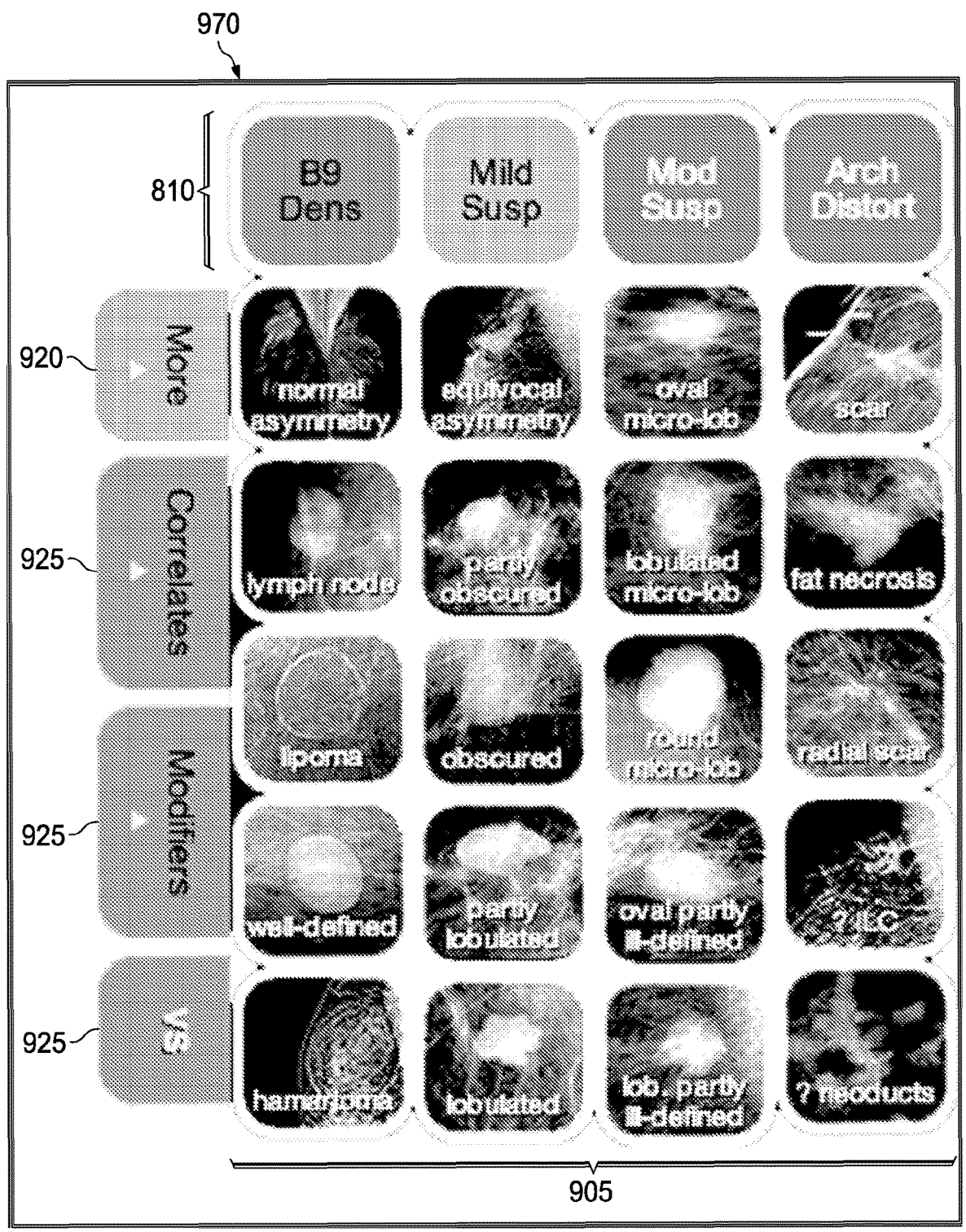
Figure 19E:

In some implementations, a user may select a diagnostic GUI with more image icons than available through the abbreviated diagnostic GUI (e.g., thus, more detail and/or diagnoses may be provided compared to the abbreviated diagnostic GUI). For example, a user may select a diagnosis tab 707 through a GUI of the IMD system. In some implementations, the user may select a patient and the IMD system may communicate with a third party system to ensure that the selected patient corresponds to the patient test results being presented to the user through the third party system. The IMD system may generate a diagnosis GUI based at least partially on a selected patient, the test results presented through the user via a third party system, patient electronic medical records, etc. FIG. 19A illustrates an implementation of an example diagnostic GUI 900 generated by the IMD system. FIGS. 19B, 19C, and 19D illustrate different portions of the example diagnostic GUI illustrated in FIG. 19A. FIG. 19E illustrates a schematic of an implementation of an example diagnostic GUI 900 generated by the IMD system.

As illustrated in FIGS. 19A-E, the diagnostic GUI 900 may generate and/or present image icons including characteristic icons, such as breast density image icons 805 and/or lesion characteristic icons 905, and/or other icons. As illustrated, the image icons may include at least a portion of a medical photographic image of an example of a characteristic. The image icon may include at least a portion of a photographic image of the presentation of a characteristic (e.g., an example of a presentation of a characteristic). The image of the presentation of a characteristic (e.g., as a typical presentation) may be selected by an administrator, such as an expert in the field. For example, the image icon may include a portion of an MRI of an aneurism, a portion of a radiograph of a mass, etc. The image icons may include text that describes the characteristic illustrated in the image icons. For example, an image icon that includes at least a portion of a medical photographic image of powdery calcification may include text such as "powdery" and/or an image icon that includes a medical image of well-defined mass may include text such as "well-defined". For example, rather than including line drawings or other representations of characteristics, the IMD system may utilize image icons that include photographic images. The use of photographic images in image icons may increase the ease of use of the IMD system for users, since the user does not have to translate what the drawing of a characteristic actually looks like in a patient test result. In some implementations, the user of photographic images may allow and or aid a user in the identification of unknown characteristics. For example, if the user identifies a characteristic in a patient test result, but does not know the name of the characteristic, then the user may identify the characteristic based on the photographic image in the image icon on a GUI of the IMD system. In some implementations, a characteristic in a patient test result may not closely resemble image icon(s) in the GUI and the user may utilize the photographic images of variations retrievable by the system to identify the characteristic based on the images.

As illustrated, the diagnostic GUI 900 may include one or more text icons, such as diagnostic text icons 810 and/or BI-RAD or other categorization text icons 815. The diagnostic text icon may be associated with at least a portion of the diagnosis. For example, a diagnostic text icon may indicate a level of suspicion and/or other information related to a diagnosis or portion thereof (e.g., a benign calcification, a surgical clip, a biopsy marker, an implant, mass, cyst, post-operative change). The other categorization text icons may include a size text icon 920. The size text icon 920 may control the number of image icons presented through a diagnostic GUI 900. For example, a size text icon 920 may be to cause a greater number of image icons to be displayed (e.g., by selecting a <more> size text icon) and/or may cause fewer image icons to be displayed (e.g., by selecting a <less> size text icon).

In some implementations, the number of image icons and/or text icons presented on the diagnostic GUI 800, 900 may be based on the user device, type of user device, presentation device size (e.g., screen size), user preferences, etc. For example, the IMD system may automatically determine the number of image icons and/or text icons to include in a generated GUI based on the user device and/or properties thereof (e.g., screen size). A user may request alteration of the number of image icons and/or text icons presented in the generated GUI, for example, by selecting a size text icon, such as the size text icon 920 illustrated in FIG. 19A. The IMD system may receive the request to alter the number of image icons and/or text icons (e.g., by selection of a size text icon) and alter the number of image icons and/or text icons included in the generated GUI.

The diagnostic GUI 900 may include one or more other icons that allow comparisons to previous test results 840 and/or other additional information 830.

The diagnostic GUI 900 may allow a user to provide location information, such as an anatomical location of a patient (e.g., corresponding to an anatomical location in the test results of the patient). As illustrated, the diagnostic GUI 900 may include an anatomical location graphic 810 and/or other portion 910 to allow a user to select and/or provide an anatomical location to be associated with the patient record. The anatomical location graphic 810 may be an image and/or a drawing of at least a portion of a body. A user may be able to select an anatomical location through the anatomical location graphic 810. For example, indicia (e.g., a dot, a circle, a flag) may be placed on a portion of the anatomical location graphic 810 to provide an anatomical location (e.g., to the IMD system to be associated with a patient record).

In some implementations, the IMD system may restrict and/or allow selection of various icons based on predetermined preferences, user preferences, industry preferences, etc. For example, selection of one or more image icons may be restricted until a selection of an anatomical location is received. FIG. 19B illustrates an example diagnostic GUI 950 in which selection of image icons is restricted. As illustrated, the image icons are grayed or hidden to indicate that the icons may not be selected. In some implementations, a user may not be restricted in which icons may be selected.

In some implementations, during use, a user may select a patient from a work-list GUI 800. The IMD system may communicate with a third party system through which patient test results are retrieved for presentation on a user device. The IMD system may communicate with the third party system such that the patient test results being presented to the user via the third party system are associated with the same patient and/or record as the patient record in which a diagnosis will be entered through the IMD system. The user may then select a diagnostic GUI 800, 900 though which a diagnosis may be provided by the user. For example, the user may view the medical images from patient tests, such as mammography, and view the icons in the GUI of the IMD system. The user may select image icon(s), such as lesion characteristic icons 905, that correspond to the analysis of the patient test results presented to the user. The user may select an anatomical location (e.g., via a anatomical location graphic 810) and/or other icons, such as diagnosis text icons 810, BI-RAD text icons 815, icons to provide comparisons to previous test results 840, additional information icons 830, and/or association icons 925.

The association icon(s) 925 may allow a user to indicate a relationship between selected image icons. For example, association icon(s) may be text icons that indicate that image icons are correlated (e.g., "and" and/or "or"), distribution, modifiers, pertinent negative diagnosis (e.g., "not"), and/or to provide differential diagnosis information (e.g., 'vs.' icon). In some implementations, the user may select more than one image icon via the diagnostic GUI 800, 900 and one or more association icons 925 to indicate the relationship between the selected icons. Users may thus select that certain diagnoses or portions of diagnoses correlated to image icons are present and/or not present in the patient medical images and/or specific anatomical locations of such being analyzed by the user. The inclusion of negative diagnosis information may provide additional information to the generated diagnosis based on selected image icons for other physicians, for example, in the generated report.

Figure 20:
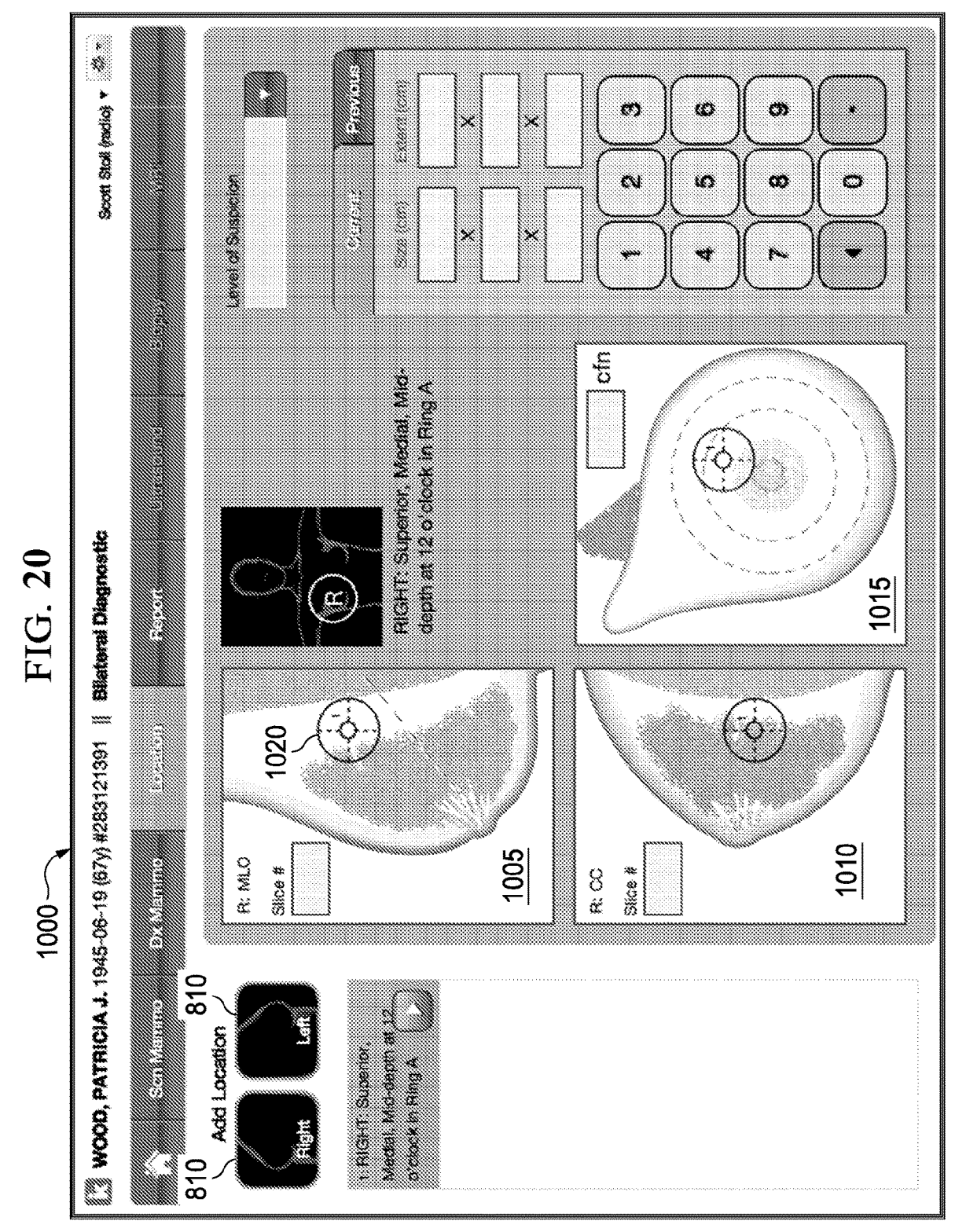

In some implementations, location GUI(s) may be generated by the IMD system through which a user may provide anatomical location(s). FIG. 20 illustrates an implementation of an example location GUI 1000. The location GUI 1000 may include one or more graphical images (e.g., line drawing) that illustrate a representation of a patient or portion thereof. For example, as illustrated, the location GUI 1000 may include graphical images that illustrate different views of a breast 1005, 1010, and 1015. A user may position a location indicator 1020 on one or more of the views 1005, 1010, and 1015 to provide an anatomical location. The location GUI may include an anatomical location graphic 810, to, for example, indicate to which side of a patient's body a positioned location indicator corresponds. A diagnosis corresponding to the anatomical location may be provided through a diagnostic GUI 800, 900. In some implementations, a level of suspicion may be provided.

In some implementations, the location GUI(s) may be automatically generated by the IMD system based on patient test results, user properties (e.g., belongs to mammography group and/or body imaging group), and/or user selections (e.g., user provides anatomical location included in the patient test results). For example, when an MRI of a breast is included in the patient test results, the IMD system may automatically generate a location GUI that includes images of the breast. In some implementations, when a radiograph of an arm is included in the patient test results, the IMD system may automatically generate a location GUI that includes images of an arm. The image illustrated in the GUI may be a representation of an anatomical location rather than the image in the patient test results.

Figure 21:
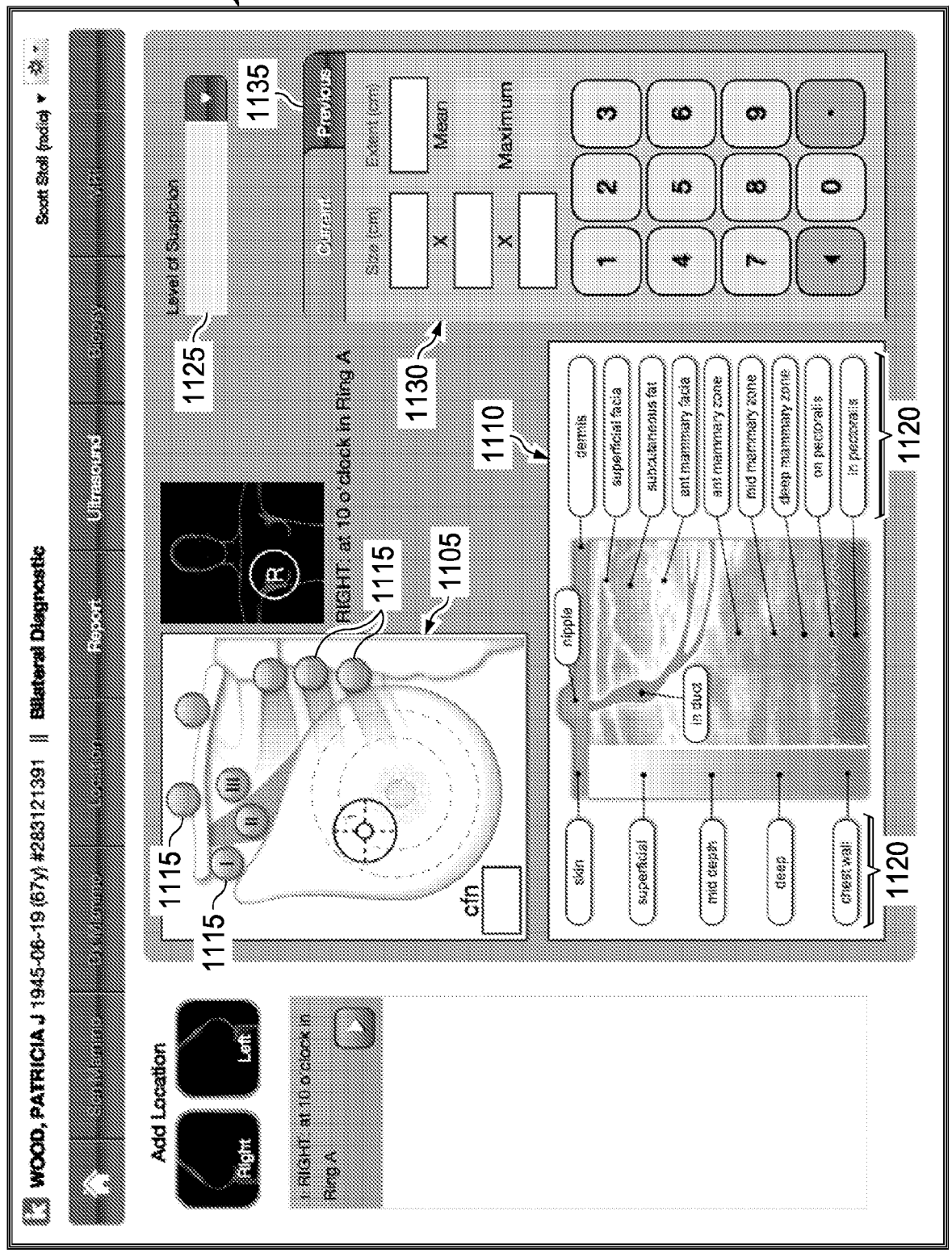
FIG. 21 illustrates an implementation of an example ultrasound graphical user interface.

In some implementations, the IMD system may generate GUIs corresponding to specific test results. For example, the IMD system may generate a GUI associated with ultrasounds, biopsy, and/or MRIs. FIG. 21 illustrates an implementation of an example ultrasound GUI 1100. As illustrated, the ultrasound GUI 1100 may allow an anatomical location to be provided and/or selected by a user. The ultrasound GUI 1100 may include one or more images that correspond to an anatomical location in patient test results. The images of anatomical locations in the ultrasound GUI may be representations of the anatomical image, rather than a photographic image and/or image from the patient test results. Since ultrasound scanning produces transverse views of an anatomical location, the ultrasound GUI 1100 may include a transverse view image (e.g., a schematic representation of a transverse view of an anatomical location). For example, the ultrasound GUI 1100 may include breast images, such as a first breast image (e.g., drawing) 1105 that includes representations of lymph nodes 1110 (e.g., proximate to the breast). As illustrated in FIG. 21, the first breast image 1105 may include level I, II, and/or III lymph nodes, other lymph nodes, the pectoral minor muscles and/or portions thereof. The ultrasound GUI 1100 may include breast images, such as a second breast image 1115 that illustrates a transverse view of the breast. The transverse view of the breast in the second breast image 1115 may allow a user to select an anatomical location based on relative location (e.g., skin, superficial, mid depth, deep, and/or chest wall) and/or anatomical location (e.g., dermis, subcutaneous fat, on pectoralis, duct, and/or nipple). A transverse view in conjunction with interpretation of ultrasound test results may allow more accurate locations to be selected by the user (e.g., because the ultrasound scans present a transverse view of an anatomical location) and/or may assist others in more accurately determining the location specified by the user. For example, a doctor performing a biopsy based on the location provided by the user may be more accurate due to the depiction using the first breast image 1105 and/or second breast image 1110. In some implementations, errors due to a user translating a location viewed on an ultrasound to a top or lateral view may be reduced by allowing location selection on a transverse view rather than and/or in addition to a lateral view.

A user may position a location indicator 1020 on one or more of the images 1105, 1110 on the ultrasound GUI. For example, the location indicator may be provided on a lymph node 1115 and/or one or more layers 1120 (e.g., relative depth and/or discrete region, such as in a duct, in subcutaneous fat, etc.) illustrated on the images 1105, 1110. Including a transverse view of an anatomical location may allow greater accuracy to be provided by a user providing a location, allow increased speed in providing an anatomical location since the user may not have to translate locations provided by the image in an ultrasound image to a side and/or top view (e.g., as opposed to a transverse view). The ultrasound GUI 1100 may include portions to provide a level of suspicion 1125 (e.g., independent of and/or in conjunction with a BI-RAD category) and/or sizes 1130 of lesions, masses, etc. The ultrasound GUI 1100 may allow information to be presented regarding previous patient test results 1135 such as size, level of suspicion, location, etc. The IMD system may retrieve the previous results from the patient record and/or a memory coupled to the IMD system.

In some implementations, the ultrasound GUI may be utilized independently and/or in conjunction with other GUI(s) generated by the system. For example, based on user properties, the IMD system may determine the GUI(s) to generate for presentation to the user.

In some implementations, a request for access to an ultrasound GUI, such as ultrasound GUI 1100, may be received. For example, a user may log into the IMD system and the IMD system may generate the ultrasound GUI. The ultrasound GUI may include breast images, such as a first breast image that includes representations of at least a portion of the lymph nodes proximate a breast and/or a breast image that includes a transverse view of the breast. The ultrasound GUI may include breast images such as the second breast image that includes a transverse view of the breast. The breast images may include a plurality of icons, such as location icons to denote relative location and/or anatomical location, such as lymph nodes and/or muscles. A user may select one or more locations via the location icons (e.g., select a side, select an anatomical location, and/or select a relative location). In some implementations, the user may select a BI-RAD category and/or level of suspicion to be associated with the selected location(s). The user may select and/or otherwise provide a dimension (e.g., size) to be associated with a characteristic (e.g., mass and/or calcification) in the test results via the GUI.

The selections provided by the user through the GUIs generated by the IMD system, such as selected icons (e.g., image icon(s) and/or text icon(s) such as association icon(s)) and/or anatomical location(s)), may be utilized by the IMD system to generate a report. The selections may be received via one or more GUIs generated by the IMD system, such as the work-list GUI, diagnosis GUI, location GUI, ultrasound GUI, etc. The report may include a diagnosis and/or be based at least partially on other information (e.g., patient history, exam history, user notes, follow-up tests to be recommended).

Figure 22:
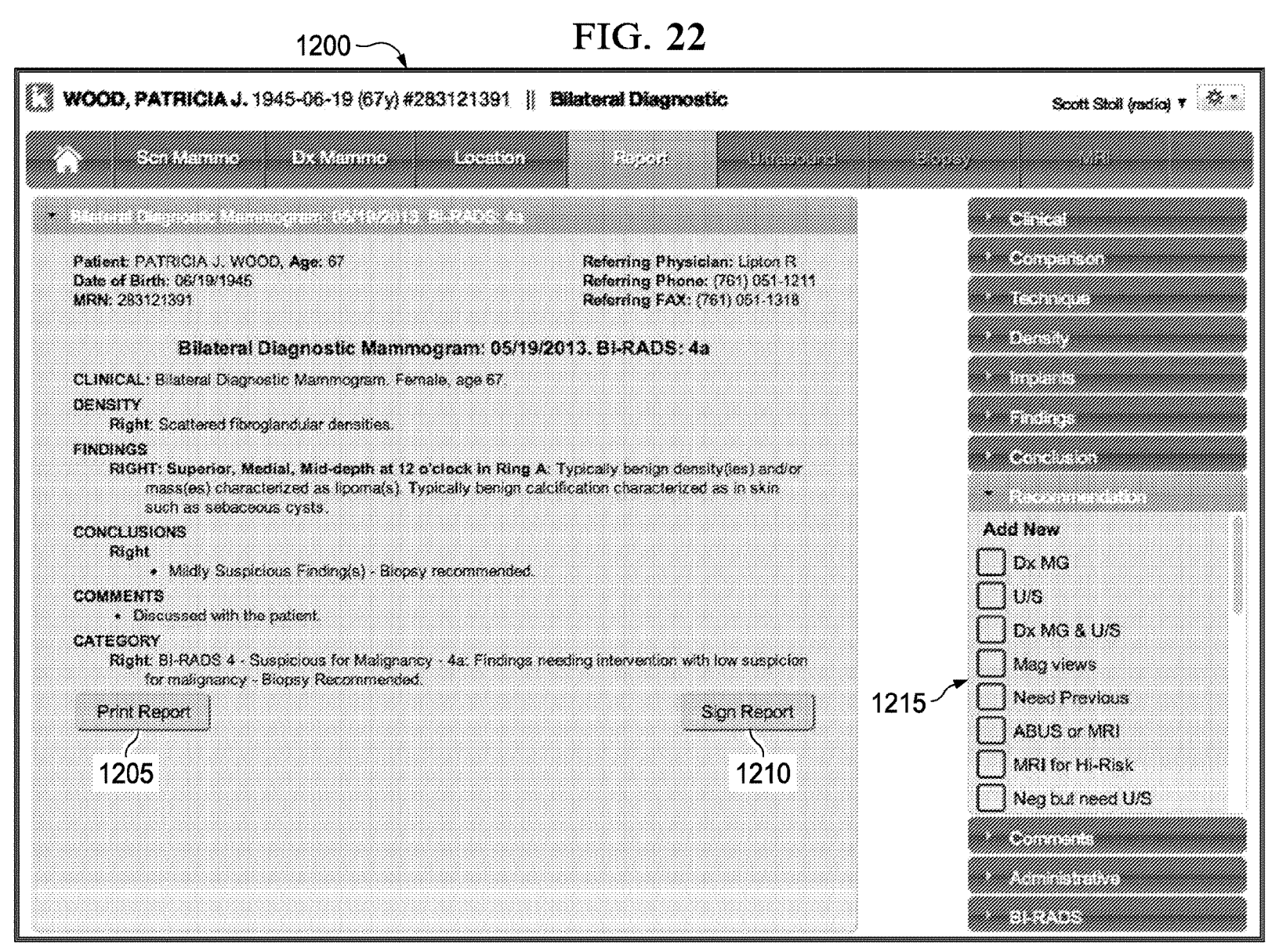

FIG. 22 illustrates an implementation of an example report GUI 1200. The report GUI 1200 may include diagnosis information such as a diagnosis. The IMD system may automatically generate the diagnosis information based on the selections provided by the user through the GUI(s), patient record(s), and/or government and/or industry standards. The report GUI 1200 may include may allow the diagnosis to be printed 1205 and/or signed 1210 by the user. For example, the report GUI may restrict transmission of the diagnostic report to, for example, an electronic medical record, a patient, and/or other physicians, prior to receiving approval (e.g., a signature) of a report by a user. The report GUI 1200 may allow additional information 1215 to be provided, for example, via one or more drop-down fields, tabs, etc. For example, the additional information 1215 may include information about additional testing, additional information needed to provide a diagnosis, comments, findings, etc.

The report may be generated concurrently with receiving the selections and/or when prompted by the user. For example, the user may select a report GUI tab and the report may be generated and/or presented to the user. In some implementations, a user may be inhibited from continuing to other portions of functionality of the IMD system without confirming (e.g., providing approval of) the diagnoses in the generated report. For example, the user may be restricted from enter diagnoses for other patients without confirming the diagnoses report generated by the IMD system. The user may be inhibited from logging out of the system until generated reports have been confirmed. In some implementations, a pop-up window, for example, may be presented to the user to remind the user that generated reports have or have not been confirmed. For example, the confirmation for generated reports reminder window may be presented to the user on a user device, such as the tablet displaying the GUI and/or via text message on a mobile phone. The confirmation for generated reports reminder window may be generated by the IMD system upon various triggers, such as user requesting access to GUI for a different patient, user requesting to log out, and/or passage of a predetermined period of time.

In some implementations, after the diagnostic report is confirmed by the user, the report and/or portions thereof may be automatically transmitted to one or more other parties (e.g., patients, physicians, other providers, and/or CDC or other agency). The IMD system may allow a user to create multiple reports that include different information from each other. For example, regulations (e.g., federal, community, state, and/or local) may govern what information is required to be transmitted to a patient. As another example, regulations may govern what information may not be transmitted (e.g., to the CDC such as patient identifying information). The IMD system may automatically include and/or restrict information in reports generated based at least in part on regulations. The IMD system may automatically include and/or restrict information in reports at least partially based on the identity of the person or entity that will receive the report. For example, reports may be generated including more detailed diagnosis information for referring physicians than reports generated for patients.

In some implementations, one or more of the generated GUIs may include default settings. Default settings may be based on user preferences and/or certain diagnoses, such as a negative result diagnosis. For example, a <no change> icon 125 may be automatically selected as a default setting and may indicate that no change has occurred since a previous diagnosis. The user may deselect (e.g., by touching or clicking) default settings, such as the <no change> icon, to change the default setting. In some implementations, default settings may be based at least partially on government and/or industry standards. For example, a user may be inhibited from signing a report when a breast density and/or BI-RADS® Category has not been provided.

Various portions of the IMD system and/or described processes may be utilized in conjunction with and/or independent of providing diagnoses of patient test results. For example, one or more features of the IMD system may be utilized to research characteristics, diagnoses, etc. The user may utilize the research in conjunction with analyzing a specific patient test result and/or independently. The IMD system may generate a GUI that includes image icons. A user may select an image icon and request one or more features of the IMD system. For example, a user may double-click or long-touch an image icon and a feature GUI, such as a pop-up window may be generated.

Figure 23:
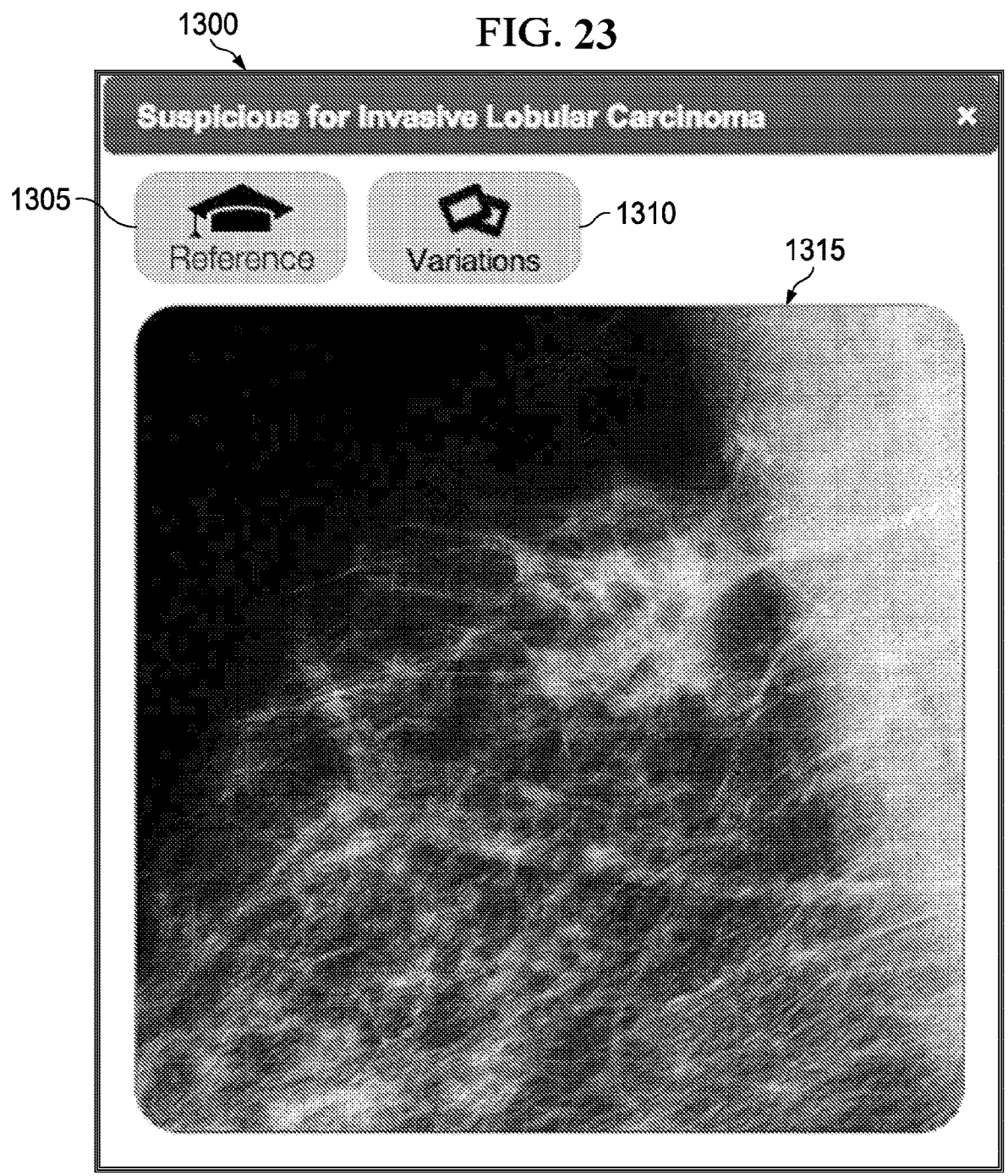
FIG. 23 illustrates an implementation of an example feature graphical user interface.

FIG. 23 illustrates an example of a feature GUI 1300. As illustrated, the feature GUI 1300 may include one or more icons through which features may be selected. For example, a user may request reference information related to the image icon using a <reference information> icon 1305 and/or variations in presentation of a characteristic in the image icon using a <variations> icon 1310. The feature GUI 1300 may include at least a portion of the photographic image in the selected image icon 1315.

In some implementations, the IMD system may allow a user to view variations in presentation of a characteristic included in an image icon. An expert, in some implementations, may select the image icons presented in a generated GUI. The GUI may initially display a selection of image icons based at least partially on user preferences, commonness of occurrence, type of medical image being analyzed, etc. A user may request more image icons (e.g., similar to a selected icon by selecting the <more other> icon and/or <more> image icons that include different presentations of similar diagnoses) through a feature GUI 1300. The IMD system may generate and/or display a different selection of image icons or other icons (e.g., one or more of the image icons may be different than the previously presented collection of image icons) based at least in part on the user request and/or parameters indicated in the user request. The user may or may not then select an image icon from the new selection of icons. The user may select among the image icons to select an image icon that may more accurately reflect a diagnosis or occurrence related to a diagnosis.

Figure 24:
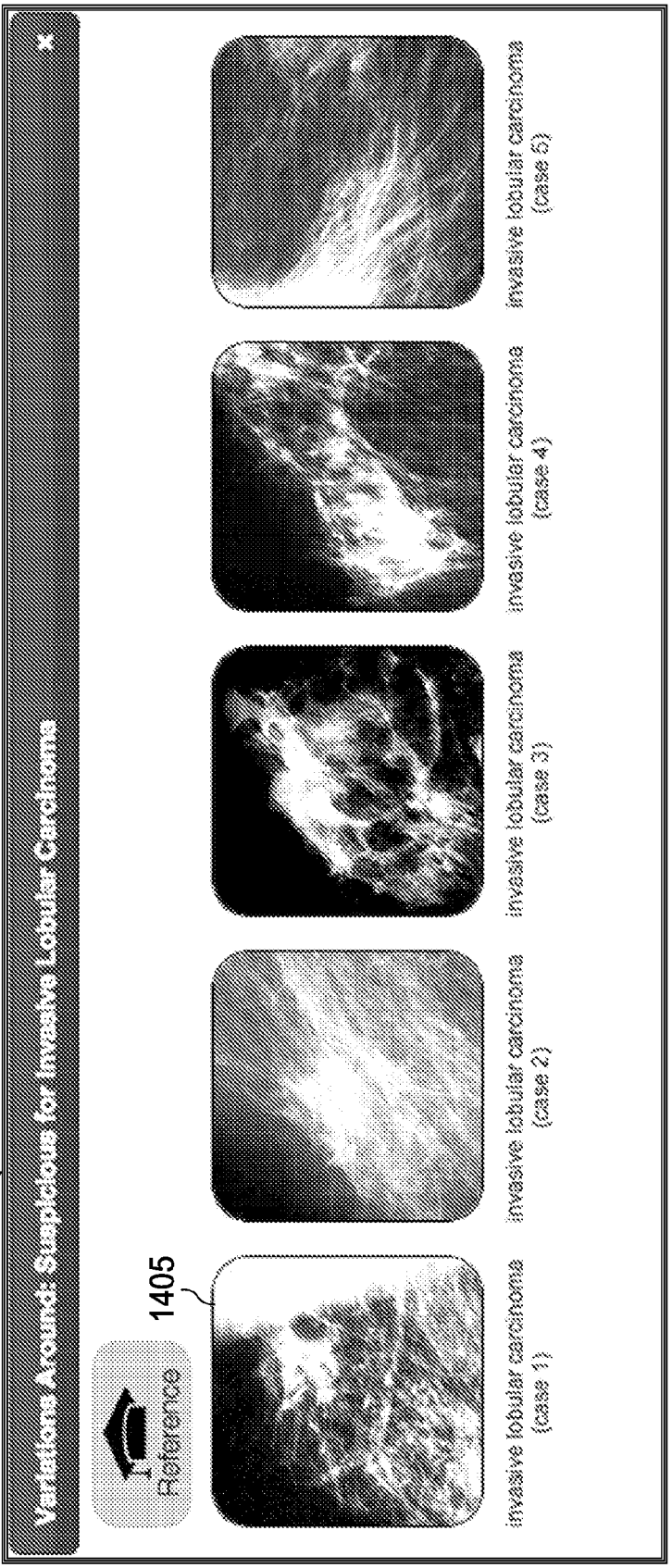
FIG. 24 illustrates an implementation of an example graphical user interface that presents variations of an image icon.

FIG. 24 illustrates an implementation of an example of GUI 1400 generated by the IMD system. The GUI 1400 includes variations 1405 in presentation of a characteristic in a selected image icon. For example, if a user selects a <variation> icon 1310 in the feature GUI 1300, then variations 1305 of the selected image icon may be presented through GUI 1400. The variations 1405 presented may be photographic images of different and/or similar presentations of a medical characteristic illustrated in a selected image.

Figure 25:
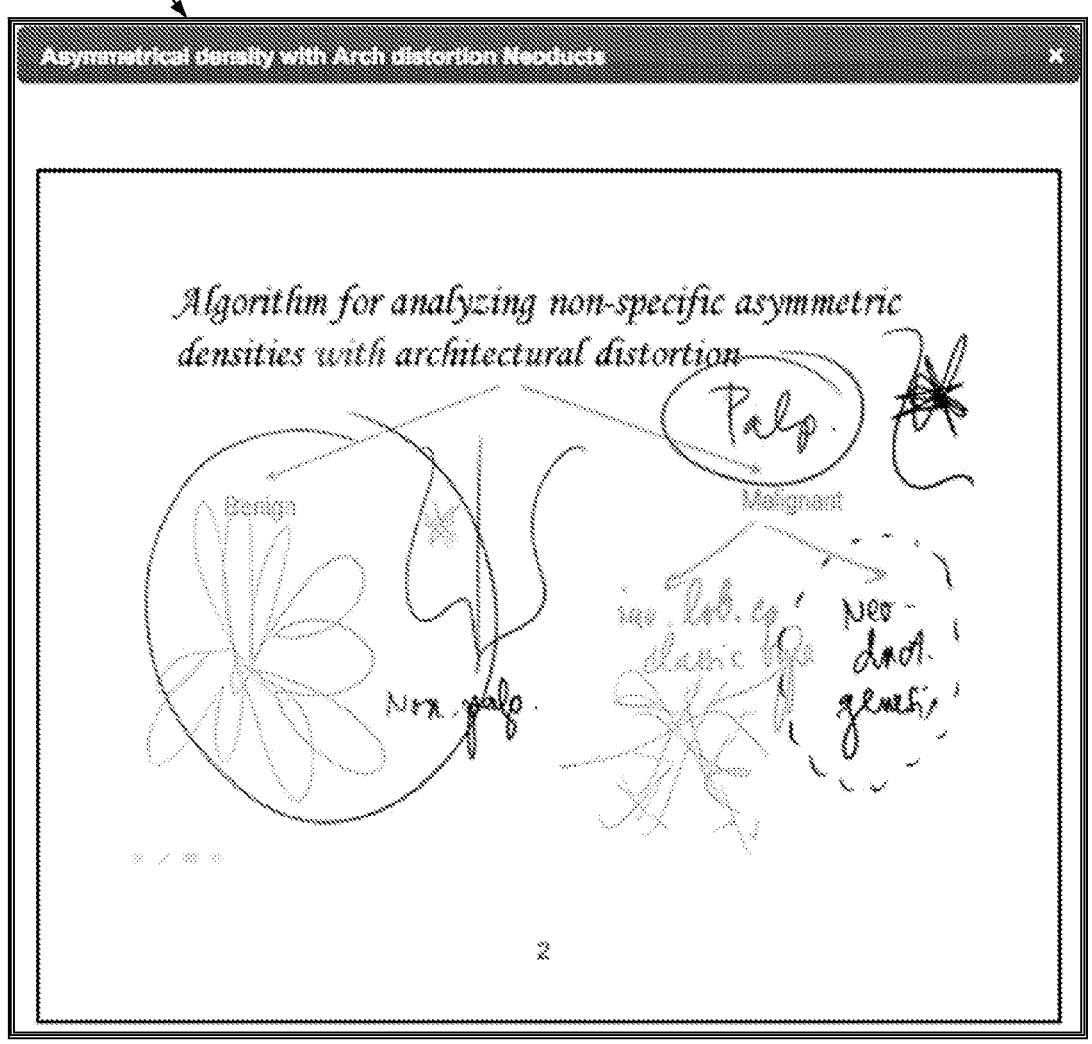
FIG. 25 illustrates an implementation of an example graphical user interface presenting a reference material.
Figure 19F:
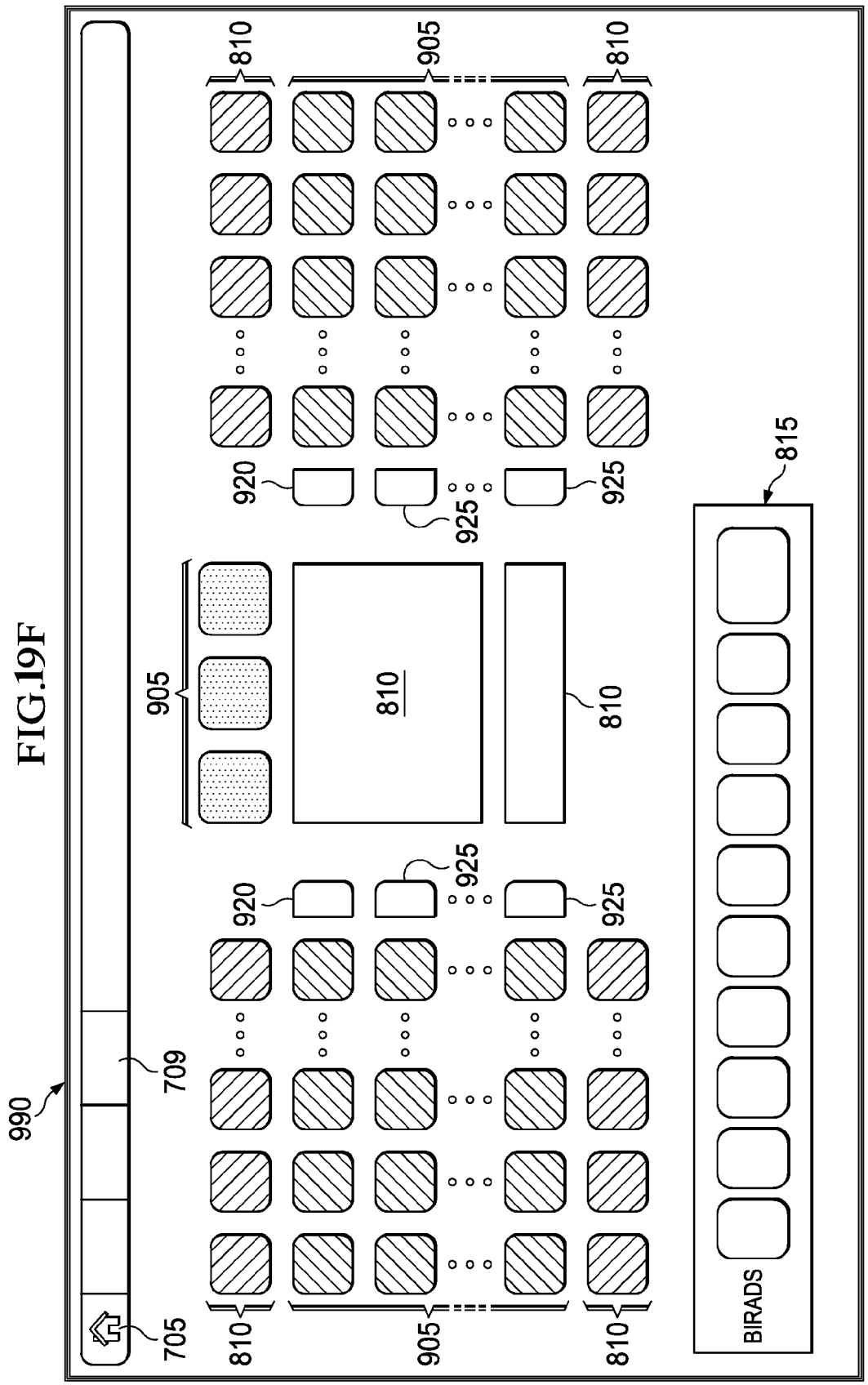

In some implementations, a user may select (e.g., by double-clicking and/or selecting the image icon and an additional icon, such as a reference icon 1305 in features GUI 1305) an image icon to obtain reference information about diagnoses and/or occurrences related to the image icon. FIG. 25 illustrates an example of a presentation 1500 of a reference material. As illustrated, a video related to an image icon is presented through a GUI generated by the IMD system. For example, during use, a user may be unsure of which image icon to select based on an analysis of a medical image of a patient. The user may select an image icon that appears similar to or approximately related to what the user views on a patient medical image, such as a PET scan. The user may select to view more image icons related to the selected image icon and/or to view reference material related to the image icon. In some implementations, a user may request reference material independently of the analysis of patient test results and/or patient records.

The GUI may retrieve and/or present reference material related to the image icon when requested by the user. The reference material may be correlated based on images and/or an indexed collection of a plurality of documents (e.g., expert opinions, journal articles, textbooks, etc.). By allowing the user to further research diagnoses related to the image icon using the GUI, the user's productivity may be increased and/or fatigue reduced due to decreased switching between right-brain and left-brain activity (e.g., because the user does not have to formulate key terms to search for information in a reference). The reference material collection may be searchable through key words and/or key word indexed, in some implementations. The collection of reference material may be updated at a central repository and users may access the updated information while utilizing the IMD system. Thus, the user may be able to access current information without lag times such as those commonly associated with receiving updates to reference textbooks and/or publications of new journal articles.

In some implementations, allowing the user to further research diagnoses related to an image icon may allow a user to research and/or diagnose an occurrence without knowing the appropriate key terms. For example, a user may see an occurrence in a medical image of a patient but not know what it is called or named. The user may select an image icon in the GUI that appears to be similar to the occurrence in the patient medical image. The user may then request more information about diagnoses related to the selected image icon and the GUI may retrieve and/or present reference material related to the selected image icon. The user may then confirm or deny suspicion about an occurrence and the diagnosis of the occurrence based on the presented research. Thus, a user may be able to more accurately provide diagnoses even without knowledge of the terms normally necessary to perform keyword-based search of references.

Although the IMA system, IMD system, diagnostic GUI(s) and/or analytical GUI(s) has been generally described in a medical environment (e.g., with medical images and/or medical diagnoses), the systems and processes described herein may be utilized with other expert images (e.g., test results) and diagnoses/analyses of the expert images. Expert images, such as test results, may include for example, CT scans, PET scans, MRI, radiographs, ultrasound, EEGs, EKGs, seismometers, seismic imaging systems, NMR, x-ray diffraction, GC, HPLC, skin lesions, dermatology findings, endoscopy findings, ophthalmology findings, pathological specimens including microscopic images, photographs, forensic images, and/or any other appropriate images. The system (e.g., IMA system and/or IMD system) and/or processes may generate a GUI to facilitate entry of diagnostic/analyses of the expert images and/or generate reports based on the diagnoses/analyses (e.g., for clients, for government agencies, and/or for billing).

For example, the system and/or processes may be utilized with expert images related to seismology and/or geology. Expert images presented to a user may include seismometer results and the user may provide analysis information through a GUI generated by the systems and/or processes described. The GUI may include image icons that correlate to typical patterns in a seismic image. For example, the image icons may be portions of a seismic image. The user may select an image icon to provide an analysis of a seismic image that the user is analyzing. If a user needs additional information (e.g., to facilitate analysis of the seismic image), the user may request more information about an image icon (e.g., by selecting an image icon and another icon or by double clicking an image icon). The system may retrieve and/or present to the user additional information such as seismology related expert opinions, reference materials, journal articles, etc. The system may generate a GUI to present the additional information to the user. The user may then utilize the system to select image icon(s) as an analysis of an expert image. The system may generate one or more reports (e.g., analysis reports, reports to government agencies, and/or billing reports) based on the selected image icon(s) and/or the corresponding analysis. The system may collect data based on the analysis entered by the user (e.g., performance statistics and/or reporting requirements for licensing). Probabilities of an outcome (e.g. presence or absence of petroleum within a geological location) may also be calculated and presented in the GUI utilizing system(s), process(es), and/or portions thereof similar to the described IMD system(s) and process(es) related to determining the probability of an outcome, such as malignancy in a medical environment.

As another example, the system and/or processes may be utilized with expert images related to structural analysis. Expert images may include x-ray and/or ultrasound images of structures and/or portions thereof (e.g., rebar positions, pier locations, column positions, and/or tendons in pre-stressed concrete). The expert images may be presented to a user. The system may generate a GUI that includes image icons and/or other icons for presentation to a user. The GUI may facilitate entry of an analysis of the expert images presented to the users. The system may communicate with other commercially available software (e.g., software for displaying images, analysis software, and/or computer aided design software). The system may transmit and/or retrieve information from the commercially available software and the information and/or portions thereof may be presented to the user through the GUI. For example, the system may determine communicate with commercially available image viewing software to ensure that the GUI generated is cor-related to the appropriate case (e.g., the same case as associate with the expert image being viewed). The user may select image icon(s) and/or other icons that correspond to an analysis of the expert image(s) that the user is viewing. The user may also request more information about the image icon(s) and the system may retrieve reference material related to the image icon(s) selected. The reference material may assist the user in analyzing the expert images being analyzed by the user, in some implementations. Report(s) may be generated based on selected image icon(s) and/or other icon(s).

As another example, the systems and/or processes may be utilized with chemical analysis. The expert images may include results associated with gas chromatography, mass spectrometry, liquid chromatography, nuclear magnetic resonance, infrared analysis, and/or other appropriate images. The user may request access to a GUI of the system. The system may generate a GUI appropriate for the expert image being analyzed by the user. The GUI may include image icon(s) and/or other icon(s). The user may select image icon(s) and/or other icon(s) for selection in providing an analysis and/or to request additional information. Additional information, such as reference material (e.g., journal articles and/or expert images), may be presented to the user and/or may assist the user in selecting an appropriate analy-sis (e.g., and corresponding image icon(s)) for an expert image. Report(s) (e.g., to clients, to government agencies, and/or billing) may be generated based on the selection of image icon(s) and/or other icon(s). Various data may be tracked and/or stored by the system (e.g., dates analysis was performed, dates compounds were identified, user statistics, and/or billing statistics).

In some implementations, the various system(s) and/or processes may be utilized in forensic sciences. For example, a user may view expert images that include test results and provide analysis information through various GUIs. The system may generate reports, as appropriate.

In some implementations, various systems and/or pro-cesses may be utilized in astronomy. The expert images may include images (e.g., visible light based, electromagenetic radiation based, and/or neutrino based) of celestial bodies, for example. A user, such as an astronomer may view an expert image of an unknown area and analyze the expert image. The user may utilize GUIs generated by the system to enter in the analysis. The user utilize the image icons to facilitate entry of the analysis into the GUI and/or to assist in the analysis of the GUI. For example, if the user does not know the appropriate analysis or image icon to select, the user may request more information about a similar image icon and the system may retrieve and/or present the addi-tional information (e.g., reference materials) to the user.

Although several environments in which the IMA system and/or processes may be utilized have been described, the IMA systems and/or processes may be utilized in other environments, as appropriate.

In various implementations, the IMA system may include a computer system coupled to user device(s), one or more repositories, and/or third party system(s) via a network, such as the Internet. A user may view expert images, such as test results, via a third party system, on a user device. The user may provide an analysis of the presented test results via GUI(s) generated by the IMA system. For example, the IMA system may include one or more modules, stored on a memory of the IMA system and executable by a processor of the IMA system. The modules of the IMA system may validate user credentials, provide access to the IMA system, generate analytical graphical user interfaces, receive selec-tions from a user via GUI(s), generate report(s) based on selection(s), monitor information (e.g., user information, metrics, and/or other information), etc. The IMA system may include an article that includes a machine-readable medium that stores instructions for generating analytical reports. The instructions may be operable to cause data processing apparatus to perform operations comprising one or more of the described operations.

In various implementations, the IMA system may gener-ate an analytical graphical user interface comprising a plurality of image icons. A selection of image icon(s) may be received and a report may be automatically generated based on the selected image icon(s).

Implementations may include one or more of the follow-ing features. User information may be received (e.g., user credentials). The IMA system may determine whether to allow access to at least portions of the IMA system based at least partially on the provided user information. A record may be selected (e.g., a record associated with a test results). For example, the IMA system may generated a work-list (e.g., via a GUI) that includes records associated with test results to be analyzed. A user may select a record from the listing of records in the work-list. A request for test results to be presented on a user device via a third party system (e.g., commercially available software for viewing expert images) may be transmitted. In some implementations, the IMA system may determine whether a selected record is associated with test results presented to the user via third party software (e.g., by communicating via one or more application interfaces with at least a portion of the third party software). One or more analytical GUI(s) may be generated. For example, abbreviated analytical GUI(s), analytical GUI(s) related to a type of test result (e.g., ultrasound and/or NMR), and/or other types of analytical GUI(s) may be generated by the IMA system. In some implementations, the IMA system may allow and/or restrict selection of icons presented on the GUI (e.g., selection of predetermined types of icons may be restricted prior to receiving input, such as a location or other information). One or more of the gener-ated GUIs may include image icons. The image icons may include a photographic image, such as a photographic image of an example of a characteristic (e.g., a characteristic of a result of an analysis, information related to a conclusion in an analysis, and/or other information related to an analysis). In some implementations, reports generated by the IMA system may include analytical reports, billing reports, metric reports, compliance reports, etc. The reports may be generated based on selections received through the GUI(s) generated by the IMA system and/or other information. In some implementations, one or more indicia (e.g., for image icons and/or locations) may be provided based on a previously generated report for the same record (e.g., patient, test subject, etc.). The IMA system may monitor properties of the user, store monitored properties, determine one of more metrics based on one or more monitored properties, and/or generate reports and/or notifications based on the metrics and/or monitored properties. The IMA system may receive follow-up information, such as outcomes (e.g., oil found at a location) and correlate the follow-up information to generated reports to determine metrics, such as probability of outcomes based on selection of one or more image icons. In some implementations, variations in presentation of a characteristic in an image icon may be requested by a user, retrieved, and/or presented to the user via GUI(s) generated by the IMA system.

In various implementations, the IMA system may include image-indexed references. The image-indexed references may be accessed independently and/or while providing analysis information through GUI(s) generated by the IMA system. For example, references may be correlated through one or more associations to image icons (e.g., in a similar manner as described in a medical environment). A request for reference information associated with at least one image icon of a GUI generated by the IMA system may be received, and reference information (e.g., a set of reference materials) may be retrieved from a memory, such as a database, coupled to the IMA system. The reference information may be indexed based on a first relation or association to an image icon. The reference information may be indexed based on a second relation to other references and/or other icons (e.g., similar presentations of characteristics and/or commonly confused analyses).

Although several operations performed by the IMA system have been described, other operations, such as described operations performed by the IMD system as appropriate in the environment in which the IMA is operating.

In various implementations, an analytical graphical user interface may be generated that includes a plurality of image icons. Each image icon may include a photographic image of an example of a characteristic. The analytical graphical user interface may generate one or more analyses related to one or more test results. A selection of image icon(s) related to analyzing test results may be received, and a report may be automatically generated that includes at least a portion of an analysis for test results based on at least one of the selected image icons.

Implementations may include one or more of the following features. The test results may include patient test results, and at least one of the analyses may include a diagnosis. One or more locations may be received via the generated graphical user interface, and a received anatomic location may identify at least a portion of a patient presented in at least one of the patient test results. The selected image icon(s) may be associated with at least one of the received locations. In some implementations, the test results may include patient test results, and at least one of the analyses may include a diagnosis. The image icon(s) may include a characteristic image icon that includes at least a portion of a photographic image associated with a medical characteristic. The image icon(s) may include breast density image icon(s) that include at least a portion of a photographic image associated with breast density. In some implementations, one or more indicia may be provided for one or more image icons based on a previously generated report for a record, where the test results are related to the record. The test results may include patient test results. In some implementations, at least one of the analyses may include a diagnosis, and one or more indicia may be generated based on a previously generated report for a patient. Each indicia may indicate an anatomic location in the patient, in some implementations. Properties of a user may be monitored and/or stored. Reports may be generated based on the monitored properties of the user. In some implementations, images of variations of the characteristic in the photographic image of an image icon may be retrieved based at least partially on the image icon selected. The image icons may include at least a portion of one or more CT scans, one or more mammograms, one or more radiographs, one or more MRI scans, one or more PET scans, one or more ultrasounds, and/or one or more other medical imaging exams. A number of image icons included on at least one of the generated graphical user interfaces may be automatically generated based at least partially on a screen dimension of a user device, where the graphical user interface is generated for presentation on the user device. At least one of the graphical user interfaces may include association icon(s), and at least one of the association icons may indicate a relationship between two or more selected image icons. Automatically generating a report may include retrieving one or more templates including words that include a diagnosis based on one or more of the selected image icons and one or more of the association icons. In some implementations, billing codes may be automatically generated based on at least one of the selected image icons or selected text icons of at least one of the graphical user interfaces.

In various implementations, one or more graphical user interfaces may be generated that include a plurality of image icons. Each image icon may include a photographic image of an example of a characteristic. At least one of the graphical user interfaces may facilitate generation of one or more analyses related to one or more test results. A selection of the image icon(s) related to analyzing test results, and a request for reference information associated with at least one of the selected image icons may be received. Reference information may be retrieved from a memory, such as a database. The reference information may be indexed based on relation to an image icon in the plurality of image icons.

Implementations may include one or more of the following features. A report that includes at least a portion of an analysis for test results ay be automatically generated based on at least one of the selected image icons. At least a portion of the retrieved reference information may be presented to a user. User properties may be monitored, and a listing of reference materials may be retrieved based at least partially on at least one of the monitored user properties.

In various implementations, an image based analytical system may include a report module and a memory. The report module may generate an analytical graphical user interface that includes a plurality of image icons, receive a selection of one or more of the image icons related to analyzing test results; and automatically generate a report that includes at least a portion of an analysis for test results based on at least one of the selected image icons. Each image icon may include a photographic image of an example of a characteristic, and the analytical graphical user interface may generate one or more analyses related to one or more test results. The memory may include template(s), and each template includes words that include at least a portion of an analysis based on one or more of the selected image icons.

Implementations may include one or more of the following features. The report module may determine one or more metrics. The report module may receive one or more follow up test results for a plurality of records, and may determine outcome(s) based on received image icon selections for the plurality of records and the received follow-up test results. The report module may communicate with a third party system such that test results are retrieved by the third party system.

In various implementations, a diagnostic graphical user interface may be generated that is related to patient test result(s) presented to a user via a third party interface. The graphical user interface may include image icon(s), and each image icon may include at least a portion of a medical photographic image of an example characteristic. Anatomical location(s) may be received via the generated graphical user interface, and a received anatomic location may identify at least a portion of a patient presented in at least one of the patient test results. A selection of the image icon(s) to associate with at least one of the received locations may be received. The image icons may be related to diagnosing patients. A report may be automatically generated that includes at least a portion of a diagnosis for a patient based at least partially on at least one of the selected image icons.

Implementations may include one or more of the following features. The diagnostic graphical user interface may include a breast imaging diagnostic graphical user interface, and the report may include at least a portion of the diagnosis of the patient based on breast imaging. The image icon(s) may include at least a portion of at least one of one or more CT scans, one or more mammograms, one or more radiographs, one or more MRI scans, one or more PET scans, one or more ultrasounds, and/or one or more other medical imaging exams. In some implementations, a selection of one or more image icons may be restricted when at least one anatomic location has not been received. A number of image icons included on the generated graphical user interface may be automatically adjusted based at least partially on a screen dimension of a user device, where the graphical user interface is generated for presentation on the user device. The graphical user interface may include text icon(s). A selection of an adjustment text icon may be received from a user, and the number of image icons included on the graphical user interface may be adjusted based on the received selection. One or more indicia may be generated based on a previously generated report for a patient. Each indicia may indicate at least one of an anatomic location in the patient and/or one or more image icons. In some implementations, one or more follow up test results may be received for a plurality of patients, and outcome(s) may be determined based at least partially on received image icon selections for the plurality of patients and the received follow-up test results. In some implementations, a selection of image icon(s) may be received for a new patient, and a probability of an outcome may be determined based on one or more of the received selections of image icons for the new patient and the previously determined outcomes. The graphical user interface may include association icon(s). At least one of the association icons may indicate a relationship between two or more selected image icons. Automatically generating a report may include retrieving template(s) that include words that include a diagnosis based on the selected image icon(s) and/or the association icon(s).

In various implementations, diagnostic graphical user interface(s) related to patient test results presented to a user via a third party interface may be generated. The graphical user interfaces may include image icon(s), and each image icon may include at least a portion of a medical photographic image of an example characteristic. At least one of the graphical user interfaces may include first diagnostic graphical user interfaces, and/or second diagnostic graphical user interfaces. The first diagnostic graphical user interfaces and/or the second diagnostic graphical user interface(s) may include anatomic location icon(s) and/or diagnostic text icons. Each anatomic location icon may indicate one or more locations on a patient. Each diagnostic icon may be associated with at least a portion of a diagnosis. At least one of the image icons of the first diagnostic graphical user interface may include a breast density image icon, and each breast density image icon includes at least a portion of a photographic image associated with breast density. At least one of the image icons of the second graphical user interface(s) may include breast density image icon(s) (e.g., that includes at least a portion of a photographic image associated with breast density) and/or lesion characteristic image icon(s) that include at least a portion of a photographic image associated with a medical characteristic of a lesion. Anatomical locations may be received via the generated graphical user interface(s), and each anatomic location may indicate at least a portion of a patient presented in at least one of the patient test results. A selection of image icon(s) to associate with at least one of the received locations may be received that is related to a diagnosis based at least partially on the presented patient test results, and a report may be automatically generated that includes at least a portion of a diagnosis for a patient based on at least one of the selected image icons.

Implementations may include one or more of the following features. A request from a user for a diagnostic graphical user interface may be received, and the first graphical diagnosis graphical user and/or the second diagnostic graphical user interface may be generated based at least partially on the request. A third diagnostic graphical user interfaces may include breast images, such as a first breast image that includes a representation of lymph nodes proximate a breast and/or a second breast image that includes a transverse view of a breast. A selection of a anatomic location on at least one of the breast images may be received, and the generated report may be based at least partially on the selection(s) in the third diagnostic graphical user interfaces. A determination may be made whether one or more locations have been received, and selections in one or more of the graphical user interfaces may be restricted if a determination is made that one or more locations have not been received. Billing codes may be automatically generated based on the image icon(s) selected and/or text icon(s) selected. Follow up information for a patient may be received and compared with the image icons previously selected for the patient. Metric(s) of a user may be determined based on the comparison, and at least one of the determined metrics of the user may be monitored.

In various implementations, an image based medical diagnostic system may include a report module and a memory. The report module may generate a graphical user interface related to patient test results that is presented to a user via a third party interface. The graphical user interface may include image icons, and each image icon may include at least a portion of a medical photographic image of an example characteristic. The report module may receive anatomical locations via the generated graphical user interface, and an anatomic location may indicate at least a portion of a patient presented in at least one of the patient test results. The report module may receive a selection of image icon(s) to associate with at least one of the received locations related to a diagnosis based at least partially on the presented patient test results, and may automatically generate a report that includes at least a portion of a diagnosis for a patient based at least partially on the selected image icon(s) and/or the template(s). A memory may include one or more templates, and each template may include words that include at least a portion of a diagnosis based on one or more of the selected image icons.

Implementations may include one or more of the following features. The report module may communicate with a third party system such that a patient test results are retrieved by the third party system. The image based medical diagnostic system may include a reference module that retrieves reference(s) based at least partially on an image icon selected. The reference module may retrieve image(s) of variations based at least partially on a image icon selected.

In various implementations, a graphical user interface, for presentation on a user device, may be generated. The graphical user interface may include a plurality of image icons, and each image icon may include at least a portion of a medical photographic image of an example characteristic. A selection of one or more of the image icons and a request for reference information associated with at least one of the selected image icons may be received. A first set of reference information may be retrieved from a memory, such as a database, based at least partially on at least one of the selected image icons. The reference information in the memory may be indexed based at least partially on one or more relationships to one or more of the image icons.

Implementations may include one or more of the following features. At least a portion of the retrieved reference information may be presented on the user device. In some implementations, a second set of reference information may be retrieved based on a secondary association. The secondary association may relate reference(s) in the second set of reference information with the first set of reference information and/or one of the selected image icons. At least a portion of the second set of reference information may be presented to a user. At least one of the image icons may include: characteristic image icon(s) that includes at least a portion of a photographic image associated with a medical characteristic; and/or breast density image icon(s) that include at least a portion of a photographic image associated with breast density. The generated graphical user interface may include association icons. A selection of association icon(s) may be received, and the first set of information may be retrieved based at least partially on the selected image icons and at least one of the selected association icons. The graphical user interface generated may be related to patient test result(s) presented to a user via a third party interface. In some implementations, anatomical location(s) may be received via the generated graphical user interface, where a anatomic location indicates at least a portion of a patient presented in at least one of the patient test results; a selection of image icon(s) to associate with at least one of the received anatomical locations may be received related to a diagnosis based at least partially on the presented patient test results; and, a report may be automatically generated that includes at least a portion of a diagnosis for a patient based on at least one of the selected image icons. Follow-up information may be received for one or more patients and compared with image icon(s) previously selected for each of the patients. Errors based on a comparison of the follow up information and the image icons previously selected may be determined, and a third set of reference information may be identified based at least partially on the determined errors and/or the previously selected image icons associated with the determined errors. In some implementations, an error notification to a user based on the determined errors, wherein the error notification comprises a listing of the identified third set of reference information.

In various implementations, a graphical user interface may be generated that includes a plurality of image icons for presentation to a user. Each image icon may include at least a portion of a medical photographic image of an example of a characteristic. A selection of image icon(s) and a request for reference information associated with at least one of the selected image icon(s) may be received. A first set of reference information may be retrieved from a memory, such as a database, based at least partially on the selected image icons. Reference information in the database may be indexed based on relation to an image icon in the plurality of image icons.

Implementations may include one or more of the following features. At least a portion of the retrieved reference information may be presented on the user device. Image icons may include: a characteristic image icon that includes at least a portion of a photographic image associated with a medical characteristic; and/or a breast density image icon that includes at least a portion of a photographic image associated with breast density. The graphical user interface may include a plurality of other icons related to one or more diagnoses. A selection of one or more other icons and a request for reference information associated with at least one of the selected other icons may be received. A second set of reference information may be retrieved from a memory, such as a database, based on at least one of the selected other icons. The reference information in the database may be indexed based on relation to an other icon. The generated graphical user interface may include: breast images and/or other icons associated with breast images. The breast images may include a first breast image that includes a representation of a breast and lymph nodes proximate the breast, and a second breast image that includes a transverse view of the breast. A selection of an anatomic location on at least one of the breast images and selection of one or more other icons may be utilized to generate a diagnosis. In some implementations, a selection of at least one other icon and a request for reference information associated with at least one of the selected other icons may be received; and a second set of reference information may be retrieved from a memory, such as a database, based on at least one of the selected other icons. Reference information in the database may be indexed based on relation to an other icon. In some implementations, a listing of the first set of references may be generated and presented to a user. A selection of a reference from the listing may be received, and the selected reference may be retrieved.

In various implementations, an image indexed reference system may include a memory and an image-indexing module. The memory may store reference information and association(s) between reference information and image icon(s) in a graphical user interface that includes a plurality of image icons for presentation to a user. Each image icon may include at least a portion of a medical photographic image of an example of a medical characteristic. The image-indexing module may receive a selection of image icon(s) from the graphical user interface and a request for reference information associated with at least one of the image icons. The image-indexing module may determine a first set of reference information associated with the selected image icon based on at least one of the stored associations, and retrieve at least a portion of the first set of reference information from the memory.

Implementations may include one or more of the following features. The memory may store secondary associations between the reference information and the image icons. The image-indexing module may transmit a notification to the user based on the secondary association and the selected image icons, and retrieve at least a portion of a second set of reference information based at least partially on the secondary associations. The secondary associations may include related characteristics, similar characteristics, and/or misdiagnosed related characteristics. The image-indexing module may present at least a portion of the first set of reference information from the memory. The memory may store one or more variation images, The image-indexing module may receive a request for one or more variation images, and retrieve variation image(s) associated with at least one of the selected image icons. The information may include one or more expert verified references.

An image-based analysis may facilitate the formation of an analysis and/or entry of an analysis by a user. An analytic graphical user interface (GUI) may include image icon(s), which may include a photographic image.

For example, in some implementations the analytic graphical user interface may be utilized in a medical environment. The image based diagnostic system (e.g., analytic graphical user interface) may facilitate the process of forming a diagnosis through the use of an image based graphical user interface. A user, such as a physician, may view electronic and/or digitized test results through commercially available software. The image based diagnostic system may streamline the process of recording diagnoses through a graphical user interface that includes image icons. The selection of image icons may automatically generate reports and related data may be tracked, as appropriate.

In some implementations, a user may utilize the image based graphical user interface to research topics. A user may select an image icon and references related to the image icon may be retrieved and presented to the user. Allowing a user to search through a plurality of references by selecting an image may allow the user to further research topics while lacking knowledge of the appropriate search term and/or more quickly research topics by reducing the time spent formulating appropriate keywords for queries.

In various implementations, a diagnostic graphical user interface may be generated that is related to patient test result(s) presented to a user via a third party interface. The graphical user interface may include image icon(s), and each image icon may include at least a portion of a medical photographic image of an example characteristic. Anatomical location(s) may be received via the generated graphical user interface, and a received anatomic location may identify at least a portion of a patient presented in at least one of the patient test results. A selection of the image icon(s) to associate with at least one of the received locations may be received. The image icons may be related to diagnosing patients. A report may be automatically generated that includes at least a portion of a diagnosis for a patient based at least partially on at least one of the selected image icons.

Implementations may include one or more of the following features. The diagnostic graphical user interface may include a breast imaging diagnostic graphical user interface, and the report may include at least a portion of the diagnosis of the patient based on breast imaging. The image icon(s) may include at least a portion of at least one of one or more CT scans, one or more mammograms, one or more radiographs, one or more MRI scans, one or more PET scans, one or more ultrasounds, and/or one or more other medical imaging exams. In some implementations, a selection of one or more image icons may be restricted when at least one anatomic location has not been received. A number of image icons included on the generated graphical user interface may be automatically adjusted based at least partially on a screen dimension of a user device, where the graphical user interface is generated for presentation on the user device. The graphical user interface may include text icon(s). A selection of an adjustment text icon may be received from a user, and the number of image icons included on the graphical user interface may be adjusted based on the received selection. One or more indicia may be generated based on a previously generated report for a patient. Each indicia may indicate at least one of an anatomic location in the patient and/or one or more image icons. In some implementations, one or more follow up test results may be received for a plurality of patients, and outcome(s) may be determined based at least partially on received image icon selections for the plurality of patients and the received follow-up test results. In some implementations, a selection of image icon(s) may be received for a new patient, and a probability of an outcome may be determined based on one or more of the received selections of image icons for the new patient and the previously determined outcomes. The graphical user interface may include association icon(s). At least one of the association icons may indicate a relationship between two or more selected image icons. Automatically generating a report may include retrieving template(s) that include words that include a diagnosis based on the selected image icon(s) and/or the association icon(s).

In various implementations, diagnostic graphical user interface(s) related to patient test results presented to a user via a third party interface may be generated. The graphical user interfaces may include image icon(s), and each image icon may include at least a portion of a medical photographic image of an example characteristic. At least one of the graphical user interfaces may include first diagnostic graphical user interfaces, and/or second diagnostic graphical user interfaces. The first diagnostic graphical user interfaces and/or the second diagnostic graphical user interface(s) may include anatomic location icon(s) and/or diagnostic text icons. Each anatomic location icon may indicate one or more locations on a patient. Each diagnostic icon may be associated with at least a portion of a diagnosis. At least one of the image icons of the first diagnostic graphical user interface may include a breast density image icon, and each breast density image icon includes at least a portion of a photographic image associated with breast density. At least one of the image icons of the second graphical user interface(s) may include breast density image icon(s) (e.g., that includes at least a portion of a photographic image associated with breast density) and/or lesion characteristic image icon(s) that include at least a portion of a photographic image associated with a medical characteristic of a lesion. Anatomical locations may be received via the generated graphical user interface(s), and each anatomic location may indicate at least a portion of a patient presented in at least one of the patient test results. A selection of image icon(s) to associate with at least one of the received locations may be received that is related to a diagnosis based at least partially on the presented patient test results, and a report may be automatically generated that includes at least a portion of a diagnosis for a patient based on at least one of the selected image icons.

Implementations may include one or more of the following features. A request from a user for a diagnostic graphical user interface may be received, and the first graphical diagnosis graphical user and/or the second diagnostic graphical user interface may be generated based at least partially on the request. A third diagnostic graphical user interfaces may include breast images, such as a first breast image that includes a representation of lymph nodes proximate a breast and/or a second breast image that includes a transverse view of a breast. A selection of a anatomic location on at least one of the breast images may be received, and the generated report may be based at least partially on the selection(s) in the third diagnostic graphical user interfaces. A determination may be made whether one or more locations have been received, and selections in one or more of the graphical user interfaces may be restricted if a determination is made that one or more locations have not been received. Billing codes may be automatically generated based on the image icon(s) selected and/or text icon(s) selected. Follow up information for a patient may be received and compared with the image icons previously selected for the patient. Metric(s) of a user may be determined based on the comparison, and at least one of the determined metrics of the user may be monitored.

In various implementations, an image based medical diagnostic system may include a report module and a memory. The report module may generate a graphical user interface related to patient test results that is presented to a user via a third party interface. The graphical user interface may include image icons, and each image icon may include at least a portion of a medical photographic image of an example characteristic. The report module may receive anatomical locations via the generated graphical user interface, and an anatomic location may indicate at least a portion of a patient presented in at least one of the patient test results. The report module may receive a selection of image icon(s) to associate with at least one of the received locations related to a diagnosis based at least partially on the presented patient test results, and may automatically generate a report that includes at least a portion of a diagnosis for a patient based at least partially on the selected image icon(s) and/or the template(s). A memory may include one or more templates, and each template may include words that include at least a portion of a diagnosis based on one or more of the selected image icons.

Implementations may include one or more of the following features. The report module may communicate with a third party system such that a patient test results are retrieved by the third party system. The image based medical diagnostic system may include a reference module that retrieves reference(s) based at least partially on an image icon selected. The reference module may retrieve image(s) of variations based at least partially on a image icon selected.

One or more of the described operations may be performed by data processing apparatus, where an article that includes a machine-readable medium stores instructions operable to cause the data processing apparatus to perform the described operations.

Although users have been described as a human, a user may be a person, a group of people, a person or persons interacting with one or more computers, and/or a computer system. Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

In various implementations, module(s) of the IMD system and/or IMA system, such as the diagnosis module may perform one or more of the operations as described in FIGS. 12-25.

One or more of the processes illustrated in FIGS. 12-25 or portions thereof may be implemented by various systems, such as the systems described in FIGS. 10 and/or 11. In addition, various operations of FIGS. 12-25 or portions thereof may be added, deleted, and/or modified.

These computer programs (also known as programs, software, software applications or code) include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a track pad) by which the user can provide input to the computer. Other kinds of devices can be used to provide for interaction with a user as well; for example, feedback provided to the user by an output device can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other. Updates to the IMD system may be pushed to clients via a network.

Example 1

The below described example lists several components, features, benefits, and/or processes. The system may include one, more than one, and/or none of the components, features, benefits, and/or processes described and depicted in the following example.

As an example, a module (e.g., software) may be deployed on the customer's (e.g., hospital and/or clinic) equipment that understands the native languages of hospital systems. This module may turn a customer's device into the HIP server. The module may translate and post incoming requests from the medical systems to the main web server via HTTPS and/or communicate with a user device (e.g., the web module's client-side JavaScript) for requests to communicate with other systems at the customer's facility, such as a hospital system. When the module receives such requests from user device web module's JavaScript, it translates them into hospital systems' native language (such as HL7) and relays them onto appropriate hospital system.

The user device web module client-side JavaScript may contact HIP server, for example, whenever the user takes action in the main web app that involves an external hospital system (i.e. assign a patient, select a patient for reporting, sign report, addend report). The web server may handle such request as usual plus, as part of its normal response may instruct the client-side JavaScript to post to the HIP server (which is running on the same local network as the web browser and hospital systems) passing it a payload that contains the necessary information about which hospital system to contact and what to communicate to it. The user device web module client-side JavaScript may not have to understand any of this payload, other than what URL the HIP server is running at (to make an HTTP post to the HIP server).

Figure 9:
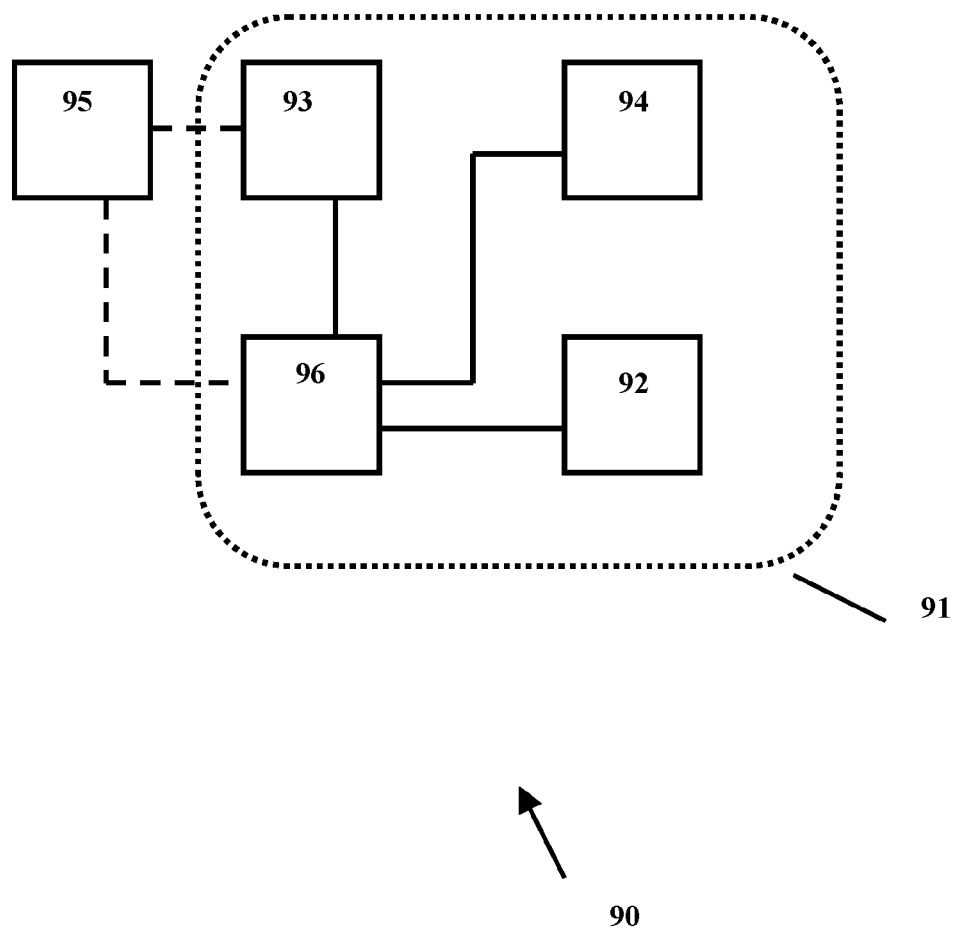
FIG. 9 illustrates an implementation of an example system that facilitates transmitting secure data.

FIG. 9 illustrates an example system 90 for transmitting secure data. The system may include a network A 91. A user such as a radiologist logs into a diagnosis web application or any other appropriate web application on her user device 93, such as a PC, Mac, or tablet running any HTML5-compatible web browser and establishes HTTPS connection (e.g., between the web server 95 and the user device 93) and corresponding browser session to the associated diagnosis web server 95.

Independently and separate from the user, the HIP 96 logs into the same diagnosis web server 95 via its own HTTPS connection (e.g., between the HIP and the web server) and establishes its own HTTPS session. The HIP 96 may run on a different device, in some implementations.

A Radiologist selects a patient for reporting from the worklist in the web app (e.g., generated by the web server 95) and/or signs a completed report.

JavaScript running in the web browser detects user's actions and sends HTTPS request (e.g., via a connection between the user device 93 and the web server 95) to the web server containing the information about the patient or the report from the previous step.

The web server 95 processes the HTTPS post and sends response back to the web app on the user device 93 with information about the selected patient/report and/or data containing instructions on how to contact the HIP server and what to instructions to pass to the HIP.

The web app JavaScript receives the web server's response, displays the relevant data and screens and establishes a new HTTP connection to the HIP server, passing HIP the data, as instructed by the web server. Direct HTTP connection may be possible because both the machine running the web browser and the machine running the HIP server are on the same local network within the hospital or clinic (e.g., which also reduces the need for encryption/HTTPS for communication between the two machines).

Depending on the web browser being used by the user, either XMLHttpRequest (or non-Internet Explorer web browsers) or hidden IFRAME post (Internet Explorer web browser) is used for communication from the web app JavaScript to the HIP server since different web browsers have different restrictions and security warnings on communication with non-origin server (i.e. server other than the primary web server that delivered the web page).

HIP 96 receives the data from web app's JavaScript and follows their instructions to make a connection (e.g., between the imaging workstation 94 and the HIP) (e.g., which may itself be another HTTP connection or COM/DCOM or HL7 sockets or any other appropriate protocol) to the imaging workstation (e.g., including PACS) containing selected patient's images (e.g., when a patient is selected) or to the reporting system (e.g., when a report is signed). The direct connection may be allowed since the HIP's computer and the medical system are on the same local network. The medical system processes HIP's request and responds with success and/or error.

HIP passes on the medical system's response to web app's JavaScript (e.g., via a connection between the HIP and the web server) for display to the user (e.g., in case of errors) and/or to the web server for logging or potentially raising alerts in case of errors. In some implementations, this may be useful when unexpected errors occur on the part of the medical systems.

In various implementations, a medical web-based application (e.g., running on a user device) may need to be able to initiate communication to hospital/clinic systems for imaging (e.g., through PACS, imaging workstations) and reporting (e.g. through RIS, BRIS, HIS, EHR). Hospital systems (e.g., RIS, BRIS, HIS, EHR) may need to be able to initiate communication to the web-based application (e.g. for building the patient worklist). Application web server(s) may be located on a local network in one data center. A Hospital/clinic system that web servers need to communicate with may be located in numerous other local networks/data centers which may be firewalled off from the Internet for security reasons and/or regulations (e.g., best practices, industry and/or government). Therefore these medical systems may not able to accept incoming connections from the web server since firewalls block all such incoming connections. In some instances they may also be unable to initiate outgoing connection to the web server, especially in protocols other than HTTP/S (again, for security reasons). In some implementations, restrictions to medical systems include ensuring that communication that travels over the Internet must be authenticated to make sure there is no spoofing of either the origin or destination system. In some implementations, communication that travels over the Internet must be encrypted which is not part of the design of most hospital systems (since they don't normally communicate over the Internet) or of the HL7 language.

Web application's "native language" may be HTTP/S (aka "web" and "web services"). A web application may not be easily able to incorporate HL7 in its design since HL7 is implemented at TCP/IP (aka "sockets") level using a set of rules (protocol) that are different and may be incompatible with HTTP/S. A web server may not be able to send or receive any TCP/IP traffic other than HTTP/S. A hospital system may require a separate application to process non-HTTP/S HL7 traffic and there may need to be a separate way for the web server and this non-HTTP/S application to communicate (e.g., by having an application talk both HTTP/S and HL7 or have them share data via a database or file system). The design, development, and maintenance of such a system becomes much more difficult compared to a "pure" HTTP/S-only web application. Thus, the described systems and methods may be utilized to facilitate communications.

In various implementations, the described systems and/or processes may be utilized instead of other protocol for one, more or none of the following reasons. The described systems and/or processes may be less expensive, quicker, and/or easier to maintain than other methods (e.g., VPN, on-the-premises listening proxy, and/or on-the-premises polling proxy) of securely transmitting data.

For example, virtual private networks (VPN) may not trivial to set up or maintain. They go down frequently and need to be re-set. Different firewall equipment on the hospital side and the web server side (which is unavoidable with more than one customer) may increase the likelihood of problems. Connecting the web server(s) to multiple customers' VPNs would essentially establish one giant VPN across all customers (with the web server's local network as the connection point). This means one customer's equipment would be open to another customer's network which may violate any reasonable IT security policy. Hospital's IT department and web application's cloud host's IT department may become part of all development, testing, deployment, and resolving any connectivity problems. This may add two new entities to all processes that should only involve the web app development/support team and the end customer. Everything from development to problem resolution may happen a lot slower as the result. VPN does not solve the problem of different "native languages" for different systems. The web app would still need to run a separate socket server to listen for incoming socket/HL7 communication and to send outgoing HL7 communication. There would then need to be a separate interface between the web server(s) and this other socket server(s). Each new VPN required for a new customer may multiply the problems listed above.

Thus, when compared to VPN, the described HIP-based systems and processes may significantly reduce the application maintenance effort by eliminating the need for a VPN setup, troubleshooting, and maintenance.

As another example, on-the-premises listening proxy may deploy a piece of software on the customer's equipment (or potentially web app's own equipment hosted within the hospital's network) that "understands" the native HL7 (or other) language of hospital systems and (a) translates and posts incoming requests from hospital's system to the web server via HTTPS and (b) opens a permanent secure socket (TCP/IP, not HTTP) connection on which it listens for and executes requests from the web server to communicate to imaging and reporting systems, translating its requests into hospital systems' native language (such as HL7) and communicating them to the appropriate systems. Note that step (b) calls for a non-standard, non-HTTP/S solution because HTTP/S does not provide for a standard way to "push" notifications from the web server to the on-the-premises listening proxy. HTTP/S "push" solutions such as Comet are highly unreliable and incompatible with some web technologies, including the most popular one: Apache/PHP (aka LAMP), used by medical software such as diagnosis software. WebSockets technology is currently being developed to address this issue but it is very immature and not universally supported (including, again, not by Apache/PHP). At most only one new outgoing firewall rule may be needed to allow the listening socket connection in step (b). Encryption and authentication of patient diagnosis requests is accomplished via HTTPS in step (a). Encryption of imaging/reporting requests is accomplished via listening secure socket connection in step (b). Socket programming is hard and secure socket programming is harder. Maintaining and expanding custom socket code to communicate with more and more hospital systems is harder still. Such implementation may require a separate mechanism to authenticate the listening socket connection (b) since web app's native authentication only works over HTTP/S. Such implementation may require separate socket server(s) to accept the incoming listening connection (b) and a way to interface between this socket server(s) and the main web server(s). Such implementation may still run into conflicts with customer's security policies for opening a non-standard outgoing socket connection.

Thus, when compared to on-the-premises listening proxy, the described HIP-based systems and processes may significantly reduce the application development and maintenance effort by eliminating and/or significantly reducing the amount of sockets programming.

As another example, On-the-premises polling proxy may deploy a piece of software on the customer's equipment (or potentially web app's own equipment hosted within the hospital's network) that "understands" the native HL7 (or other) language of hospital systems and (a) translates and posts incoming requests from hospital's system to the web server via HTTPS and (b) opens a permanent HTTPS connection to the web server which it uses to continuously poll the web server on whether there are any pending requests to communicate to imaging and reporting systems. If there are such requests pending the web server would pass them on to the proxy in a reply to one of the polls and the proxy would translate those requests into hospital systems' native language (such as HL7) and communicate them to the appropriate systems. Note that step (b) calls for a continuous polling (i.e. continuous sending of "do-I-have-anything-to-do?" requests to the web server) because HTTP/S does not provide for a standard way to "push" notifications from the web server to the on-the-premises listening proxy. Such implementation would have the advantage of having no networking/firewall/security issues because all communication is done via HTTPS as in a "regular" web app. Because HTTPS is used such implementation would also have no encryption or authentication issues. All encryption and authentication is done via HTTPS as in a "regular" web app. Such implementation would only need straightforward programming using standard HTTP/S protocols and would have no need for a separate socket server. Existing web server may handle proxy requests exactly as it handles regular web app requests. However such implementation has a large performance downside. Requests to pull up a patient's image especially are very time sensitive (radiologist may be waiting for the images to be pulled up by the next request), so the polling would have to be done at least once a second—ideally even more often. That means that each on-the-premises polling proxy for each of the customers' local networks would have to poll the web server(s) at least once a second, with each request requiring at least one database look-up at the web server (to see if there are requests pending). This may be acceptable for a small number of customers but may quickly overwhelm the server capacity as the number of customers and proxies grows to dozens and hundreds. Vast majority of these polling requests may come back "empty", with no request pending, but the web server(s) may still have to spend cycles handling them and doing empty database lookups. The web server(s) and databases would have to become much more powerful—and expensive—than necessary simply to handle all the polling requests.

Thus, when compared to on-the-premises polling proxy, the described HIP-based systems and processes may eliminate and/or reduce the performance overhead caused by the continuous polling. Instead of continuously polling the web server to see if there are any requests, the client-side JavaScript of the web app may combine with the HIP server to form a "hybrid intelligent proxy" that is able to follow web server's instructions to allow communicating with the appropriate hospital system precisely in response to user's actions necessitating such communication.

End of Example 1

Although several of the described systems and/or processes have been described in terms of a medical setting, medical data, and/or medical personnel, the described systems and/or processes may be utilized with other types of data. For example, similar systems and/or processes may be utilized to facilitate communications involving other types of data in which access is restricted. Web based applications are used in a variety of industries and communication of secure data within a facility of an industry may be facilitated utilizing similar systems and/or processes. For example, access to industrial trade secret data and/or corporate best practices may be restricted; however, use of a web based application may facilitate worker productivity, for example. The web-based application in conjunction with a HIP server may be utilized to facilitate communications between user computers for the presentation of information a user desires, while maintaining security.

Although two user devices have been described in various implementations, a user may have one device, two devices, or more devices, as appropriate.

Although specific implementations have been described in FIGS. 1, 6, 8 and 9, the devices (e.g., user devices, HIP server, medical data system, and/or web server) may be any appropriate computer or other programmable logic device. The devices may include a processor that executes instructions and manipulates data to perform operations of the controller. Processor may include a programmable logic device, a microprocessor, or any other appropriate device for manipulating information in a logical manner. Multiple processors may be used according to particular needs, and reference to processor is meant to include multiple processors where appropriate.

A memory of the device may include any appropriate form(s) of volatile and/or nonvolatile memory. Memory may include one or more forms of memory such as volatile memory (e.g., RAM) or nonvolatile memory, such as read-only memory (ROM), optical memory (e.g., CD, DVD, or LD), magnetic memory (e.g., hard disk drives, floppy disk drives), NAND flash memory, NOR flash memory, electrically-erasable, programmable read-only memory (EEPROM), Ferroelectric random-access memory (FeRAM), magnetoresistive random-access memory (MRAM), non-volatile random-access memory (NVRAM), non-volatile static random-access memory (nvSRAM), and/or phase-change memory (PRAM). The memory of a device may include a database. A variety of repositories may be used, such as, SQL databases, relational databases, object oriented databases, distributed databases, XML databases, and/or web server repositories.

In addition, various software (e.g., modules) may be stored on the memory of a device. For example, instructions (e.g., operating systems and/or other types of software), and/or modules, such as modules on the HIP server, a management web module and/or a management module. In some implementations, modules may be combined, such as into a single module or multiple modules. Modules may include various modules and/or sub-modules. The modules may include one or more of the operations described in processes 20, 30, 40, 50, and/or 70. The modules may be executed by a processor on the appropriate device (e.g., first user device, second user devices, HIP, web server, AD, and/or SDA).

A communication interface may allow the device(s) to communicate with each other and/or other computer systems (e.g., third party software). The communication interface may transmit data and/or receive data from other components, other repositories, and/or other computer systems via network protocols (e.g., TCP/IP, Bluetooth, and/or Wi-Fi) and/or a bus (e.g., serial, parallel, USB, and/or FireWire). Operations of various modules stored in a memory may be updated and/or altered through the communication via network protocols (e.g., remotely through a firmware update and/or by a device directly coupled to the controller).

Although specific components have been described in FIGS. 1-9, the components may be any appropriate computer or other programmable logic device. For example, first user device A, second user device B, AD, SDA, HIP, and/or other components may include any appropriate device, such as a computer or programmable logic device.

The components (e.g., first user device A, second user device B, AD, SDA, HIP, and/or other components of the systems) may include a processor that executes instructions and manipulates data to perform operations of the component. A processor may include a programmable logic device, a microprocessor, or any other appropriate device for manipulating information in a logical manner and memory may include any appropriate form(s) of volatile and/or nonvolatile memory, such as RAM and/or Flash memory.

The memory may include data, such as secure data, unsecure data, various criteria to utilize facilitate analysis, restrictions, and/or any other data useful to the operation of system. For example, the memory may store secure data such as electronic medical records, test results, diagnostic imaging, patient information, and/or other types of secure data. The memory may store data such as access criteria utilized to determine which components may access other components; communication protocol; and/or other appropriate data.

In addition, various software (e.g., instructions to allow performance of operations) may be stored on the memory. For example, instructions (e.g., operating systems, modules and/or other types of software) may be stored on a memory of appropriate components (e.g., first user device A, second user device B, AD, SDA, HIP, and/or other components of the systems). The module(s) of various components may include instructions to perform one or more of the operations described in processes 20, 30, 40, 50, and/or 70, such as operations to facilitate the transmission of secure and/or unsecure data. For example, a module of the first user device may be stored on a memory of the first user device and/or executed by a processor of the first user device. The module may include instructions to allow accessing an interface generated by the AD, transmitting a request for secure data, transmitting a request for presentation of the secure data on another device (e.g., a second user device), receiving instructions to allow a HIP, transmitting instructions to HIP, sending and/or receiving notifications, and/or other any other appropriate operations.

The a module of the second user device may be stored on a memory of the second user device and/or executed by a processor of the second user device. The module may include instructions to allow presenting secure and/or unsecure data, accessing software for presenting and/or retrieving secure data, receiving instructions to allow the request of secure data (e.g., from a HIP), retrieving secure data and/or unsecure data, presenting secure and/or unsecure data, and/or any other appropriate operations.

In some implementations, a module of the AD may be stored on a memory of the AD and/or executed by a processor of the AD. The module may include instructions to allow generating interface(s) (e.g., for presentation via a website to a first user device), analyzing information, receiving selections via the interface(s), determining secure data associated with received selections (e.g., via a table of associations stored in a memory of the AD), receiving request for secure data (e.g., from a first user device), generating instructions to allow retrieving and/or presenting the requested secure data, transmitting the instructions to a component (e.g., first user device), receiving and/or transmitting notifications, establishing keys or other types of security associations with other components (e.g., HIP), receiving security associations, and/or any other appropriate operations.

In some implementations, a module of the HIP may be stored on a memory of the HIP and/or executed by a processor of the HIP. The module may include instructions to allow establishing a key or other type of security association with other components, restricting access to secure data (e.g., based on criteria such as failure to provide an appropriate key), transmitting and/or receiving notifications (e.g., based on successful and/or unsuccessful transmissions), determining where to transmit received instructions, determining whether to transmit received instructions, and/or other appropriate operations.

In some implementations, a module of the SDA may be stored on a memory of the SDA and/or executed by a processor of the SDA. The module may include instructions to allow receiving request for secure data, determining whether to allow access to the secure data, retrieving secure data, storing secure data, transmitting the secure data, and/or any other appropriate operations.

In some implementations, modules may be combined, such as into a single module or multiple modules. In an implementation, operation modules may include various modules and/or sub-modules.

A communication interface may allow the components to communicate with and/or restrict communications with other components of the system and/or other computer systems. The communication interface may transmit data from the controller and/or receive data from other components, other repositories, and/or other computer systems via network protocols (e.g., TCP/IP, Bluetooth, and/or Wi-Fi) and/or a bus (e.g., serial, parallel, USB, and/or FireWire). For example, a communication interface of the first user device may allow the first user device to communicate with other components, such as the AD and/or HIP. The communication interface of the AD may allow the AD to communicate with other components, such as the first user device and/or HIP. The communication interface of the second user device may allow the second user device to communicate with the HIP and/or SDA; and, the communication interface of the second user device may restrict communications with the first user device and/or the AD. The communication interface of the SDA may allow the SDA to communicate with the HIP and/or second user device; and, the communication interface of the SDA may restrict communications with the first user device and/or the AD.

The controller may include a presentation interface to present data to a user, such as though a monitor and speakers. The presentation interface may facilitate receipt of requests for operation from users. For example, the second user device may include a presentation interface, such as a monitor, on which the secure data may be presented to a user. The first user device may include a presentation interface, such as a touch screen, on which a web application may be presented to the user.

A client (e.g., first user device) may allow a user to access the AD and/or instructions stored on the AD. In some implementations, the second user device may be a client that allows a user to access the SDA and/or data stored on the SDA. A client may be a computer system such as a personal computer, a laptop, a personal digital assistant, a smart phone, or any computer system appropriate for communicating with the controller.

Although FIGS. 1, 6, 8, and 9 provide examples of devices that may be used with the disclosure, the various devices (e.g., user device, HIP server, medical data system, and/or web server) can be implemented through computers such as servers, as well as a server pool. In some implementations, first user device A, second user device B, AD, SDA, and/or HIP may include any appropriate device, such as a computer. For example, a computer may include a general-purpose personal computer (PC) a Macintosh, a workstation, a UNIX-based computer, a server computer, or any other suitable device. According to one implementation, a device may include a web server. A device may be adapted to execute any operating system including UNIX, Linux, Windows, or any other suitable operating system. The device may include software and/or hardware in any combination suitable to provide access to data and/or translate data to an appropriate compatible format.

In various implementations, graphical user interface (GUI) may be generated by the management module (e.g., of the AD and/or other modules and may be displayed on a presentation interface (e.g., a monitor or screen of the first and/or second user device). GUI may be operable to allow the user of a user device to interact with repositories and/or various interface(s). Generally, GUI provides a user with an efficient and user-friendly presentation of data provided by the system. GUI includes a plurality of displays having interactive fields, such as image icons, pull-down lists, fillable fields, and editable text operated by the user. And in one example, GUI presents an explore-type interface and receives commands from the user. It should be understood that the term graphical user interface may be used in the singular or in the plural to describe one or more graphical user interfaces in each of the displays of a particular graphical user interface. Further, GUI contemplates any graphical user interface, such as a generic web browser, that processes information in the system and/or user device and efficiently presents the information to the user. In some implementations, GUI may present a web page embedding content. The server can accept data from a user device(s) via the web browser (e.g., Microsoft Internet Explorer, Safari, or Mozilla FireFox) and return the appropriate Hyper Text Markup Language (HTML) or eXtensible Markup Language (XML) responses.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable signal(s) may be non-transitory waves and/or non-transitory signals.

In various implementations, a first device is restricted from communicating with a second device. In some implementations, the first device may be restricted from communicating with the second device since the communication protocols of the first device and the second device are not compatible (e.g., a first device communicates in HTTPS requests and a second device is restricted from accepting HTTPS requests). The first device may be restricted from communicating with the second device because the first device and the second device may not be communicably coupled. In some implementations, the first device may be restricted from communicating with the second device because the second device is restricted from communicating with devices that reside outside the network in which the second device resides. The first device may be restricted from communicating with the second device due to permissions (e.g., Internet access) of the first device.

Although users have been described as a human, a user may be a person, a group of people, a person or persons interacting with one or more computers, and/or a computer system.

Various described patents have been incorporated by reference. The described patents are incorporated by reference to the extent that no conflict exists between the various described systems and/or processes and the described patents. Any portion, of the described patents that are incorporated by reference, that is conflicting with the various described systems and/or processes are not incorporated by reference.

It is to be understood the implementations are not limited to particular systems or processes described which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "a module" includes a combination of two or more modules and reference to "device" includes different types and/or combinations of devices. As another example, "coupling" includes wired connections and/or wireless connections of computers.

While the present disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

The invention claimed is:

1. A method of accessing secure data, the method comprising:
   requesting, by a web module of a first user device on a first network from an application web server on an external network, presentation on the first user device of one or more diagnostic interfaces generated by the application web server; wherein the one or more diagnostic interfaces provide image icons, selection of a portion of which automatically prepares one or more diagnoses of test results;
   providing, by the application web server, the one or more diagnostic interfaces to the first user device for presentation;
   initiating transmission, by the first user device via the one or more diagnostic interfaces presented on the first user device, of a request to the application web server for presentation on a medical data presentation module of the first user device of secure data related to at least one of the one or more diagnostic interfaces, wherein the secure data is stored on a secure data administrator on the first network, wherein the application web server is restricted from directly accessing the secure data, and wherein the medical data presentation module and the secure data administrator are restricted from accepting incoming communication initiated by the application web server and the web module;
   receiving, by the web module of the first user device from the application web server, instructions generated by the application web server facilitating communication between a HIP module executing on one or more processors on the first network and the secure data administrator, the instructions related to the presentation of the secure data on the medical presentation module, wherein the instructions include a key, and wherein the HIP module is restricted from accepting incoming communication initiated by the application web server; and
   transmitting, by the web module of the first user device to the HIP module, at least a portion of the instructions including the key, wherein the HIP module is communicably coupled to the secure data administrator;
   determining, by the HIP module, that the key is valid and translating the at least the portion of the instructions; and
   transmitting, by the HIP module, the translated instructions to the secure data administrator, wherein processing of the translated instructions by the secure data administrator allows the secure data administrator to push at least a portion of the secure data to the medical data presentation module of the first user device for presentation.

2. The method of claim 1 wherein the secure data comprises at least one of diagnostic images, test results, patient information, or electronic medical record information.

3. The method of claim 1 wherein the instructions comprise a format readable by the secure data administrator.

4. The method of claim 1 further comprising establishing a connection between the HIP module and the application web server, wherein the HIP module establishes the connection.

5. The method of claim 1 wherein the secure data comprises breast imaging, and wherein the one or more diagnoses of test results are based on breast imaging.

6. The method of claim 1 further comprising:
receiving, by the application web server, one or more follow up test results for a plurality of patients;
determining, by the application web server, one or more outcomes to associate with image icons based on previously received image icon selections for the plurality of patients and the received one or more follow up test results;
receiving, by the application web server from the first device, selection of the one or more of the image icons through the one or more generated diagnostic interfaces for a new patient;
determining, via the application web server, one or more outcomes for the new patient based on the received selection of the one or more of the image icons for the new patient and the determined one or more outcomes to associate with image icons.

7. The method of claim 1 further comprising:
receiving, at the application web server, a selection of one or more of the image icons from the first user device through the one or more diagnostic interfaces;
automatically generating a report comprising the one or more diagnoses of the test results based on the selected one or more image icons.

8. The method of claim 7 wherein at least one of the one or more diagnostic interfaces further comprises association icons, wherein each of the association icons indicates a relationship between two or more of the image icons of the one or more diagnosis interfaces when selected, and wherein the automatically generated report comprises:
retrieving one or more templates including words comprising a diagnosis based on the selected one or more image icons and one or more association icons selected via the one or more diagnostic interfaces presented on the first user device; and
generating the report is further based on the one or more templates.

9. The method of claim 1 further comprising:
receiving, at the application web server, a selection of one or more anatomical locations from the first user device via the one or more diagnostic interfaces;
restricting, by the application web server, selection of one or more of the image icons until the selection of the one or more anatomical locations has been received from the first user device via the one or more diagnostic interfaces.

10. The method of claim 1 wherein at least two of the image icons of the one or more diagnostic interfaces comprises:
a first breast image comprising a representation of lymph nodes proximate a breast; and
a second breast image comprising a transverse view of a breast.

11. The method of claim 1 further comprising:
receiving, at the application web server, a selection of one or more of the image icons from the first user device through the one or more diagnostic interfaces;
receiving, at the application web server via at least one of the one or more diagnostic interfaces presented on the first user device, a request for reference information associated with at least one of the selected one or more of the image icons; and
retrieving, by the application web server, a first set of reference information from a database based on at least one of the selected one or more of the image icons, wherein reference information in the database is indexed based at least partially on one or more relationships to one or more of the image icons; and
allowing, by the application web server on the first user device via at least one of the one or more diagnostic interfaces, presentation of the first set of reference information.

12. A system comprising:
an application web server residing on a external network, wherein the external network is external to a first network on which a first user device resides, wherein the application web server comprises:
a first memory storing application device instructions; and
a first processor configured to execute one or more application device instructions to:
generate, in response to a request from a web module of the first user device, one or more diagnostic interfaces to be presented on a first user device; wherein the one or more diagnostic interfaces provides image icons, selection of which automatically prepares one or more diagnoses of test results;
providing, by the application web server, the one or more diagnostic interfaces to the first user device for presentation;
receive a second request from the web module of the first user device, via at least one of the generated one or more diagnostic interfaces, for presentation on a medical data presentation module of the first user device of secure data related to at least one of the generated one or more diagnostic interfaces; wherein the secure data is stored on a secure data administrator on the first network; wherein the application web server is restricted from directly accessing the secure data, and wherein the medical data presentation module and the secure data administrator are restricted from accepting incoming communication initiated by the application web server and the web module;
generate first instructions facilitating communication between a HIP module on the first network and the secure data administrator, the first instructions related to the presentation of at least a portion of the secure data on the medical data presentation module, wherein the first instructions include a key, and wherein the HIP module is restricted from accepting incoming communication initiated by the application web server; and
initiate transmission of the generated first instructions to the first user device; and
the system further comprising the HIP module residing on the first network, the HIP module configured
to execute, via one or more processors accessible by the HIP module, one or more HIP instructions to:
receive at least a portion of the first instructions including the key from the web module of the first user device;
determine that the key is valid and translating the first instructions; and transmit at least a portion of the translated first instructions to the secure data administrator, wherein processing of the translated first instructions by the secure data administrator allows the secure data administrator to push at least a portion of the secure data to the medical data presentation module of the first user device for presentation;

wherein the HIP module is restricted from accepting incoming communication initiated by the application web server.

13. The system of claim 12 further comprising the first user device, wherein the first user device comprises:

a third memory storing first user device instructions; and a third processor configured to execute one or more of the first user device instructions to:

request, via the web module of the first user device, access to the secure data through one or more of the generated one or more diagnostic interfaces;

receive, via the web module, the first instructions from the application web server to allow access to the secure data on the medical data presentation module of the first user device.

14. The system of claim 12 wherein the secure data comprises at least one of test results, patient information, electronic medical record information, or diagnostic images.

15. The system of claim 12 wherein the HIP module resides on a HIP server.

16. The system of claim 12 wherein the first instructions comprise a format readable by the secure data administrator.

17. The system of claim 12 wherein the one or more HIP instructions further comprise establish, via the HIP module, a connection between the HIP module and the application web server.

18. The system of claim 12 wherein the secure data comprises breast imaging, and wherein the one or more diagnoses of test results are based on breast imaging.

19. The system of claim 12 wherein the image icons of the one or more diagnostic interfaces comprises at least a portion of at least one of one or more CT scans, one or more mammograms, one or more radiographs, one or more MRI scans, one or more PET scans, one or more ultrasounds, or one or more other medical imaging exams.

* * * * *